United States Patent
Lu et al.

(10) Patent No.: US 11,059,885 B2
(45) Date of Patent: *Jul. 13, 2021

(54) ANGIOPOIETIN 2, VEGF DUAL ANTAGONISTS

(71) Applicant: AskGene Pharma Inc., Camarillo, CA (US)

(72) Inventors: Yuefeng Lu, Newbury Park, CA (US); Jian-Feng Lu, Oak Park, CA (US)

(73) Assignee: AskGene Pharma Inc., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,852

(22) Filed: Apr. 10, 2019

(65) Prior Publication Data

US 2020/0102381 A1  Apr. 2, 2020

Related U.S. Application Data

(63) Continuation-in-part of application No. 15/593,280, filed on May 11, 2017, now Pat. No. 10,654,922.

(60) Provisional application No. 62/655,436, filed on Apr. 10, 2018, provisional application No. 62/336,522, filed on May 13, 2016, provisional application No. 62/448,998, filed on Jan. 21, 2017, provisional application No. 62/459,046, filed on Feb. 14, 2017.

(51) Int. Cl.
| | | |
|---|---|---|
| *C07K 16/22* | (2006.01) | |
| *A61K 9/08* | (2006.01) | |
| *A61K 9/19* | (2006.01) | |
| *C07K 14/71* | (2006.01) | |
| *C07K 14/515* | (2006.01) | |

(52) U.S. Cl.
CPC ............. *C07K 16/22* (2013.01); *A61K 9/08* (2013.01); *A61K 9/19* (2013.01); *C07K 2317/55* (2013.01); *C07K 2317/622* (2013.01)

(58) Field of Classification Search
CPC ............ C07K 2319/00; C07K 2319/30; C07K 2317/56; C07K 14/515; C07K 14/71; C07K 16/22; C07K 2317/622; C07K 2317/55; C07K 2319/32; C07K 2317/73; C07K 2317/24; C07K 2317/76; A61P 35/00; A61K 9/08; A61K 9/19

See application file for complete search history.

(56) References Cited

U.S. PATENT DOCUMENTS

| | | | | |
|---|---|---|---|---|
| 7,138,370 B2* | 11/2006 | Oliner | ...................... | A61P 17/06 |
| | | | | 514/1.1 |
| 7,608,429 B2* | 10/2009 | Reilly | ...................... | C07K 16/22 |
| | | | | 435/69.6 |
| 8,143,380 B2* | 3/2012 | Walker | ...................... | A61P 43/00 |
| | | | | 530/391.7 |
| 8,574,577 B2* | 11/2013 | Barbas, III | ....... | C07K 14/70557 |
| | | | | 424/134.1 |
| 10,654,922 B2* | 5/2020 | Lu | ........................... | C07K 16/22 |

FOREIGN PATENT DOCUMENTS

| WO | WO-2006010057 A2 * | 1/2006 | ............. A61K 47/60 |
|---|---|---|---|
| WO | WO-2009136352 A1 * | 11/2009 | ............. A61K 47/64 |

OTHER PUBLICATIONS

Colman et al., Research in Immunology (145(1):33-36 (Year: 1994).*
Presta et al., Cancer Research 57:4593-4599 (Year: 1997).*

* cited by examiner

*Primary Examiner* — Phuong Huynh

(74) *Attorney, Agent, or Firm* — Entralta P.C.; James F. Fleming; Peter D. Weinstein

(57) ABSTRACT

The present disclosure relates to fusion molecules and chimeric molecules which comprise two components: an Ang-2 antagonist peptide linked to a VEGF-binding moiety. Further disclosed are methods of using said chimeric molecules to treat a patient cancer, proliferative retinopathy, neovascular glaucoma, macular edema, wet age-related macular degeneration (wAMD), macular edema following retinal vein occlusion (RVO), diabetic macular edema (DME), or diabetic retinopathy (DR).

7 Claims, 5 Drawing Sheets

Specification includes a Sequence Listing.

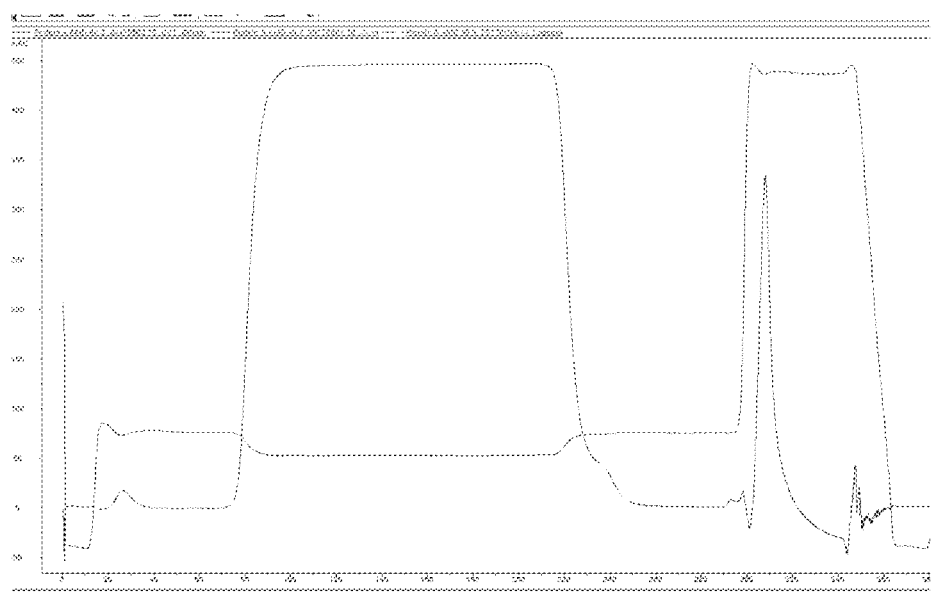
Figure 1. Protein A Affinity Chromatography.

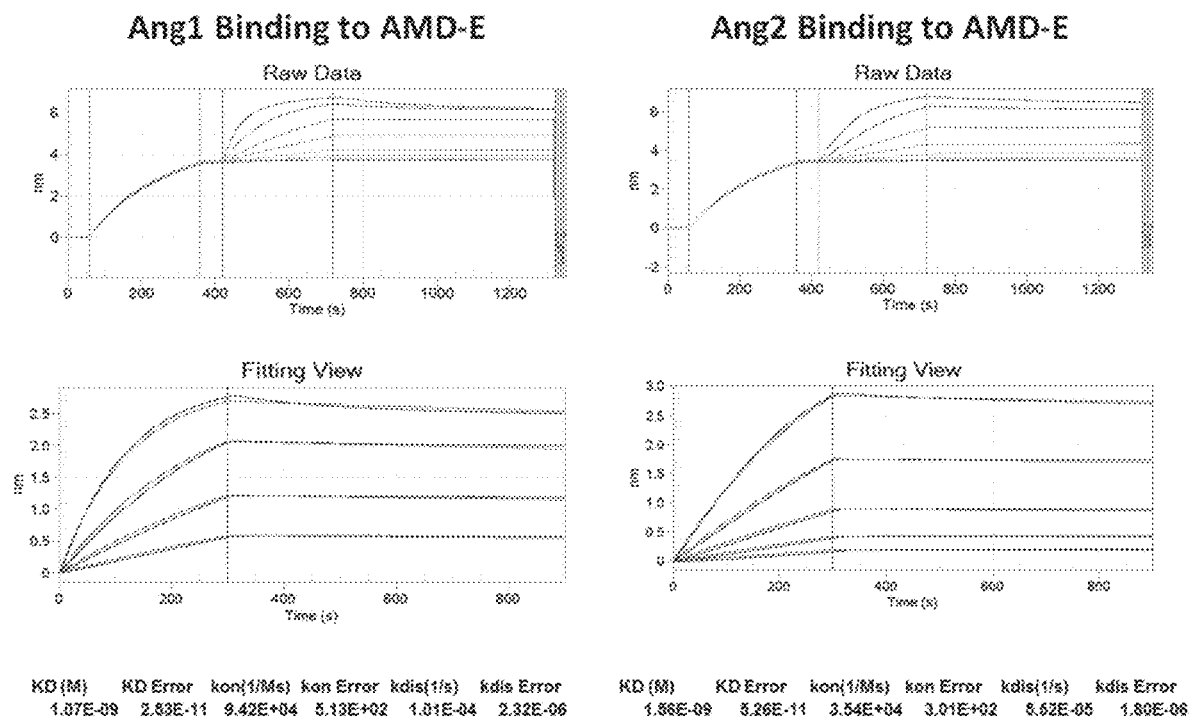
Figure 2. Kinetics of Ang-1 or Ang-2 Binding to AMD-E As Analyzed by Octet Red96.

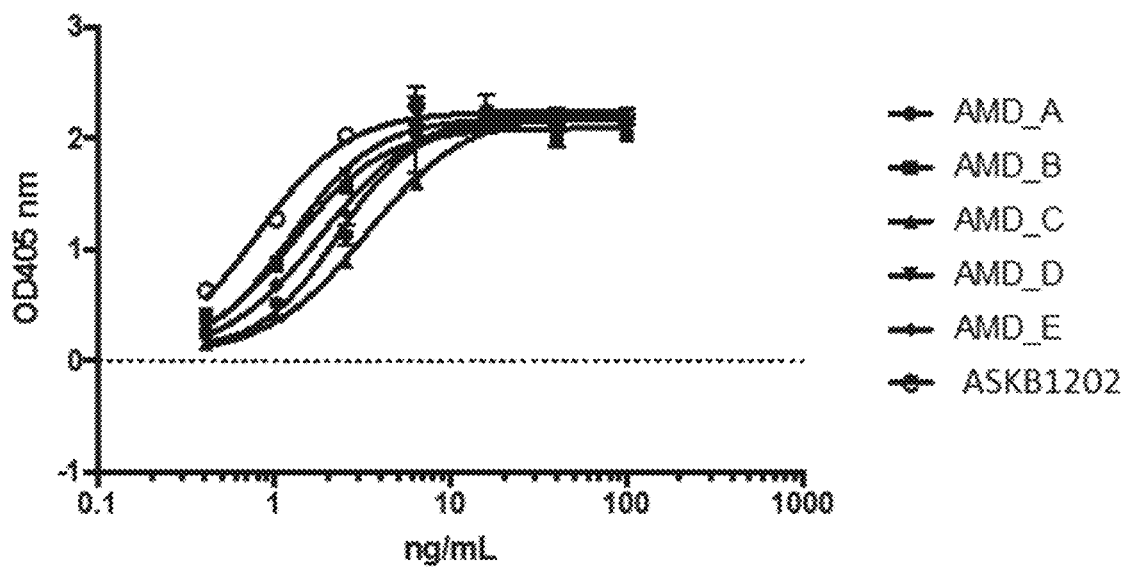
Figure 3. Blocking of Binding of Ang-1 and Ang-2 to Tie-2 by AMD-E

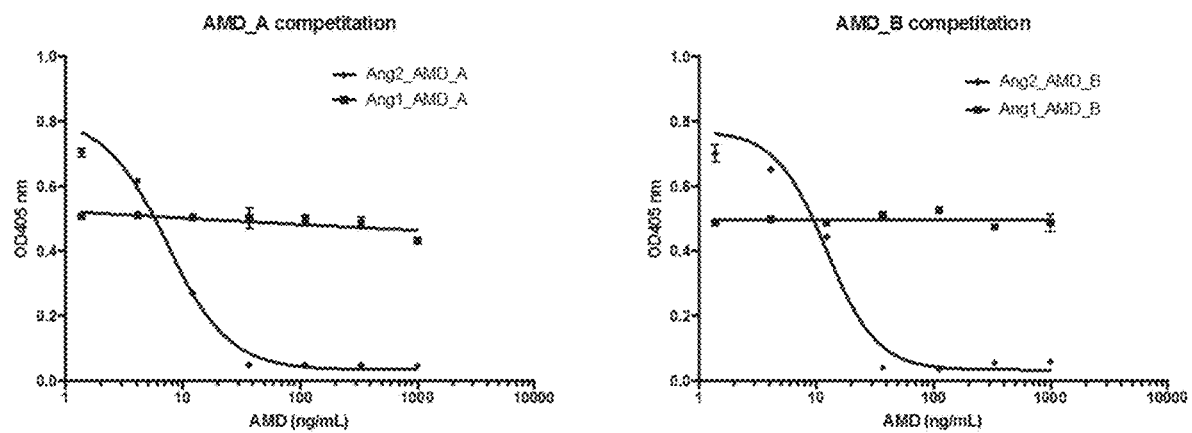
Figure 4A. Blocking of Binding of Ang-1 and Ang-2 to Tie-2 by AMD-A and AMD-B
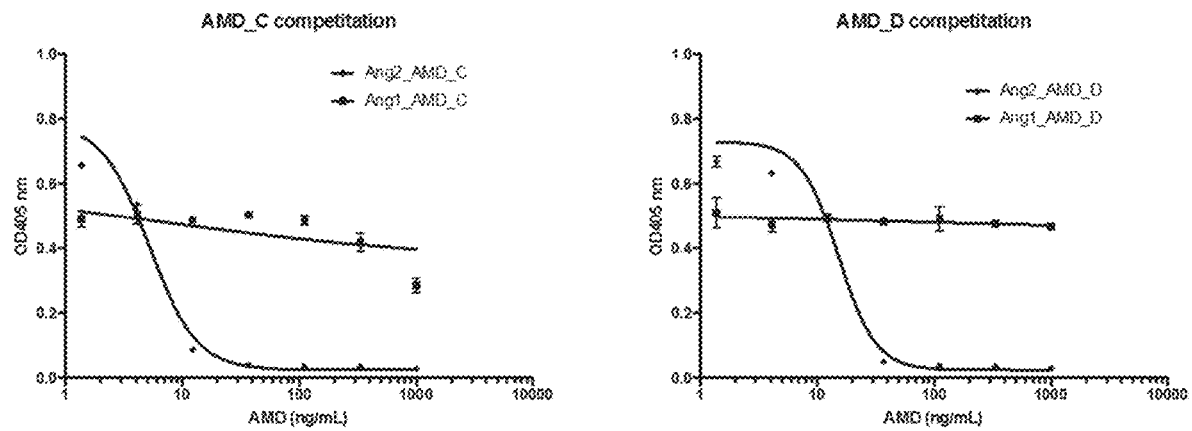
Figure 4B. Blocking of Binding of Ang-1 and Ang-2 to Tie-2 by AMD-C and AMD-D Figure 5. Blocking of Binding of Ang-2 to Tie-2 by 712-O and 712-O2 molecules
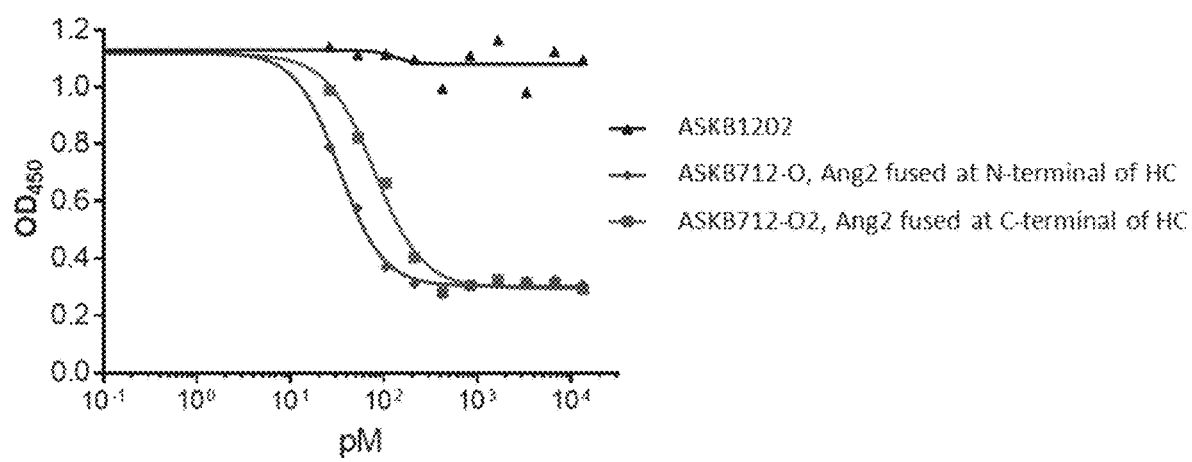
|  | 712-O, N terminal | 712-O2, C terminal |
|---|---|---|
| EC50, pM | 33.1 | 78.2 |

ANGIOPOIETIN 2, VEGF DUAL ANTAGONISTS

CROSS-REFERENCE TO RELATED APPLICATIONS

The present application is a Continuation-in-part of U.S. patent application Ser. No. 15/593,280 (now U.S. Pat. No. 10,654,922) and claims priority to Provisional patent Application 62/336,552, filed May 13, 2016, Provisional Patent Application 62/459,046, filed Feb. 14, 2017 and Provisional Patent Application 62/448,998, filed Jan. 21, 2017, herein both incorporated by reference in their entirety. The present application also claims priority to U.S. patent application Ser. No. 15/593,280 filed May 11, 2017, herein incorporated by reference in its entirety. The present application further claims priority to U.S. patent applications 62/655,436 filed on Apr. 10, 2018, herein incorporated by reference in its entirety.

REFERENCE TO SEQUENCE LISTING

The entire content of the following electronic submission of the sequence listing via the USPTO EFS-WEB server, as authorized and set forth in MPEP § 1730 II.B.2(a)(C), is hereby expressly incorporated by reference in its entirety for all purposes. The sequence listing is identified on the electronically filed text file as follows: File Name: AG3-018US-SeqList_ST25; Date of Creation: Sep. 10, 2020; Size (bytes): 180 KB.

FIELD OF THE INVENTION

The present application relates to novel molecules comprising binding domains to both VEGF and Ang2.

Introduction

Angiogenesis is implicated in the pathogenesis of a variety of disorders including solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al, Annu. Rev. Physiol. 53 (1991) 217-239; and Garner, A., Vascular Diseases, in: Pathobiology of Ocular Disease, A Dynamic Approach, Garner, A., and Klintworth, G. K. (eds.), 2nd edition, Marcel Dekker, New York (1994), pp. 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in a number of cancers (see, e.g., Weidner, N., et al, N Engl J Med. 324 (1991) 1-8; Horak, E. R., et al, Lancet 340 (1992) 1120-1124; and Macchiarini, P., et al, Lancet 340 (1992) 145-146).

Human vascular endothelial growth factor (VEGF/VEGF-A) is described in, e.g., Leung, D. W., et al, Science 246 (1989) 1306-9; Keck, P. J., et al, Science 246 (1989) 1309-12 and Connolly, D. T., et al, J. Biol. Chem. 264 (1989) 20017-24. The expression of VEGF is potentiated in response to hypoxia, by activated oncogenes, and by a variety of cytokines. VEGF is involved in the regulation of normal and abnormal angiogenesis and neovascularization associated with tumors and intraocular disorders (Ferrara, N., et al, Endocr. Rev. 18 (1997) 4-25; Berkman, R. A., et al, J. Clin. Invest. 91 (1993) 153-159; Brown, L. F., et al, Human Pathol. 26 (1995) 86-91; Brown, L. F., et al, Cancer Res. 53 (1993) 4727-4735; Mattern, J., et al, Brit. J. Cancer. 73 (1996) 931-934; and Dvorak, H. F., et al, Am. J. Pathol. 146 (1995) 1029-1039).

Deregulated VEGF expression contributes to the development of solid tumors by promoting tumor angiogenesis and to the etiology of several additional diseases that are characterized by abnormal angiogenesis (Kim, K. J., et al., 1993. Nature (London) 362, 841-844; Millauer, B., et al., 1994. Nature (London) 367, 576-579). Consequently, inhibition of VEGF signaling abrogates the development of a wide variety of tumors.

In retinopathies, in which partial or general ischemia of the retina is accompanied by overexpression of VEGF and hyperproliferation of blood vessels, blindness can result (Aiello, L. P et al., 1994. N. Engl. J. Med. 331, 1480-1487; Adamis, A. P., et al., Am. J. Ophthalmol. 118, 445-450). Inhibition of VEGF expression in such disease states can treat or prevent resulting blindness.

Human angiopoietin-2 (ANG-2 or Ang-2 or Ang2) (alternatively abbreviated with ANGPT2 or ANG2) is described in Maisonpierre, P. C., et al, Science 277 (1997) 55-60 and Cheung, A. H., et al, Genomics 48 (1998) 389-91. Ang2 plays an important role in angiogenesis and its expression levels have been correlated with cancer and eye diseases (Gerald D et al., Cancer Res. 2013, 73(6):1649-57; Watanabe et al., Am J Ophthalmol. 2005, 139(3):476-81).

Dual antagonist RG7716 demonstrated superior efficacy than VEGF antagonist ranibizumab in a recent clinical trial. However, the reported dosage for RG7716 at 6 mg per dose was rather high considering the volume of administration to eye is typically low, e.g. 50 micoL). This could require a concentration of 120 mg/ml, a significant challenge for formulation development. A dual antagonist with stronger binding affinities to VEGF and/or Ang2 is needed. The present invention includes bi-specific molecules with enhanced binding ability and which result in a reduction in the severity of a disease in a patient treated with a molecule disclosed herein.

SUMMARY

The present disclosure relates to novel bispecific chimeric molecules comprising binding domains to both VEGF and Ang-2. Further disclosed are methods of using said chimeric molecules to treat a patient of cancer, proliferative retinopathy, neovascular glaucoma, macular edema, wet age-related macular degeneration (wAMD), macular edema following retinal vein occlusion (RVO), diabetic macular edema (DME), or diabetic retinopathy (DR).

In some aspect, said chimeric molecule comprises one or two VEGF-binding moieties and one or two Ang-2 antagonist peptides, wherein:
 a) said Ang-2 antagonist peptide comprises an amino acid sequence selected from SEQ ID NO: 8-14; and
 b) said VEGF-binding moiety is an antibody, an Fab or an scFv; and wherein said antibody, Fab or scFv comprises light chain CDRs as derived from a light chain with an amino acid sequence as shown in SEQ ID NO: 4, or derived from a scFv with an amino acid sequence as shown in SEQ ID NO: 6, and heavy chain CDRs as derived from a heavy chain with an amino acid sequence as shown in SEQ ID NO: 5, or derived from a scFv with an amino acid sequence as shown in SEQ ID NO: 6.

In some embodiment, said VEGF binding moiety comprises an antibody with a light chain amino acid sequence that is at least 95% identical to that of SEQ ID NO: 4, and heavy chain amino acid sequence that is at least 99% identical to that of SEQ ID NO: 7.

In some embodiment, said Ang-2 antagonist peptide is fused to one or both of the N-terminals of the heavy chains (HC) of the said antibody optionally through a peptide linker. In some embodiment, the peptide-HC fusion polypeptide comprises an amino acid sequence that is at least 99% identical as one selected from SEQ ID NOS:29, 30, and SEQ ID NO:33.

In some embodiment, said Ang-2 antagonist peptide is fused to one or both of the C-terminal of the heavy chain of the said antibody optionally through a peptide linker. In some embodiment, the Ang-2 antagonist peptide-heavy chain fusion polypeptide comprises an amino acid sequence that is at least 99% identical or 100% identical as one selected from SEQ ID NOS: 31, 32, and 34.

In some embodiment, said Ang-2 antagonist polypeptide is fused to the N-terminals or the C-terminals of the heavy chain of said antibody through a peptide linker; and wherein the Ang-2 antagonist peptide-heavy chain fusion polypeptide comprises an amino acid sequence at least 99% identical or 100% identical as one selected from SEQ ID NO: 37, 39, 41, 43, 45, 47, 49, 51, and 53.

In some embodiment, said VEGF binding moiety is an Fab with a light chain amino acid sequence of at least 95% identity to SEQ ID NO: 4, and a heavy chain amino acid sequence of at least 95% identity to SEQ ID NO: 5.

In some embodiment, the Ang2 antagonist peptide is fused to the N-terminal of the heavy chain of said Fab molecule through a peptide linker. In some embodiment, the Ang2 antagonist peptide-heavy chain fusion polypeptide has an amino acid sequence at least 99% identical as that of SEQ ID NO:19 or SEQ ID NO:20.

In some embodiment, the Ang-2 antagonist peptide is fused to the C-terminal of the heavy chain of said Fab molecule through a peptide linker. In some embodiment, the peptide-heavy chain fusion polypeptide has an amino acid sequence at least 99% identical as that of SEQ ID NO: 25 or SEQ ID NO:26.

In some embodiment, said VEGF binding moiety is an scFv with an amino acid sequence that has at least 95% identity to SEQ ID NO: 6. In some embodiment, the Ang-2 antagonist peptide is fused to the N-terminal of the scFv; and wherein the peptide-scFv fusion has an amino acid sequence selected from SEQ ID NOS:21 and 22. In some embodiment the Ang-2 antagonist peptide is fused to the C-terminal of the scFv; and wherein the peptide-scFv fusion polypeptide has an amino acid sequence selected from SEQ ID NO:27 and SEQ ID NO:28.

In some aspect, said chimeric molecule comprises a fusion protein that has one or more VEGF-binding moieties and one or two Ang-2 antagonist peptides, wherein said VEGF binding moiety is a VEGF trap with an amino acid sequence having at least 95% identity to SEQ ID NO: 3; wherein said chimeric molecule comprises two identical polypeptide chains, which have an amino acid sequence at least 99% identical as one selected from SEQ ID NOS:15-17, 23 and 24.

Also disclosed is a polynucleotide or polynucleotides encoding any one of the above said chimeric molecules. In some embodiment, said polynucleotide comprises a DNA sequence as one selected from SEQ ID NO: 35, 36, 38, 40, 42, 44, 46, 48, 50, 52, 54 and 56.

Also disclosed is an expression vector or vectors comprising the above said polynucleotide or polynucleotides.

Also disclosed is a host cell comprising the above said vector(s).

Also disclosed is a method of making any one of the above said chimeric molecules, comprising culturing the above said host cell under conditions that allow expression of the chimeric molecule, and isolating the chimeric molecule.

Also disclosed is a pharmaceutical composition comprising the chimeric molecule of any one of the above said chimeric molecule and a pharmaceutically acceptable excipient.

Further provide is a method of treating a patient with cancer, proliferative retinopathy, wet age-related macular degeneration (wAMD), macular edema following retinal vein occlusion (RVO), diabetic macular edema (DME), or diabetic retinopathy (DR) comprising administering to a subject of above said pharmaceutical composition.

BRIEF DESCRIPTION OF THE DRAWINGS

FIG. 1. Protein A Affinity Chromatography. Approximately 150 ml of the clarified HEK 293 cell culture medium of the transient expression of AMD-B was loaded to a Protein A column (1×17 cm (Diameter×Height) of Captiv A Protein A resin) at 3 ml/min. The protein A column was equilibrated with an equilibration buffer (25 mM Tris Buffer, 100 mM NaCl, PH approximately 7.2). The column was washed with the Equilibration buffer and eluted with 2 M ariginine solution, PH 4.

FIG. 2. Kinetics of Ang-1 or Ang-2 Binding to AMD-E As Analyzed by Octet Red96.

FIG. 3. Binding of AMD A-E with VEGF.

FIG. 4A. Blocking of Binding of Ang-1 and Ang-2 to Tie-2 by AMD-A and AMD-B

FIG. 4B. Blocking of Binding of Ang-1 and Ang-2 to Tie-2 by AMD-C and AMD-D

FIG. 5. Blocking of Binding of Ang-2 to Tie-2 by ASKB712-O and ASKB712-O2

DETAILED DESCRIPTION OF THE INVENTION

Disclosed herein are fusion proteins and chimeric molecules which comprise two components: an Ang-2 antagonist peptide operationally linked to a VEGF binding domain, which is selected from an anti-VEGF antibody, an anti-VEGF Fab, an anti-VEGF scFv, or a VEGF receptor extracellular domain-Fc fusion protein (or VEGF Trap). The Ang-2 antagonist peptide and VEGF binding domain are each defined below with reference to percent identity to a reference sequence. Further disclosed are methods of using said chimeric molecules to treat a patient of cancer, proliferative retinopathy, neovascular glaucoma, macular edema, wet age-related macular degeneration (wAMD), macular edema following retinal vein occlusion (RVO), diabetic macular edema (DME), or diabetic retinopathy (DR).

It is understood that aspects and variations of the invention described herein include "consisting" and/or "consisting essentially of" aspects and variations.

Definitions

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X." Additionally, use of "about" preceding any series of numbers includes "about" each of the recited numbers in that series. For example, description referring to "about X, Y, or Z" is intended to describe "about X, about Y, or about Z."

The term "antigen-binding moiety" refers to a polypeptide or a set of interacting polypeptides that specifically bind to an antigen, and includes, but is not limited to, an antibody or antibody fragment, such as a monoclonal antibody, polyclonal, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies, a single chain antibody, and a Fc-containing polypeptide, such as an immunoadhesion. In some embodiments, the antibody may be of any heavy chain isotype (e.g., IgG, IgA, IgM, IgE, or IgD). In some embodiments, the antibody may be of any light chain isotype (e.g., kappa or gamma). The antibody may be non-human (e.g., from mouse, goat, or any other animal), fully human, humanized, or chimeric. In some embodiments, the antibody is a derivatized antibody.

The term "effective amount" used herein refers to an amount of a compound or composition sufficient to treat a specified disorder, condition, or disease, such as ameliorate, palliate, lessen, and/or delay one or more of its symptoms. In reference to a disease such as a cancer, an effective amount comprises an amount sufficient to cause a tumor to shrink and/or to decrease the growth rate of the tumor (such as to suppress tumor growth) or to prevent or delay other unwanted cell proliferation in the cancer. In some embodiments, the effective amount is an amount sufficient to delay development of a cancer. In some embodiments, the effective amount is an amount sufficient to prevent or delay recurrence. An effective amount can be administered in one or more administrations. In the case of a cancer, the effective amount of the drug or composition may: (i) reduce the number of epithelioid cells; (ii) reduce tumor size; (iii) inhibit, retard, slow to some extent and preferably stop the cancer cells infiltration into peripheral organs; (iv) inhibit (e.g., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "fused" or "fusion" in reference to two or more polypeptide sequences (such as an antibody heavy chain, antibody light chain, an antibody heavy chain fragment, an antibody light chain fragment, a drug conjugation moiety, a heterologous peptide, an albumin, or an albumin fragment) refers to joining of the polypeptide sequences through a backbone peptide bond.

The term "pharmaceutically acceptable" when used to refer to a compound or composition means that the compound or composition is suitable for administration to a subject, including a human subject, to achieve the treatments described herein, without unduly deleterious side effects in light of the severity of the disease and necessity of the treatment.

The term "subject" refers to a mammal and includes, but is not limited to, human, bovine, horse, feline, canine, rodent, or primate.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from a disease, diminishing the extent of a disease, stabilizing a disease (e.g., preventing or delaying the worsening of the disease), preventing or delaying the spread (e.g., metastasis) of a disease, preventing or delaying the recurrence of a disease, delaying or slowing the progression of a disease, ameliorating a disease state, providing remission (partial or total) of a disease, decreasing the dose of one or more other medications required to treat a disease, delaying the progression of a disease, increasing the quality of life, and/or prolonging survival. Also encompassed by "treatment" is a reduction of a pathological consequence of a disease (such as cancer). The methods of the invention contemplate any one or more of these aspects of treatment.

It is to be understood that one, some or all of the properties of the various embodiments described herein may be combined to form other embodiments of the present invention.

The section headings used herein are for organizational purposes only and are not to be construed as limiting the subject matter described.

Ang-2 Antagonist Peptide

The fusion protein or chimeric molecule comprises an Ang-2 antagonist peptide component, which binds to Angiopoietin 2 (Ang-2) and inhibits the binding of Ang-2 to its receptor. One example of the peptide is called 2×Con4 (C), as described in WO2004/092215A2 or WO03/05134A2. 2×Con4(C) has an amino acid sequence as shown in SEQ ID NO: 1. Additional examples of Ang-2 binding peptides include but are not limited to: L-1-21, L1-7, L1-10, and L1-15, as described in WO2004/092215A2. Examples of Ang-2 antagonist peptides are shown in SEQ ID NO: 8-14.

VEGF-Binding Moiety

The chimeric molecule further comprises a VEGF-binding moiety. In one embodiment, said VEGF-binding moiety is an anti-VEGF antibody, an anti-VEGF Fab, or an anti-VEGF scFv that inhibits the binding of VEGF to its receptors. One example of the VEGF antibody is bevacizumab, which has two heavy chains with amino acid sequence as shown as SEQ ID NO:1, and two light chains with amino acid sequence as shown as SEQ ID NO:2. Another example is ranibizumab, an anti-VEGF Fab. And a third example is Brolucizumab (RTH258), which is a humanized single-chain antibody fragment (scFv) against VEGF.

In another embodiment, said VEGF binding domain is a VEGF receptor-Fc fusion protein which "traps" VEGF (herein, referred to as a "VEGF trap") and competes with the naturally occurring VEGF cellular receptor to inhibit VEGF. One example of the VEGF-receptor Fc fusion protein is afilbercept, which has an amino acid sequence as shown in SEQ ID NO:3.

In some embodiments, the VEGF-binding moiety comprises the six complementarity determining regions (CDRs) of Brolucizumab (RTH258), Ranibizumab or Bevacizumab. A number of CDR delineations are known in the art and are encompassed herein. A person of skill in the art can readily determine a CDR for a given delineation based on the sequence of the heavy or light chain variable region. The "Kabat" Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). "Chothia" CDRs refer to the location of the structural loops (Chothia & Lesk, *Canonical* structures for the hypervariable regions of immunoglobulins, J. Mol. Biol., vol. 196, pp. 901-917 (1987)). The "AbM" CDRs represent a compromise between the Kabat CDRs and Chothia structural loops, and are used by Oxford Molecular's AbM antibody modeling software. The "Contact" CDRs are based on an analysis of the available complex crystal structures. The residues from each of these CDRs are noted below in Table 1, in reference to common antibody numbering schemes. Unless otherwise specified herein, amino acid number of antibodies refers to the Kabat numbering scheme as described in Kabat et al., supra, including when CDR delineations are made in reference to Kabat, Chothia, AbM, or Contact schemes. Using this numbering system, the actual linear amino acid sequence may contain fewer or additional amino acids corresponding to a shortening of, or insertion into, a framework region (FR) or CDR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

TABLE 1

CDR Delineations According to Various Schemes

| CDR | Kabat | AbM | Chothia | Contact |
|---|---|---|---|---|
| VL-CDR1 | L24-L34 | L24-L34 | L26-L32 | L30-L36 |
| VL-CDR2 | L50-L56 | L50-L56 | L50-L52 | L46-L55 |
| VL-CDR3 | L89-L97 | L89-L97 | L91-L96 | L89-L96 |
| VH-CDR1 (Kabat Numbering) | H31-H35B | H26-H35B | H26-H32 | H30-H35B |
| VH-CDR1 (Chothia Numbering) | H31-H35 | H26-H35 | H26-H32 | H30-H35 |
| VH-CDR2 | H50-H65 | H50-H58 | H53-H55 | H47-H58 |
| VH-CDR3 | H95-H102 | H95-H102 | H95-H101 | H93-H101 |

In some embodiments, the CDRs are "extended CDRs," and encompass a region that begins or terminates according to a different scheme. For example, an extended CDR can be as follows: L24-L36, L26-L34, or L26-L36 (VL-CDR1); L46-L52, L46-L56, or L50-L55 (VL-CDR2); L91-L97 (VL-CDR3); H47-H55, H47-H65, H50-H55, H53-H58, or H53-H65 (VH-CDR2); and/or H93-H102 (VH-CDR3).

Ang-2 Antagonist Peptide-VEGF-Binding Moiety Fusion Protein

The Ang-2 peptide can be linked or fused to either the C- or N-terminus of the VEGF antibody (e.g., either the heavy or the light chains) or the VEGF receptor-Fc fusion protein. The Fc portion of the VEGF receptor-Fc fusion protein may be located at either the C- or N-terminus of the VEGF receptor protein. The Fc portion is further defined herein.

The present compositions include "Fc fragments" or "Fc regions." The term "Fc fragment" or "immunoglobulin Fc region" as used herein, refers to a protein that contains at least the heavy-chain constant region 2 (CH2) and the heavy-chain constant region 3 (CH3) of an immunoglobulin. In one embodiment, the Fe region excludes the variable regions of the heavy and light chains, the heavy-chain constant region 1 (CH1) and the light-chain constant region 1 (CL1) of the immunoglobulin. The Fc region may further include a hinge region at the heavy-chain constant region.

Also, the immunoglobulin Fc region disclosed herein may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, the immunoglobulin Fc region may be a fragment having a deletion in a relatively long portion of the amino acid sequence of CH2 and/or CH3. That is, the immunoglobulin Fc region disclosed herein may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region disclosed herein includes a native amino acid sequence, or a sequence analogue thereof. An amino acid sequence analogue is a sequence that is different from the native amino acid sequence due to a deletion, an insertion, a non-conservative or conservative substitution or combinations thereof of one or more amino acid residues.

Also, other various analogues are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence analogues of the immunoglobulin Fc region are disclosed in WO 1997/034631 and WO 1996/032478.

The aforementioned Fc analogues are analogues that have a biological activity identical to the Fc region disclosed herein or improved structural stability, for example, against heat, pH, or the like.

In addition, these Fc regions may be obtained from native forms isolated from humans and other animals including cows, goats, pigs, mice, rabbits, hamsters, rats and guinea pigs, or may be recombinants or analogues thereof, obtained from transformed animal cells or microorganisms. Herein; they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c. In another embodiment, a human-derived Fc region is a recombinant immunoglobulin Fc region that is obtained from a microorganism.

In one embodiment, the Fc region, if desired, may be modified by phosphorylation, sulfation, acrylation, glycosylation, methylation, farnesylation, acetylation, amidation, and the like. In one embodiment, the immunoglobulin Fc region disclosed herein may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable as a drug carrier.

As used herein, the term "deglycosylation" refers to enzymatically removing sugar moieties from an Fc region, and the term "aglycosylation" means that an Fc region is produced in an unglycosylated form by a prokaryote, preferably E. coli.

In one embodiment, the immunoglobulin Fc region may be an Fc region that is derived from IgG, IgA, IgD, IgE and IgM, or that is made by combinations thereof or hybrids thereof. In an embodiment, it is derived from IgG or IgM, which are among the most abundant proteins in human blood, and further, wherein an IgG, which is known to enhance the half-lives of ligand-binding proteins is an IgG1, IgG2a, IgG2b and/or IgG3.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

Pharmaceutical Compositions

Pharmaceutical compositions of the chimeric molecules are prepared by mixing the antibody fusion molecules or the antibody fusion molecule drug conjugate having the desired degree of purity with one or more optional pharmaceutically acceptable carriers (see *Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof, such as citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount between 0.1% to 25% by weight, or more preferably between 1% to 5% by weight, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

The choice of pharmaceutical carrier, excipient or diluent may be selected with regard to the intended route of administration and standard pharmaceutical practice. Pharmaceutical compositions may comprise as—or in addition to—the carrier, excipient or diluent any suitable binder(s), lubricant(s), suspending agent(s), coating agent(s) or solubilizing agent(s).

There may be different composition/formulation requirements dependent on the different delivery systems. By way of example, pharmaceutical compositions useful in the present invention may be formulated to be administered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be administered by a number of routes. In some embodiment, said formulation is administrated directly in a tumor or tumors.

In an embodiment, a host cell is a cell that is transfected with an expression vector containing a nucleotide or polynucleotide sequence that encodes one or more protein sequences that can be expressed in a cell. In an embodiment, a cell, including a host cell is a mammalian cell, a yeast cell, an insect cell, or a bacteria. In a further embodiment, a mammalian cell used as a host cell can be a Chinese hamster ovary ("CHO") cell, a HeLa cell, an HEK cell, including an HEK-293 cell. In another embodiment, a yeast cell used as a host cell can be *S. cerevisiae* or *Pichia pastoris*. In an embodiment, an insect cell used as a host cell can be Sf9, Sf21, Hi-5, Schneider 2 cells, Schneider 3 cells or High Five. In a further embodiment, a bacterial cell used as a host cell can be *E. coli, Corynebacterium* or *C. glutamicum*.

In some embodiments, an antibody or protein formulation is a lyophilized formulation. In another embodiment, an antibody or protein formulation is an aqueous formulation.

In other aspects of this embodiment, a fusion protein or chimeric molecule disclosed herein reduces the severity of a disease by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a fusion protein or chimeric molecule disclosed herein reduces the severity of a disease from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A fusion protein or chimeric molecule disclosed herein may comprise a therapeutic compound in an amount sufficient to allow customary administration to an individual and with other excipients may constitute a pharmaceutical composition. In aspects of this embodiment, a therapeutic compound disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects of this embodiment, a therapeutic compound disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a therapeutic compound disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a therapeutic compound disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A therapeutic compound disclosed herein may comprise a solvent, emulsion or other diluent in an amount sufficient to dissolve a therapeutic compound disclosed herein. In other aspects of this embodiment, a therapeutic compound disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a therapeutic compound disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic compound disclosed herein in a pharmaceutical composition disclosed herein may be of any concentration desired. In an aspect of this embodiment, the final concentration of a therapeutic compound in a pharmaceutical composition may be a therapeutically effective amount. In other aspects of this embodiment, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, treating an individual suffering from a disease, including a cancer. As used herein, the term "treating," refers to reducing or eliminating in an individual a clinical symptom of cancer; or delaying or preventing in an individual the onset of a clinical symptom of a disease, including a cancer. For example, the term "treating" can mean reducing a symptom of a condition characterized by a cancer, including, but not limited to, tumor size, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with cancer are well known and can be determined by a person of ordinary skill in the art by taking into account factors, including, without limitation, the location of the disease, including a cancer, the cause of the disease, including a cancer, the severity of the disease, including a cancer, and/or the tissue or organ affected by the disease, including a cancer. Those of skill in the art will know the appropriate symptoms or indicators associated with a specific type of disease, including a cancer and will know how to determine if an individual is a candidate for treatment as disclosed herein.

In aspects of this embodiment, a therapeutically effective amount of a therapeutic compound disclosed herein reduces a symptom associated with a disease, including a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a disease, including a cancer by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a disease, including a cancer by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of a therapeutic compound disclosed herein typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

Dosing can be single dosage or cumulative (serial dosing), and can be readily determined by one skilled in the art. For instance, treatment of a disease, including a cancer may comprise a one-time administration of an effective dose of a therapeutic compound or a pharmaceutical composition disclosed herein. Alternatively, treatment of a disease, including a cancer may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a therapeutic compound or pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a therapeutic compound or pharmaceutical composition disclosed herein that is administered can be adjusted accordingly.

In one embodiment, a therapeutic compound disclosed herein is capable of reducing the number of cancer cells or tumor size in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a therapeutic compound is capable of reducing the number of cancer cells or tumor size in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, a therapeutic compound and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects, of this embodiment, a therapeutically effective amount of a therapeutic compound disclosed herein reduces or maintains a disease, including a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces or maintains a disease or a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces or maintains a disease, including a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

A pharmaceutical composition or therapeutic compound is administered to an individual. An individual is typically a human being, but can be an animal, including, but not limited to, dogs, cats, birds, cattle, horses, sheep, goats, reptiles and other animals, whether domesticated or not. Typically, any individual who is a candidate for treatment is a candidate with some form of disease, including a cancer, whether the cancer is benign or malignant, a tumor, solid or otherwise, a cancer cell not located in a tumor or some other form of cancer. Among the most common types of cancer include, but are not limited to, bladder cancer, breast cancer, colon and rectal cancer, endometrial cancer, kidney cancer, renal cancer, leukemia, lung cancer, melanoma, non-Hodgkins lymphoma, pancreatic cancer, prostate cancer, stomach cancer and thyroid cancer. Pre-operative evaluation typically includes routine history and physical examination in addition to thorough informed consent disclosing all relevant risks and benefits of the procedure.

EXAMPLES

Example 1—Production of the Chimeric Molecule Comprising VEGF Antibody and Ang-2 Binding Peptide in HEK293 Cells Chimeric molecules named AMD A, B, C, D and E (see Table 2) were expressed through transient expression by HEK-293 cells. Briefly, DNAs (SEQ ID NOs: 58, 59, 60 and 63) for the fusion proteins comprising VEGF antibody light chain with or without Ang2 binding peptides and DNAs (SEQ ID NOs: 57, 61 and 62) for the fusion proteins comprising VEGF antibody heavy chain with Ang2 binding peptides were synthesized and cloned into expression vectors. The complete expression constructs comprising the genes were confirmed by DNA sequencing. DNA constructs were transformed into *E. coli* DH5alfa competent cells (Invitrogen). Single clone was selected and cultured in LB broth with antibiotics (kanamycin, 25 ug/mL). DNA plasmids were extracted with Qiagen Plasmid Maxi Kit (Qiagen) following manufacture's protocol. Plasmid concentration was measured by NanoDrop (Thermo Fisher). The expression plasmid constructs containing the DNA sequences encoding the genes of interest, were introduced into HEK-293 cells transiently by using polyethylenimine (PEI). The transfected cells were treated by alproic acid (VPA) 24 hours post transfection to enhance protein expression.

TABLE 2

AMD Molecules

| | AMD-A | AMD-B | AMD-C | AMD-D | AMD-E |
|---|---|---|---|---|---|
| Light Chain | Peptide L1-15 (No LE*) fused to N-terminus of Bevacizumab light chain | Bevacizumab light chain | Peptide L1-15 (with LE) fused to N-terminus of Bevacizumab light chain | Bevacizumab light chain | Bevacizumab light chain |
| Light Chain DNA SEQ ID NO | SEQ ID NO: 59 (LY2.55.1) | SEQ ID NO: 63 (LY2.55.5) | SEQ ID NO: 60 (LY2.55.2) | SEQ ID NO: 63 (LY2.55.5) | SEQ ID NO 58 (DHAMDL 083016) |
| Heavy Chain | Peptide L1-15 (No LE) fused to N-terminus of Bevacizumab heavy chain | Peptide L1-15 (No LE) fused to N-terminus of Bevacizumab heavy chain | Peptide L1-15 (with LE) fused to N-terminus of Bevacizumab heavy chain | Peptide L1-15 (with LE) fused to N-terminus of Bevacizumab heavy chain | Peptide 2xCon4(C) fused to the C-terminus of the Heavy Chain of Bevacizumab |
| Heavy Chain DNA SEQ ID NO | SEQ ID NO: 61 (LY2.55.3) | SEQ ID NO: 61 (LY2.55.3) | SEQ ID NO: 62 (LY2.55.4) | SEQ ID NO: 62 (LY2.55.4) | SEQ ID NO 57 (DHAMDH 02083016) |

*LE is one of the flanking sequences, which were present both in the original phage clone when the peptides were screened and in the subsequent peptibody (Peptide-Fc fusion) molecules.

After approximately 6 days of culturing, the cell culture media were harvested by clarifying centrifugation at 9000 rpm for 30-60 minutes followed by filtration through 0.22 micrometer filters. The clarified supernatants were loaded to a Protein A affinity column and the chimeric molecules (AMD-A, B, C, D and E) were purified. The chimeric molecules were eluted using 2 M arginine solution, pH 4 from the protein A column. FIG. 1 shows a representative chromatograph of the Protein A column step. Table 3 summarizes the results from the purification of the chimeric molecules. As shown in Table 3, chimeric molecules containing a total of 2 copies L1-15 peptides (AMD-B and AMD-D), both fused to the N-terminals of the heavy chain, had significantly higher expression levels comparing to the ones with a total of four copies of L1-15 peptides (AMD-A and AMD-C), wherein there is one each of L1-15 peptide fused to the N-terminals of both the light chains and the heavy chains of the antibody. With or without the flanking sequence LE as part of the L1-15 peptide did not appear to affect the expression of the chimeric molecules.

The expression level of AMD-E was comparable to that of AMD-B and AMD-D (Table 3). AMD-E has one Peptide 2×Con4(C) fused to each of the C-terminus of the heavy chains of Bevacizumab. The purity of the products were analyzed using SDS electrophoresis and/or HPLC methods.

TABLE 3

Summary of Protein A Affinity Chromatography Purification

| | AMD-A | AMD-B | AMD-C | AMD-D | AMD-E |
|---|---|---|---|---|---|
| Approximate culture volume (ml) | 150 | 200 | 150 | 150 | 200 |
| Protein A Pool Volume (ml) | 3 | 9 | 5 | 12 | 17 |
| OD280 | 0.24 | 1.14 | 0.29 | 0.88 | 0.80 |
| Approximate amount in the Protein A Pool, (mg) | 0.45 | 6.4 | 0.91 | 6.6 | 8.5 |

Example 2—Production of the Chimeric Molecule Comprising VEGF Trap and Ang2 Binding Peptide in CHO Cells DNA for the chimeric molecule comprising the VEGF Receptor-Fc fusion protein (VEGF Trap) and the Ang-2 binding peptide (SEQ ID NO: 64, named as ASKB-E06) is synthesized and cloned into an expression vector. The complete expression construct comprising the DNA gene is confirmed by DNA sequencing. The expression construct is amplified by transforming into DH10B *E. coli* and culturing the cells overnight. DNA for the expression construct was prepared and purified by endo-free plasmid kit (from QIAGEN®).

Cell lines stably expressing ASKB-E06 is obtained by transfecting the expression construct into GS$^{-/-}$ Chinese hamster ovarian cells (CHO) by electroporation and screening for transfected CHO cells using a selective culture medium without glutamine (EX-CELL® CD CHO Fusion Growth Medium). In this manner 32 or more stable mini-pools are established and the leading mini-pool is selected based on expression level in batch and fed-batch cultures. The expression levels are detected by ELISA titer assay. Single cloning is performed by limited dilution and using clone media, two leading single clones out of more than 100 positive clones are selected based on productivity and cell growth in batch and fed-batch culture. The lead clones are expanded and seeded at $0.5 \times 10^6$ cells/mL, total 300 mL in 2 L shake flasks, and the cells are cultured at 37° C., 5% $CO_2$, 70% HMR conditions and shaking at 120 rpm. The cultures are fed by using 5% Acti CHO® Feed A+0.5% Feed B (from GE Health) on Day 3, 6, 7, 8 and 9. The cell viability, viable cell density are monitored every other day, the cultures are harvested on Day 11-13.

The cell culture medium is harvested by clarifying approximately 600 mL of the cultured cell medium through centrifugation at 2000 rpm for 10 minutes followed by filtration. The clarified supernant is loaded to a Protein A affinity column and the chimeric molecule is purified. The protein is further purified using ion exchange chromatography, hydrophobic interaction chromatography, hydroxyapatite chromatography, and/or mixed mode chromatography. The product is further concentrated and buffer exchanged using UFDF and further formulated. The purity of the product is analyzed using CE-SDS and HPLC methods.

Example 3—Molecular Assays to Evaluate Dual Antagonist Activities of the Chimeric Molecules Molecular assays (Octet Binding Affinity, Affinity ELISA, and Blocking ELISA) were developed to assess direct binding of the chimeric molecules to ANG-1, Ang-2 and/or VEGF, and the effect of the chimeric molecules on the Ang1:Tie-2 interaction, Ang-2:Tie-2 interaction and/or VEGF:VEGF receptor interaction. These in vitro assays are described as the following: Octet Affinity Purified recombinant human VEGF protein was ordered from Life-Technologies (Cat. #PHC9391). Human Ang1 or Ang2 protein were ordered from R&D System. Analysis was carried out using Octet Red96 from Pall ForteBio. Using anti-human IgG Fc sensors, a sample of chimeric molecule AMD-B, AMD-D, AMD-E or the control antibody Bevacizumab was loaded for 300 seconds at 3 ug/mL in the kinetics buffer. Ligands ANG1, ANG2, or VEGF samples were associated for 300 seconds using a dilution series starting at 5 or 10 ug/mL and sequentially diluting 2-fold for 7 wells. Dissociation was run for 600 seconds. Data was analyzed using a 1:1 model with global fit. A representative binding kinetics graph is shown in FIG. 2. The binding affinity results are summarized in Tables 4A, 4B and 4C. The results showed that the chimeric molecules. AMD-B, AMD-D, and AMD-E were able to bind to Ang1, Ang2, and VEGF. It was also noticed that the chimeric molecule AMD-B with four L1-15 peptides fused to the N-terminals of the antibody had reduced affinity to VEGF when comparing to the control antibody Bevacizumab. AMD-D and AMD-E showed comparable affinity to VEGF comparing to the control antibody ASKB1202, a biosimilar m An internal control, ASKB 1202, a biosimilar to Bevacizumab developed in-house.

TABLE 4A

Summary of the Octet Affinity analysis results - Binding of ANG-1.

| | kon (1/Ms) | koff (1/s) | KD (M) |
|---|---|---|---|
| AMD-B | 1.56E+05 | 2.69E−04 | 1.73E−09 |
| AMD-D | 1.75E+05 | 2.41E−04 | 1.37E−09 |
| AMD-E | 9.42E+04 | 1.01E−04 | 1.07E−09 |

TABLE 4B

Summary of the Octet Affinity analysis results - Binding of ANG-2.

|  | kon (1/Ms) | koff (1/s) | KD (M) |
|---|---|---|---|
| AMD-B | 3.34E+04 | 4.33E−05 | 1.30E−09 |
| AMD-D | 3.68E+04 | 2.39E−05 | 6.49E−10 |
| AMD-E | 3.54E+04 | 5.52E−05 | 1.56E−09 |

TABLE 4C

Summary of the Octet Affinity analysis results - Binding of VEGF.

|  | kon (1/Ms) | koff (1/s) | KD (M) |
|---|---|---|---|
| Bevacizumab | 8.03E+04 | <1.0E−07 | <1.0E−12 |
| AMD-B | 1.41E+05 | 3.42E−05 | 2.42E−10 |
| AMD-D | 1.01E+05 | <1.0E−07 | <1.0E−12 |
| AMD-E | 1.38E+05 | <1.0E−07 | <1.0E−12 |

Affinity ELISA: Purified recombinant human VEGF protein was ordered from Life-Technologies (Cat. #PHC9391). VEGF is reconstituted in BSA solution at 0.1 mg/mL as recommended by the manufacturer. Aliquots the samples were made and stored at −20° C.

Using microtiter plates, approximately 100 microliters per well of VEGF is added to each well and the plates were incubated about 2 hours, after which the plates are washed with phosphate buffered saline (PBS) containing about 0.1 percent Tween-20 four times. The wells are then blocked using about 250 microliters per well of about 5 percent BSA in PBS, and the plates were incubated at room temperature for about 2 hours. After incubation, excess blocking solution is discarded, and about 100 microliters of AMD-A, B, C, D or E was added to a well in a dilution series starting at a concentration of about 40 nanomolar and then serially diluting 4-fold in PBS containing about 1 percent BSA. The plates were then incubated overnight at room temperature. After incubation, plates were washed with PBS containing about 0.1 percent Tween-20. Washing was repeated four additional times, after which about 100 microliters per well of goat anti-human IgG(Fc)-HRP (Pierce Chemical Co., catalog #31416) previously diluted 1:5000 in PBS containing 1 percent BSA was added. Plates were incubated approximately 1 hour at room temperature. Plates were then washed five times in PBS containing about 0.1 percent Tween-20, after which about 100 microliters per well of TMB (3,3',5,5'-Tetramethylbenzidine Liquid Substrate System; Sigma Chemical Company, St. Louis, Mo., catalog number T8665) substrate was added and plates are incubated about 5-15 minutes until blue color developed. Absorbance was then read in a spectrophotometer at about 450 nm.

FIG. 3 shows the ELISA results of binding of VEGF to AMD-A, B, C, D, and E. An internal control, ASKB 1202, a biosimilar to Bevacizumab currently in development, was used as a positive control. The results showed that all the molecules AMD-A, B, C, D and E retained abilities to bind to VEGF. The EC-50 results are summarized in Table 5. The results showed that the AMD-B and AMD-D had VEGF binding affinity close to ASKB1202. In addition, AMD-B and AMD-D had stronger VEGF binding affinity than AMD-A and AMD-C.

TABLE 5

Affinity ELISA Results: Binding of VEGF to AMD-A, B, C, D and E.

|  | EC-50 (ng/ml) |
|---|---|
| AMD-A | 2.296 |
| AMD-B | 1.278 |
| AMD-C | 3.328 |
| AMD-D | 1.247 |
| AMD-E | 1.87 |
| ASKB1202 | 0.8002 |

Blocking ELISA:

The chimeric molecules were assessed in their abilities in blocking the binding of Ang1 and Ang2 to their receptor Tie-2. 96 well microtiter plate (Nunk) was coated with 100 uL final concentration 100 ng/mL of human Tie2-Fc (R&D System, 313-T1) diluted in 0.1 M carbonate (pH9.3) at 4° C. overnight. The plate was then blocked for 2 hours with 5% BSA in PBST (0.05% Tween 20). Purified chimeric molecule, at starting concentration of 1000 ng/mL, was serially diluted with dilution factor of three in PBS with 1% BSA. Human Ang1 or Ang2 protein (R&D System) was added to final concentration of 50 ng/mL and incubated at room temperature for 1 hour. The Chimeric molecule-Ang1 or Chimeric molecule-Ang2 mixture was then added into microtiter plate coated with human Tie2-Fc and incubate for another 1 hour at room temperature. 100 uL anti-Ang1 or anti-Ang2 monoclonal antibody (R&D System) was added into each well at final concentration of 1 ug/mL and incubated for 1 hour at room temperature. Horseradish-peroxidase (HRP) conjugated anti-mouse IgG secondary antibody was added at 1:5000 dilution and incubated for 1 hour at room temperature. Standard colorimetric response was developed by using TMB (Pierce). Absorbance was read at OD450 by spectrophotometer. Between each step, the plate was washed 5 time with 100 uL PBS.

The dose dependent inhibition or lack of inhibition of the binding of Ang1 and Ang-2 to receptor Tie-2 are shown in FIG. 4. The IC-50 results are summarized in Table 6. The results showed that the chimeric molecules AMD-A, B, C, and D selectively inhibited the binding of Ang2 to Tie-2, with IC-50 in the range of 5-15 ng/ml; while their abilities in inhibiting the binding of Ang-1 to Tie-2 were very weak, if any, despite the fact that they all were able to bind to Ang1. The results also showed that AMD-A and AMD-C, both comprising 4 copies of the peptide L1-15 had lower IC-50 than AMD-B and AMD-D. AMD-E was able to inhibit the association of both Ang-1 and Ang-2 to their receptor Tie-2.

FIG. 5 shows the inhibition of the binding of Ang-2 to Tie-2 by chimeric molecules 712-O and 712-O2. The chimeric molecule 712-O comprises two heavy chain polypeptide chains with an amino acid sequence as shown in SEQ ID NO: 29 and two light chains with an amino acid sequence as shown in SEQ ID NO: 4. The chimeric molecule 712-O2 comprises two heavy chain polypeptide chains with an amino acid sequence as shown in SEQ ID NO: 31 and two light chains with an amino acid sequence as shown in SEQ ID NO: 4.

The Ang-2 antagonist peptide L1-15 is fused to the N-terminals of the heavy chains of a VEGF-binding antibody in the case of 712-O. In the case of 712-O2, L1-15 is fused to the C-terminals of the heavy chains. The IC-50's for the Ang-2 blocking assay were approximately 33 pM for 712-O and approximately 78 pM for 712-O2. Since L1-15, together with other peptides including L1-7, L1-10 and L1-21, was considered an N-terminal fusion peptide and was only tested to be active when it is fused to the N-terminal of the Fc as described in WO2004/092215A2. It was surprised that the chimeric molecule 712-O2 was significantly potent with an IC-50 of approximately 78 pM.

TABLE 6

Blocking ELISA Results: Inhibition of Binding of Ang-1 or Ang-2 to Tie-2.

| | IC-50 of inhibiting Ang-1 Binding (ng/ml) | IC-50 of Inhibiting Ang-2 Binding (ng/ml) |
|---|---|---|
| AMD-A | Not detected | 7.3 |
| AMD-B | Not detected | 12.49 |
| AMD-C | Not detected | 5.136 |
| AMD-D | Not detected | 15.21 |
| AMD-E | 10 (estimated) | 2.107 |

Example 4—Cell-Based Activity Assay: In Vitro Human Umbilical Vein Endothelial Cells (HUVEC) Tube-Formation Assay In order to confirm whether or not ASKB-E06 inhibits angiogenesis, proliferation, migration, and differentiation assays of human umbilical vein endothelial cells (HUVEC) are performed.

a) Proliferation Inhibition of HUVEC by 712-O

After 10,000 HUVEC were added to 100 µl of EBM-2 medium (Lonza, Switzerland), EBM-2 medium having VEGF-A (50 ng/ml) is added thereto, or EBM-2 medium including VEGF-A (50 ng/ml) and 712-O sample at different concentration is added thereto in each well of a 96-well plate, followed by incubation under 5% $CO_2$, at 37° C. for 72 hours. Then, 10 µl of WST-1 solution was added thereto, followed by incubation at 37° C. for 4 hours. Absorbance is measured at 410 nm with a reference of 610 nm. The results are shown in Table 7, which indicated that 712-O had similar or higher potency than Lucentis®. It was more potent than ASKB1202 (a biosimilar of bevacizumab).

TABLE 7

HUVEC Assay Results

| | Approximate MW (KD) | EC50 (nM) |
|---|---|---|
| 712-O (Lot# LL21-05) | 156 | 0.57 |
| ASKB1202 (Lot# DS20150403) | 149 | 1.28 |
| Lutenis ® | 48 | 0.72 |

(2) Migration Inhibition of HUVEC by 712-O

After a bottom of Transwells, (Corning Inc., US) having a pore size of 8-µm is coated with 0.1% gelatin and mounted in a 24-well plate, a lower chamber is filled with 600 µl of EBM-2 medium (Lonza), EBM-2 with VEGF-A (50 ng/ml), or EBM-2 with VEGF-A (50 ng/ml) and 712-O sample at different concentration. An upper chamber is provided with 100 µl of EBM-2 medium containing $1×10^5$HUVEC. After incubation in 37° C. cell incubator for 4 hours, a filter is detached from the Transwell and cells are fixed with methanol for 1 minute and stained with Hematoxylin/Eosin. Cells which do not migrate but are left on an upper surface of the transwell are completely removed with a cotton swab. Five random fields among the cells migrated through the filter are arbitrarily chosen under an optical microscope (×100) and the number thereof is counted.

(3) Inhibition of Tube Formation by 712-O

In order to confirm that ASKB-E06 can inhibit differentiation of HUVEC, tube formation assay is performed. More specifically, after a 96-well plate is coated with Growth Factor Reduced Matrigel (BD Biosciences, US), 15,000 HUVEC in 100 µl of EBM-2 medium, EBM-2 medium with VEGF-A (50 ng/ml), or EBM-2 medium with VEGF-A (50 ng/ml) and an antibody sample are added to each well, followed by incubation in 37° C. cell incubator for 6 hours. Then, tube formation is observed by using an inverted microscope.

Example 5—In Vivo Anti-Tumor Activity Study: Therapeutic Efficacy Studies with Systemically Administered Dual Antagonist Chimeric Molecules The chimeric molecule ASKB712-B is administered subcutaneously to A431 tumor-bearing mice at a once-per-day schedule 72 hours after tumor challenge. The doses used are 1000, 200, 40 and 8 ug/mouse/day. A total of 20 doses is given to all animals. Tumor volumes and body weights are recorded three times/week. At the end of the study, animals are sacrificed, and their sera are collected for measuring ASKB712-B levels by ELISA. Tumors and a panel of normal tissues are collected from all groups.

The non-limiting examples provided herein are for illustrative purposes only in order to facilitate a more complete understanding of the disclosed subject matter. These examples should not be construed to limit any of the embodiments described in the present specification, including those pertaining to the fusion peptides, pharmaceutical compositions, or methods and uses for treating cancer, proliferative retinopathies, AMD or RA.

A chimeric molecule, which comprises one or two VEGF-binding moieties and one or two Ang-2 antagonist peptides, wherein:
  a) said Ang-2 antagonist peptide comprises an amino acid sequence selected from SEQ ID NO: 8-14; and
  b) said VEGF-binding moiety is an antibody, an Fab or an scFv; and wherein said antibody, Fab or scFv comprises light chain CDRs as derived from a light chain with an amino acid sequence as shown in SEQ ID NO: 4, or derived from a scFv with an amino acid sequence as shown in SEQ ID NO: 6, and heavy chain CDRs as derived from a heavy chain with an amino acid sequence as shown in SEQ ID NO: 5, or derived from a scFv with an amino acid sequence as shown in SEQ ID NO: 6.

The chimeric molecule of claim 1, wherein said VEGF binding moiety comprises an antibody with a light chain amino acid sequence that is at least 95% identical to that of SEQ ID NO: 4, and heavy chain amino acid sequence that is at least 99% identical to that of SEQ ID NO: 7.

The chimeric molecule of claim 2, wherein said Ang-2 antagonist peptide is fused to the N-terminal of the heavy chain (HC) of the said antibody optionally through a peptide linker.

The chimeric molecule of claim 3, wherein the Ang-2 antagonist peptide-HC fusion polypeptide comprises an amino acid sequence that has at least 99% identity to one of SEQ ID NOS:29, 30, and SEQ ID NO:33.

The chimeric molecule of claim 2, wherein said Ang-2 antagonist peptide is fused to the C-terminal of the heavy chain of the said antibody optionally through a peptide linker.

The chimeric molecule of claim 5, wherein the Ang-2 antagonist peptide-heavy chain fusion polypeptide comprises an amino acid sequence at least 99% identical or 100% identical as one selected from SEQ ID NOS: 31, 32, and 34.

The chimeric molecule of claim 2, wherein said Ang-2 antagonist polypeptide is fused to the N-terminals or the C-terminals of the heavy chain of said antibody through a peptide linker; and wherein the Ang-2 antagonist peptide-heavy chain fusion polypeptide comprises an amino acid sequence at least 99% identical or 100% identical as one selected from SEQ ID NO: 37, 39, 41, 43, 45, 47, 49, 51, and 53.

The chimeric molecule of claim 1, wherein said VEGF binding moiety is an Fab with a light chain amino acid sequence of at least 95% identity to SEQ ID NO: 4, and a heavy chain amino acid sequence of at least 95% identity to SEQ ID NO: 5.

The chimeric molecule of claim 8, wherein the Ang-2 antagonist peptide is fused to the N-terminal of the heavy chain of said Fab molecule through a peptide linker.

The chimeric molecule of claim 9, wherein the Ang-2 antagonist peptide-heavy chain fusion polypeptide has an amino acid sequence at least 99% identical as that of SEQ ID NO:19 or SEQ ID NO:20.

The chimeric molecule of claim 8, wherein the Ang-2 antagonist peptide is fused to the C-terminal of the heavy chain of said Fab molecule through a peptide linker.

Chimeric molecule of claim 11, wherein the Ang-2 antagonist peptide-heavy chain fusion polypeptide has an amino acid sequence at least 99% identical to SEQ ID NO: 25 or SEQ ID NO:26.

The chimeric molecule of claim 1, wherein said VEGF binding moiety is an scFv with an amino acid sequence having at least 95% identity to SEQ ID NO: 6.

The chimeric molecule of claim 13, wherein the Ang-2 antagonist peptide is fused to the N-terminal of the scFv; and wherein the peptide-scFv fusion has an amino acid sequence selected from SEQ ID NOS:21 and 22.

The chimeric molecule of claim 13, wherein the Ang2 antagonist peptide is fused to the C-terminal of the scFv optionally; and wherein the peptide-scFv fusion has an amino acid sequence selected from SEQ ID NO:27 and SEQ ID NO:28.

A chimeric molecule comprising a fusion protein that has one or more VEGF-binding moieties and one or two Ang-2 antagonist peptides, wherein said VEGF binding moiety is a VEGF trap with an amino acid sequence having at least 95% identity to SEQ ID NO: 3; wherein the chimeric molecule comprises two identical polypeptide chains, each having an amino acid sequence at least 99% identical to one of SEQ ID NOS:15-17, 23 and 24.

A polynucleotide or polynucleotides encoding the chimeric molecule of any one of claims 1-16.

An expression vector or vectors containing a polynucleotide or polynucleotides of claim 17. A host cell transfected with one or more of the expression vectors of claim 18.

A method of making the chimeric molecule of any one of claims 1-16, comprising culturing a host cell transfected with one or more expression vectors containing a polynucleotide that encodes a chimeric molecule of one of claims 1-16 under conditions that allow expression of the chimeric molecule, and isolating the chimeric molecule.

A pharmaceutical composition comprising the chimeric molecule of any one of claims 1-16 and a pharmaceutically acceptable excipient.

The pharmaceutical composition of claim 21, wherein the pharmaceutical composition contains one or more acceptable carriers.

The pharmaceutical composition of claim 21, wherein the pharmaceutical composition is in the form of a lyophilized formulation or an aqueous solution.

The pharmaceutical compositions of claim 21, wherein the pharmaceutical composition includes one or more of carriers, an excipient, a diluent, a suitable binder, a lubricant, a suspension agent, a coating agent or a solubilizing agent.

A method of treating a patient with cancer, proliferative retinopathy, wet age-related macular degeneration (wAMD), macular edema following retinal vein occlusion (RVO), diabetic macular edema (DME), or diabetic retinopathy (DR) comprising administering to a subject a pharmaceutical composition of claim 21.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

SEQUENCES

SEQ ID NO: 1, Bevacizumab Heavy Chain:
```
          10         20         30         40         50         60
EVQLVESGGG LVQPGGSLRL SCAASGYTFT NYGMNWVRQA PGKGLEWVGW INTYTGEPTY 70         80         90        100        110        120
AADFKRRFTF SLDTSKSTAY LQMNSLRAED TAVYYCAKYP HYYGSSHWYF DVWGQGTLVT 130        140        150        160        170        180
VSSASTKGPS VFPLAPSSKS TSGGTAALGC LVKDYFPEPV TVSWNSGALT SGVHTFPAVL 190        200        210        220        230        240
QSSGLYSLSS VVTVPSSSLG TQTYICNVNH KPSNTKVDKK VEPKSCDKTH TCPPCPAPEL 250        260        270        280        290        300
LGGPSVFLFP PKPKDTLMIS TRPEVTCVVV DVSHEDPEVK FNWYVDGVEV HNAKTKPREE 310        320        330        340        350        360
QYNSTYRVVS VLTVLHQDWL NGKEYKCKVS NKALPAPIEK TISKAKGQPR EPQVYTLPPS 370        380        390        400        410        420
REEMTKNQVS LTCLVKGFYP SDIAVEWESN GQPENNYKTT PPVLDSDGSF FLYSKLTVKD 430        440        450
SRWQQGNVFS CSVMHEALHN HYTQKSLSLS PGK
```

SEQ IS NO: 2, Bevacizumab Light Chain:
```
          10         20         30         40         50         60
DIQMTQSPSS LSASVGDRVT ITCSASQDIS NYLNWYQQKP GKAPKVLIYF TSSLHSGVPS 70         80         90        100        110        120
RFSGSGSGTD FTLTISSLQP EDFATYYCQQ YSTVPWTFGQ GTKVEIKRTV AAPSVFIFPP 130        140        150        160        170        180
SDEQLKSGTA SVVCLLNNFY PREAKVQWKV DNALQSGNSQ EXVTEQDSKD STYSLSSTLT 190        200        210
LSKADYEKHK VYACEVTHQG LSSPVTKSFN RGEC
```

SEQ ID NO: 3, VEGF Trap Aflibercept
```
          10         20         30         40         50         60
SDTGRPFVEM YSEIPEIIHM TEGRELVIPC RVTSPNITVT LKKFPLDTLI PDGKRIIWDS 70         80         90        100        110        120
RKGFIISNAT YKEIGLLTCE ATVNGHLYKT NYLTHRQTNT IIDVVLSPSH GIELSVGEKL 130        140        150        160        170        180
VLNCTARTEL NVGIDFNWEY PSSKHQHKKL VNRDLKTQSG SEMKKFLSTL TIDGVTRSDQ 190        200        210        220        230        240
GLYTCAASSG LMTKKNSTFV RVHEKDKTHT CPPCPAPELL GGPSVFLFPP KPKDTLMISR 250        260        270        280        290        300
TPEVTCVVVD VSHEDPEVKF NWYVDGVEVH NAKTKPREEQ YNSTYRVVSV LTVLHQDWLN 310        320        330        340        350        360
GKEYKCKVSN KALPAPIEKT ISKAKGQPRE PQVYTLPPSR DELTKNQVSL TCLVKGFYPS 370        380        390        400        410        420
DIAVEWESNG QPENNYKTTP PVLDSDGSFF LYSKLTVDKS RWQQGNVFSC SVMHEALHNH

430
YTQKSLSLSP G(K)
```

SEQ ID NO: 4, Protein Sequence for Light Chain, Ranibizumab (VEGF Fab)
DIQLTQSPSSLSASVGDRVTITCSASQDISNYLNWYQQKPGKAPKVLIYFTSSLHSGVPSRFS
GSGSGTDFTLTISSLQPEDFATYYCQQYSTVPWTFGQGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC SEQ ID NO: 5, Protein Sequence for Heavy Chain Ranibizumab (VEGF Fab)
EVQLVESGGGLVQPGGSLRLSCAASGYDFTHYGMNWVRQAPGKGLEWVGWINTYTGE
PTYAADFKRRFTFSLDTSKSTAYLQMNSLRAEDTAVYYCAKYPYYYGTSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHL SEQ ID NO: 6, Protein Sequence for a VEGF ScFv
EIVMTQSPSTLSASVGDRVIITCQASEIIHSWLAWYQQKPGKAPKLLIYLASTLASGVPSRF
SGSGSGAEFTLTISSLQPDDFATYYCQNVYLASTNGANFGQGTKLTVLGGGGSGGGG
SGGGGSGGGGSEVQLVESGGGLVQPGGSLRLSCTASGFSLTDYYYMTWVRQAPGKGL
EWVGFIDPDDDPYYATWAKGRFTISRDNSKNTLYLQMNSLRAEDTAVYYCAGGDHNSG

WGLDIWGQGTLVTVSS

SEQ ID NO: 7, Protein Sequence for a heavy chain of a VEGF antibody
EVQLVESGGGLVQPGGSLRLSCAAAS<u>GYDFTH</u>YGMNWVRQAPGKGLEWVGW<u>INTYTGE
PTYAADFKRR</u>FTFSLDTSKSTAYLQMNSLRAEDTAVY<u>YCAKYPYYYGTSHWYFDV</u>WGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPP
CPAPEAAGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

SEQ ID NO: 8, L1-7
AQQTNFMPM DDLEQRLYEQ FILQQG

SEQ ID NO: 9, L1-10
AQQKFQPLD ELEQTLYEQF MLQQA

SEQ ID: NO: 10, L1-15
AQQKYQPLD ELDKTLYDQF MLQQG

SEQ ID NO: 11, L1-7B
QTNFMPM DDLEQRLYEQ FILQQG

SEQ ID NO: 12, L1-10B
QKFQPLD ELEQTLYEQF MLQQA

SEQ ID NO: 13, L1-15B
QKYQPLD ELDKTLYDQF MLQQG

SEQ ID NO: 14, CVX-060:
QKYQPLDEKDKTLYDQFMLQQG

SEQ ID NO 15, L1-15 fused to the Ki-terminus of the VEGF Trap, with linker
peptide GGGGSGGGGSGGGGS
         10         20         30         40         50         60
AQQKYQPLDE LDKTLYDQFM LQQGGGGGSG GGGSGGGGSS DTGRPFVEMY SEIPEIIHMT 70         80         90        100        110        120
EGRELVIPCR VTSPNITVTL KKFPLDTLIP DGKRIIWDSR KGFIISNATY KEIGLLTCEA 130        140        150        160        170        180
TVNGHLYKTN YLTHRQTNTI IDVVLSPSHG IELSVGEKLV LNCTARTELN VGIDFNWEYP 190        200        210        220        230        240
SSKHQHKKLV NRDLKTQSGS EMKKFLSTLT IDGVTRSDQG LYTCAASSGL MTKKNSTFVR 250        260        270        280        290        300
VHEKDKTHTC PPCPAPELLG GPSVFLFPPK PKDTLMISRT PEVTCVVVDV SHEDPEVKFN 310        320        330        340        350        360
WYVDGVEVHN AKTKPREEQY NSTYRVVSVL TVLHQDWLNG KEYKCKVSNK ALPAPIEKTI 370        380        390        400        410        420
SKAKGQPREP QVYTLPPSRD ELTKNQVSLT CLVKGFYPSD IAVEWESNGQ PENNYKTTPP 430        440        450        460        470
VLDSDGSFFL TSKLTVDKSR WQQGNVFSCS VMHEALHNHY TQKSLSLSPG K SEQ ID NO 16, Protein Sequence for AMD-I (L1-15 fused to VEGF Trap)
Xaa$_1$Xaa$_2$QKXaa$_5$QPLDELXaa$_{12}$Xaa$_{13}$TLYXaa$_{17}$QFMLQQGXaa$_{25}$Xaa$_{28}$(GGGGS)$_n$SDTGRPF
VEMYSEIPEIIHMTEGRELVIPCRVTSPNITVTLKKFPLDTLIPDGKRIIWDSRKGFIISNATY
KEIGLITCEATVNGHLYKTNYLTHRQTNTIIDVVLSPSHGIELSVGEKLVLNCTARTELNVG
IDFNWEYPSSKHQHKKLVNRDLKTQSGSEMKKFLSTLTIDGVTRSDQGLYTCAASSGLM
TKKNSTFVRVHEKDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSD1AVEWESNG
QPENNYKTTPPVLDSDGSFFLYSKLTVDKSRWQQGNVFSCSVMHEALHNHYTQKSLSL
SPG(K)
wherein Xaa1 is A, G, or deleted; Xaa2 is Q or A or deleted; Xaa25 is L or deleted; Xaa5 is Y
or F; Xaa12 is D or E; Xaa13 is Q or K; Xaa17 is D or E; Xaa26 is E is deleted; n = 0, 1,
2, 3, 4, or 5; and the C-terminal amino acid K may be deleted.

SEQ ID NO 17, Protein Sequence for AMD-J (L1-7 fused to VEGF Trap)
Xaa$_1$Xaa$_2$QTNFMPMDDLEQRLYEQFILQQGXaa$_{26}$Xaa$_{27}$(GGGGS)$_n$SDTGRPFVEMYSEIPEII
HMTEGRELVIPCRVTSPNITVTLKKFPLDTLIPDGKRIIWDSRKGRISNATYKEIGLLTCEAT
VNGHLYKTNYLTHRQTNTIIDVVLSPSHGIELSVGEKLVLNCTARTELNVGIDFNWEYPSS
KHQHKKLVNRDLKTQSGSEMKKFLSTLTIDGVTRSDQGLYTCAASSGLMTKKNSTFVRV
HEKDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTT -continued PPVLDSDGSFFLYSKLTVDKSRWQQGNVFSCSVMHEALHNHYTQKSLSLSPG(K)
wherein Xaa1 is A, G, or deleted; Xaa2 is Q or A or deleted; Xaa26 is L or deleted; Xaa27 is
E is deleted; n = 0, 1, 2, 3, 4, or 5; and the C-terminal amino acid K may be deleted.

SEQ ID NO 19, Protein Sequence for AMD-K Heavy Chain (L1-15 fused to VEGF Fab)
$Xaa_1Xaa_2QKXaa_5QPLDELXaa_{12}Xaa_{13}TLYXaa_{17}QFMLQQGXaa_{25}Xaa_{26}(GGGGS)_n$EVQLVES
GGGLVQPGGSLRLSCAASGYDFTHYGMNWVRQAPGKGLEVWGWNTYTGEPTYAADF
KRRFTFSLDTSKSTAYLQMNSLRAEDTAVYYCAKYPYYYGTSHWYFDVWGQGTLVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHL
wherein Xaa1 is A, G, or deleted; Xaa2 is Q or A or deleted; Xaa5 is Y or F; Xaa12 is D or E;
Xaa13 is Q or K; Xaa17 is D or E; Xaa25 is L or deleted; Xaa26 is E is deleted; and n = 0,
1, 2, 3, 4, or 5.

SEQ ID NO 20, Protein Sequence for AMD-L Heavy Chain (L1-7 fused to VEGF Fab)
$Xaa_1Xaa_2QTNFMPMDDLEQRLYEQFILQQGXaa_{26}Xaa_{27}(GGGGS)_n$EVQLVESGGGLVQPGG
SLRLSCAASGYDFTHYGMNWVRQAPGKGLEVWGWINTYTGEPTYAADFKRRFTFSLDT
SKSTAYLQMNSLRAEDTAVYYCAKYPYYYGTSHWYFDVWGQGTLVTVSSASTKGPSVF
PLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHL
wherein Xaa1 is A, G, or deleted; Xaa2 is Q or A or deleted; Xaa26 is L or deleted; Xaa27 is
E is deleted; and n = 0, 1, 2, 3, 4, or 5.

SEQ ID NO 21, Protein Sequence for AMD-N (L1-15 fused to VEGF ScFv)
$Xaa_1Xaa_2QKXaa_5QPLDELXaa_{12}Xaa_{13}TLYXaa_{17}QFMLQQGXaa_{25}Xaa_{26}(GGGGS)_n$EIVMTQSP
STLSASVGDRVIITCQASEIIHSWLAWYQQKPGKAPKLLIYLASTLASGVPSRFSGSGSGA
EFTLTISSLQPDDFATYYCQNVYLASTNGANFGQGTKLTVLGGGGGSGGGGSGGGGSG
GGGSEVQLVESGGGLVQPGGSLRLSCTASGFSLTDYYYMTWVRQAPGKGLEWVGFID
PDDDPYYATWAKGRFTISRDNSKNTLYLQMNSLRAEDTAVYYCAGGDHNSGWGLDIWG
QGTLVTVSS
wherein Xaa1 is A, G, or deleted; Xaa2 is Q or A or deleted; Xaa5 is Y or F; Xaa12 is D or E;
Xaa13 is Q or K; Xaa17 is D or E; Xaa25 is L or deleted; Xaa26 is E is deleted; and n = 0,
1, 2, 3, 4, or 5

SEQ ID NO 22, Protein Sequence for AMD-Q (L1-7 fused to VEGF ScFv)
$Xaa_1Xaa_2QTNFMPMDDLEQRLYEQFILQQGXaa_{26}Xaa_{27}(GGGGS)_n$EIVMTQSPSTLSASV
GDRVIITCQASEIIHSWLAVVYQQKPGKAPKWYLASTLASGVPSRFSGSGSGAEFTLTISS
LQPDDFATYYCQNVYLASTNGANFGQGTKLTVLGGGGSGGGGSGGGGSGGGGSEV
QLVESGGGLVQPGGSLRLSCTASGFSLTDYYYMTWVRQAPGKGLEWVGFIDPDDDPYY
ATWAKGRFTISRDNSKNTLYLQMNSLRAEDTAVYYCAGGDHNSGWGLDIWGQGTLVTV
SS
wherein Xaa1 is A, G, or deleted; Xaa2 is Q or A or deleted; Xaa26 is L or deleted; Xaa27 is
E is deleted; and n = 0, 1, 2, 3, 4, or 5.

SEQ ID NO 23, Protein Sequence for AMD-I-C terminal (L1-15 fused to C-terminal of VEGF Trap)
SDTGRPFVEMYSEIPEIIHMTEGRELVIPCRVTSPNITVTLKKFPLDTLIPDGKRIIWDSRKG
FIISNATYKEIGLLTCEATVNGHLYKTNYLTHRQTNTIIDVVLSPSHGIELSVGEKLVLNCTA
RTELNVGIDFNWEYPSSKHQHKKLVNRDLKTQSGSEMKKFLSTLTIDGVTRSDQGLYTC
AASSGLMTKKNSTFVRVHEKDKTHTCPPCPAPELLGGPSVFLFPPKPKDTLIVIISRTPEVT
CVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHY
$TQKSLSLSPGA(GGGGS)_nXaa_1Xaa_2QKXaa_5QPLDELXaa_{12}Xaa_{13}TLYXaa_{17}QFNMLQQG$
$Xaa_{25}Xaa_{26}$
wherein Xaa1 is A, G, or deleted; Xaa2 is Q or A or deleted; Xaa5 is Y or F; Xaa12 is D or E;
Xaa13 is Q or K; Xaa17 is D or E; Xaa25 is L or deleted; Xaa26 is E is deleted; and n = 0,
1, 2, 3, 4, or 5.

SEQ ID NO 24, Protein Sequence for AMD-J-C terminal (L1-7 fused to C-terminal of VEGF Trap)
SDTGRPFVEMYSEIPEIIHMTEGRELVIPCRVTSPNITVTLKKFPLDTLIPDGKRIIWDSRKGFII
SNATYKEIGLITCEATVNGHLYKTNYLTHRQTNTIIDVVLSPSHGIELSVGEKLVLNCTART
ELNVGIDFNWEYPSSKHQHKKLVNRDLKTQSGSEMKKFLSTLTIDGVTRSDQGLYTCAA
SSGLMTKKNSTFVRVHEKDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYT
$QKSLSLSPGA(GGGGS)_nXaa_1Xaa_2QTNFMPMDDLEQRLYEQFILQQGXaa_{26}Xaa_{27}$
wherein Xaa1 is A, G, or deleted; Xaa2 is Q or A or deleted; Xaa26 is L or deleted; Xaa27 is
E is deleted; and n = 0, 1, 2, 3, 4, or 5.

SEQ ID NO 25, Protein Sequence for AMD-K-C terminal Heavy Chain (L1-15
fused to C-terminal VEGF Fab)
EVQLVESGGGLVQPGGSLRLSCAASGYDFTHYGMNWVRQAPGKGLEWVGWINTYTGEPT
YAADFKRRFTFSLDTSKSTAYLQMNSLRAEDTAVYYCAKYPYYYGTSHWYFDVWGQGT
LVTVSSASTKGPSVFPLAPSSKSTSGGTAALGCLVKDYFPEPVTVSWNSGALTSGVHTF
$PAVLQSSGLYSLSSVVTVPSSSLGTQTYICNVNHKPSNTKVDKKVEPKSCDKTHL(GGGGS)_n$
$Xaa_1Xaa_2QKXaa_5QPLDELXaa_{12}X_{13}TLYXaa_{17}QFMLQQGXaa_{25}Xaa_{26}$
wherein Xaa1 is A, G, or deleted; Xaa2 is Q or A or deleted; Xaa5 is Y or F; Xaa12 is D or E;
Xaa13 is Q or K; Xaa17 is D or E; Xaa25 is L or deleted; Xaa26 is E is deleted; and n = 0,
1, 2, 3, 4, or 5.

SEQ ID NO 26, Protein Sequence for AMD-L-C terminal Heavy Chain (L1-7 fused to VEGF Fab)
EVQLVESGGGLVQPGGSLRLSCAASGYDFTHYGMNWVRQAPGKGLEWVGWINTYTGEPT
YAADFKRRFTFSLDTSKSTAYLQMNSLRAEDTAVYYCAKYPYYYGTSHWYFDVWGQGT
LVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHL(GGGG
S)nXaa1Xaa2QTNFMPMDDLEQRLYEQFILQQGXaa2Xaa27
wherein Xaa1 is A, G, or deleted; Xaa2 is Q or A or deleted; Xaa26 is L or deleted; Xaa27 is
E is deleted; and n = 0, 1, 2, 3, 4, or 5.

SEQ ID NO 27, Protein Sequence for AMD-N-C terminal (L1-15 fused to C-
terminal VEGF ScFv)
EIVMTQSPSTLSASVGDRVIITCQASEIIHSWLAVVYQQKPGKAPKLLIYLASTLASGVPSRF
SGSGSGAEFTLTISSLQPDDFATYYCQNVYLASTNGANFGQGTKLTVLGGGGSGGGG
SGGGGSGGGGSEVQLVESGGGLVQPGGSLRLSCTASGFSLTDYYYMTWVRQAPGKGL
EWVGFIDPDDDPYYATWAKGRFTISRDNSKNTLYLQMNSLRAEDTAVYYCAGGDHNSG
WGLDIWGQGTLVTVSS(GGGGS)$_n$Xaa$_1$Xaa$_2$QKXaa$_5$QPLDELXaa$_{12}$Xaa$_{13}$TLYXaa$_{17}$QFML
QQGXaa$_{25}$Xaa$_{26}$; wherein Xaa1 is A, G, or deleted; Xaa2 is Q or A or deleted; Xaa5 is Y
or F; Xaa12 is D or E; Xaa13 is Q or K; Xaa17 is D or E; Xaa25 is L or deleted; Xaa26 is
E is deleted; and n = 0, 1, 2, 3, 4, or 5.

SEQ ID NO 28, Protein Sequence for AMD-Q-C terminal (L1-7 fused to VEGF ScFv)
EIVMTQSPSTLSASVGDRVIITCQASEIIHSWLAVVYQQKPGKAPKLLIYLASTLASGVPSRFS
GSGSGAEFTLTISSLQPDDFATYYCQNVYLASTNGANFGQGTKLTVLGGGGGSGGGGS
GGGGSGGGGSEVQLVESGGGLVQPGGSLRLSCTASGFSLTDYYYMTWVRQAPGKGLE
WVGFIDPDDDPYYATWAKGRFTISRDNSKNTLYLQMNSLRAEDTAVYYCAGGDHNSGW
GLDIWGQGTLVTVSS(GGGGS)$_n$
Xaa1Xaa2QTNFMPMDDLEQRLYEQFILQQGXaa26Xaa27
wherein Xaa1 is A, G, or deleted; Xaa2 is Q or A or deleted; Xaa26 is L or deleted; Xaa27 is
E is deleted; and n = 0, 1, 2, 3, 4, or 5.

SEQ ID NO: 29, Protein Sequence for ASKB712-0 (L1-15 fused to the N-
terminal of an VEGF-binding antibody)
AQQKYQPLDELDKTLYDQFMLQQGLEGGGGSGGGGSGGGGSEVQLVESGGGLVQPGGS
LRLSCAASGYDFTHYGMNWVRQAPGKGLEWVGWINTYTGEPTYAADFKRRFTFSLDTS
KSTAYLQMNSLRAEDTAVYYCAKYPYYYGTSHWYFDVWGQGTLVTVSSASTKGPSVFPP
LAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPEAAGGPSVFLPPP
KPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 30, Protein Sequence for ASKB712-03 (L1-15 fused to the N-
terminal of an VEGF-binding antibody)
Xaa$_1$Xaa$_2$QKXaa$_5$QPLDELXaa$_{12}$Xaa$_{13}$TLYXaa$_{17}$QFMLQQGXaa$_{25}$Xaa$_{26}$(GGGGS)$_n$EVQLVES
GGGLVQPGGSLRLSCAASGYDFTHYGMNWVRQAPGKGLEWVGWINTYTGEPTYAADF
KRRFTFSLDTSKSTAYLQMNSLRAEDTAVYYCAKYPYYYGTSHWYFDVWGQGTLVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPEAA
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVD
KSRWQQGNVFSCSVMHEALHNHYTQKSLSLSPGK; wherein Xaa1 is A, G, or deleted;
Xaa2 is Q or A or deleted; Xaa5 is Y or F; Xaa12 is D or E; Xaa13 is Q or K; Xaa 17 is D
or E; Xaa25 is L or deleted; Xaa26 is E is deleted; n = 0, 1, 2, 3, 4, or 5; and the C-
terminal amino acid K may be deleted.

SEQ ID NO: 31, Protein Sequence for ASKB712-02 (L1-15 fused to the C-
terminal of an VEGF-binding antibody)
EVQLVESGGGLVQPGGSLRLSCAASGYDFTHYGMNWVRQAPGKGLEWVGWINTYTGEPT
YAADFKRRFTFSLDTSKSTAYLQMNSLRAEDTAVYYCAKYPYYYGTSHWYFDVWGQGT
LVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCP
APEAAGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPGAGGGGSGGGGSGGGGSA
QQKYQPLDELDKTLYDQFMLQQGLE SEQ ID NO: 32, Protein Sequence for ASKB712-04 (L1-15 fused to the C-
terminal of an VEGF-binding antibody)
EVQLVESGGGLVQPGGSLRLSCAASGYDFTHYGMNWVRQAPGKGLEWVGWINTYTGE
PTYAADFKRRFTFSLDTSKSTAYLQMNSLRAEDTAVYYCAKYPYYYGTSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPP
CPAPEAAGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGA
(GGGGS)$_n$Xaa$_1$Xaa$_2$QKXaa$_5$QPLDELXaa$_{12}$Xaa$_{13}$TLYXaa$_{17}$QFMLQQGXaa$_{25}$Xaa$_{26}$ wherein Xaa1 is A, G, or deleted; Xaa2 is Q or A or deleted; Xaa25 is L or deleted; Xaa5 is Y or F; Xaa12 is D or E; Xaa13 is Q or K; Xaa 17 is D or E; Xaa26 is E is deleted; n = 0, 1, 2, 3, 4, or 5.

SEQ ID NO: 33, Protein Sequence for ASKB712-P (L1-7 fused to the N-terminal of an VEGF-binding antibody)
Xaa1Xaa2QTNFMPMDDLEQRLYEQFILQQGXaa26Xaa27(GGGGS)nEVQLVESGGGLVQP
GGSLRLSCAAS<u>GYDFTH</u>YGMNWVRQAPGKGLEWVGW<u>INTYTGEP</u>TYAADFKRRFTFSL
DTSKSTAYLQMNSLRAEDTAVY<u>YCAKYPYYYGTSHWYF</u>DVWGQGTLVTVSSASTKGPS
VFPLAPSSKSTSGGTAALGCLVKDYFPEPVTV -continued CGTGGACGGCGTGGAAGTGCACAACGCCAAGACCAAGCCTAGAGAGGAACAGTACA
ACTCCACCTACAGAGTGGTGTCCGTGCTGACCGTGCTGCACCAGGATTGGCTGAAC
GGCAAAGAGTACAAGTGCAAGGTGTCCAACAAGGCCCTGCCTGCTCCTATCGAAAA
GACCATCTCCAAGGCCAAGGGCCAGCCTAGGGAACCCCAGGTTTACACCTTGCCTC
CAAGCCGGGAAGAGATGACCAAGAACCAGGTGTCCCTGACCTGCCTCGTGAAGGGC
TTCTACCCTTCCGATATCGCCGTGGAATGGGAGAGCAATGGCCAGCCTGAGAACAA
CTACAAGACCACTCCTCCTGTGCTGGACTCCGACGGCTCATTCTTCCTGTACTCCAA
GCTGACAGTGGACAAGTCCAGATGGCAGCAGGGCAACGTGTTCTCCTGCTCCGTGA
TGCACGAGGCCCTGCACAATCACTACACACAGAAGTCCCTGTCTCTGTCCCCTGGCA
AGTAA SEQ ID NO: 37-7120_L7_2xGS_Protein sequence
MEFGLSWLFLVAILKGALAAQTNFMPMDDLEQRLYEQFILQQGLEGGGGSGGGGSEVQLV
ESGGGLVQPGGSLRLSCAASGYDFTHYGMNWVRQAPGKGLEWVGWINTYTGEPTYAA
DFKRRFTFSLDTSKSTAYLQMNSLRAEDTAVYYCAKYPYYYGTSHWYFDVWGQGTLVT
VSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPE
AAGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGK SEQ ID NO: 38-7120_L7_1xGS_DNA sequence
ATGGAATTCGGCCTGTCTTGGCTGTTCCTGGTGGCCATTCTGAAGGGCGCTCTGGCCG
CTCAGACCAACTTCATGCCTATGGACGACCTGGAACAGCGGCTGTACGAGCAGTTCA
TCCTGCAGCAAGGACTGGAAGGAGGCGGTGGATCTGAAGTGCAGCTGGTTGAAAGT
GGCGGCGGATTGGTTCAGCCTGGCGGATCTCTGAGACTGTCTTGTGCCGCCTCTGG
CTACGACTTCACCCACTACGGCATGAATTGGGTCCGACAGGCTCCCGGCAAAGGCC
TGGAATGGGTCGGATGGATCAACACCTATACCGGCGAGCCTACCTACGCCGCCGAT
TTCAAGCGGAGATTCACCTTCTCCCTGGACACCTCCAAGTCTACCGCCTACCTGCAG
ATGAACTCCCTGAGAGCCGAGGACACCGCCGTGTACTACTGCGCTAAGTACCCCTA
CTACTACGGCACCAGCCACTGGTACTTCGACGTGTGGGGACAGGGCACACTGGTCA
CAGTGTCCTCCGCCTCTACCAAGGGACCCTCTGTGTTCCTCTGGCTCCCTCCAGCA
AGTCCACCTCTGGTGAACAGCTGCTCTGGGCTGCCTGGTCAAGGACTACTTTCCTG
AGCCTGTGACCGTGTCCTGGGCTTCTGGTGCTCTGACATCTGGCGTGCACACCTTTC
CAGCTGTGCTGCAGTCCTCCGGCCTGTACTCTCTGTCCTCTGTCGTGACCGTGCCTT
CCAGCTCTCTGGGAACCCAGACCTACATCTGCAATGTGAACCACAAGCCTTCCAACA
CCAAGGTCGACAAGAAGGTGGAACCCAAGTCCTGCGATAAGACCCACACCTGTCCT
CCATGTCCTGCTCCAGAAGCTGCTGGCGGCCCATCCGTGTTTCTGTTCCCTCCAAAG
CCTAAGGACACCCTGATGATCTCTCGGACCCCTGAAGTGACCTGCGTGGTGGTGGA
TGTGTCTCACGAGGACCCAGAAGTGAAGTTCAATTGGTACGTGGACGGCGTGGAAG
TGCACAACGCCAAGACCAAGCCTAGAGAGGAACAGTACAACTCCACCTACAGAGTG
GTGTCCGTGCTGACCGTGCTGCACCAGGATTGGCTGAACGGCAAAGAGTACAAGTG
CAAGGTGTCCAACAAGGCCCTGCCTGCTCCTATCGAAAAGACCATCTCCAAGGCCAA
GGGCCAGCCTAGGGAACCCCAGGTTTACACCTTGCCTCCAAGCCGGGAAGAGATGA
CCAAGAACCAGGTGTCCCTGACCTGCCTCGTGAAGGGCTTCTACCCTTCCGATATCG
CCGTGGAATGGGAGAGCAATGGCCAGCCTGAGAACAACTACAAGACCACTCCTCCT
GTGCTGGACTCCGACGGCTCATTCTTCCTGTACTCCAAGCTGACAGTGGACAAGTCC
AGATGGCAGCAGGGCAACGTGTTCTCCTGCTCCGTGATGCACGAGGCCCTGCACAA
TCACTACACACAGAAGTCCCTGTCTCTGTCCCCTGGCAAGTAA SEQ ID NO: 39-7120_L7_1xGS_DNA sequence
MEFGLSWLFLVAILKGALAAQTNFMPMDDLEQRLYEQFILQQGLEGGGGSEVQLVESGGGL
VQPGGSLRLSCAASGYDFTHYGMNWVRQAPGKGLEWVGWINTYTGEPTYAADFKRRF
TFSLDTSKSTAYLQMNSLRAEDTAVYYCAKYPYYYGTSHWYFDVWGQGTLVTVSSAST
KGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGP
SVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSR
WQQGNVFSCSVMHEALHNHYTQKSLSLSPGK SEQ ID NO: 40 7120_L10_3xGS_DNA sequence
ATGGAATTCGGCCTGTCTTGGCTGTTCCTGGTGGCCATTCTGAAGGGCGCTTTGGCCG
CTCAGCAGAAGTTTCAGCCTCTGGACGAGCTGGAACAGACCCTGTACGAGCAGTTC
ATGCTCCAGCAGGCTTTGGAAGGCGGCGGAGGATCTGGCGGAGGCGGTAGCGGAG
GCGGTGGATCTGAAGTGCAGCTGGTTGAAAGTGGCGGCGGATTGGTTCAGCCTGGC
GGATCTCTGAGACTGTCTTGTGCCGCCTCTGGCTACGACTTCACCCACTACGGCATG
AATTGGGTCCGACAGGCTCCCGGCAAAGGCCTGGAATGGGTCGGATGGATCAACAC
CTATACCGGCGAGCCTACCTACGCCGCCGATTTCAAGCGGAGATTCACCTTCTCCCT
GGACACCTCCAAGTCTACCGCCTACCTGCAGATGAACTCCCTGAGAGCCGAGGACA
CCGCCGTGTACTACTGCGCTAAGTACCCCTACTACTACGGCACCAGCCACTGGTACT
TCGACGTGTGGGGACAGGGCACACTGGTCACAGTGTCCTCCGCCTCTACCAAGGGA
CCCTCTGTGTTCCTCTGGCTCCCTCCAGCAAGTCCACCTCTGGTGAACAGCTGCT
CTGGGCTGCCTGGTCAAGGACTACTTTCCTGAGCCTGTGACCGTGTCCTGGGCTTCT
GGTGCTCTGACATCTGGCGTGCACACCTTTCCAGCTGTGCTGCAGTCCTCCGGCCT
GTACTCTCTGTCCTCTGTCGTGACCGTGCCTTCCAGCTCTCTGGGAACCCAGACCTA
CATCTGCAATGTGAACCACAAGCCTTCCAACACCAAGGTCGACAAGAAGGTGGAACC
CAAGTCCTGCGATAAGACCCACACCTGTCCTCCATGTCCTGCTCCAGAAGCTGCTGG
CGGCCCATCCGTGTTTCTGTTCCCTCCAAAGCCTAAGGACACCCTGATGATCTCTCG
GACCCCTGAAGTGACCTGCGTGGTGGTGGATGTGTCTCACGAGGACCCAGAAGTGA

```
                                      -continued
AGTTCAATTGGTACGTGGACGGCGTGGAAGTGCACAACGCCAAGACCAAGCCTAGA
GAGGAACAGTACAACTCCACCTACAGAGTGGTGTCCGTGCTGACCGTGCTGCACCA
GGATTGGCTGAACGGCAAAGAGTACAAGTGCAAGGTGTCCAACAAGGCCCTGCCTG
CTCCTATCGAAAAGACCATCTCCAAGGCCAAGGGCCAGCCTAGGGAACCCCAGGTT
TACACCTTGCCTCCAAGCCGGGAAGAGATGACCAAGAACCAGGTGTCCCTGACCTG
CCTCGTGAAGGGCTTCTACCCTTCCGATATCGCCGTGGAATGGGAGAGCAATGGCC
AGCCTGAGAACAACTACAAGACCACTCCTCCTGTGCTGGACTCCGACGGCTCATTCT
TCCTGTACTCCAAGCTGACAGTGGACAAGTCCAGATGGCAGCAGGGCAACGTGTTC
TCCTGCTCCGTGATGCACGAGGCCCTGCACAATCACTACACACAGAAGTCCCTGTCT
CTGTCCCCTGGCAAGTAA SEQ ID NO: 41 7120_L10_3xGS_Protein sequence
MEFGLSWLFLVAILKGALAAQQKFQPLDELEQTLYEQFMLQQALEGGGGSGGGGSGGGGS
EVQLVESGGGLVQPGGSLRLSCAASGYDFTHYGMNWVRQAPGKGLEWVGWINTYTGE
PTYAADFKRRFTFSLDTSKSTAYLQMNSLRAEDTAVYYCAKYPYYYGTSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPP
CPAPEAAGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID NO: 42 7120_L10_2xGS_DNA sequence
ATGGAATTCGGCCTGTCTTGGCTGTTCCTGGTGGCCATTCTGAAGGGCGCTTTGGCCG
CTCAGCAGAAGTTTCAGCCTCTGGACGAGCTGGAACAGACCCTGTACGAGCAGTTC
ATGCTCCAGCAGGCTTTGGAAGGCGGCGGAGGATCTGGAGGCGGTGGATCTGAAG
TGCAGCTGGTTGAAAGTGGCGGCGGATTGGTTCAGCCTGGCGGATCTCTGAGACTG
TCTTGTGCCGCCTCTGGCTACGACTTCACCCACTACGGCATGAATTGGGTCCGACAG
GCTCCCGGCAAAGGCCTGGAATGGGTCGGATGGATCAACACCTATACCGGCGAGCC
TACCTACGCCGCCGATTTCAAGCGGAGATTCACCTTCTCCCTGGACACCTCCAAGTC
TACCGCCTACCTGCAGATGAACTCCCTGAGAGCCGAGGACACCGCCGTGTACTACT
GCGCTAAGTACCCCTACTACTACGGCACCAGCCACTGGTACTTCGACGTGTGGGGA
CAGGGCACACTGGTCACAGTGTCCTCCGCCTCTACCAAGGGACCCTCTGTGTTTCCT
CTGGCTCCCTCCAGCAAGTCCACCTCTGGTGGAACAGCTGCTCTGGGCTGCCTGGT
CAAGGACTACTTTCCTGAGCCTGTGACCGTGTCCTGGGCTTCTGGTGCTCTGACATC
TGGCGTGCACACCTTTCCAGCTGTGCTGCAGTCCTCCGGCCTGTACTCTCTGTCCTC
TGTCGTGACCGTGCCTTCCAGCTCTCTGGGAACCCAGACCTACATCTGCAATGTGAA
CCACAAGCCTTCCAACACCAAGGTCGACAAGAAGGTGGAACCCAAGTCCTGCGATA
AGACCCACACCTGTCCTCCATGTCCTGCTCCAGAAGCTGCTGGCGGCCCATCCGTG
TTTCTGTTCCCTCCAAAGCCTAAGGACACCCTGATGATCTCTCGGACCCCTGAAGTG
ACCTGCGTGGTGGTGGATGTGTCTCACGAGGACCCAGAAGTGAAGTTCAATTGGTA
CGTGGACGGCGTGGAAGTGCACAACGCCAAGACCAAGCCTAGAGAGGAACAGTACA
ACTCCACCTACAGAGTGGTGTCCGTGCTGACCGTGCTGCACCAGGATTGGCTGAAC
GGCAAAGAGTACAAGTGCAAGGTGTCCAACAAGGCCCTGCCTGCTCCTATCGAAAA
GACCATCTCCAAGGCCAAGGGCCAGCCTAGGGAACCCCAGGTTTACACCTTGCCTC
CAAGCCGGGAAGAGATGACCAAGAACCAGGTGTCCTGACCTGCCTCGTGAAGGGC
TTCTACCCTTCCGATATCGCCGTGGAATGGGAGAGCAATGGCCAGCCTGAGAACAA
CTACAAGACCACTCCTCCTGTGCTGGACTCCGACGGCTCATTCTTCCTGTACTCCAA
GCTGACAGTGGACAAGTCCAGATGGCAGCAGGGCAACGTGTTCTCCTGCTCCGTGA
TGCACGAGGCCCTGCACAATCACTACACACAGAAGTCCCTGTCTCTGTCCCCTGGCA
AGTAA SEQ ID NO: 43 7120_L10_2xGS_Protein sequence
MEFGLSWLFLVAILKGALAAQQKFQPLDELEQTLYEQFMLQQALEGGGGSGGGGSEVQLV
ESGGGLVQPGGSLRLSCAASGYDFTHYGMNWVRQAPGKGLEWVGWINTYTGEPTYAA
DFKRRFTFSLDTSKSTAYLQMNSLRAEDTAVYYCAKYPYYYGTSHWYFDVWGQGTLVT
VSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPE
AAGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGK SEQ ID NO: 44 7120_L10_3xGS_DNA sequence
ATGGAATTCGGCCTGTCTTGGCTGTTCCTGGTGGCCATTCTGAAGGGCGCTTTGGCCG
CTCAGCAGAAGTTTCAGCCTCTGGACGAGCTGGAACAGACCCTGTACGAGCAGTTC
ATGCTCCAGCAGGCTTTGGAAGGAGGCGGTGGATCTGAAGTGCAGCTGGTTGAAAG
TGGCGGCGGATTGGTTCAGCCTGGCGGATCTCTGAGACTGTCTTGTGCCGCCTCTG
GCTACGACTTCACCCACTACGGCATGAATTGGGTCCGACAGGCTCCCGGCAAAGGC
CTGGAATGGGTCGGATGGATCAACACCTATACCGGCGAGCCTACCTACGCCGCCGA
TTTCAAGCGGAGATTCACCTTCTCCCTGGACACCTCCAAGTCTACCGCCTACCTGCA
GATGAACTCCCTGAGAGCCGAGGACACCGCCGTGTACTACTGCGCTAAGTACCCCT
ACTACTACGGCACCAGCCACTGGTACTTCGACGTGTGGGGACAGGGCACACTGGTC
ACAGTGTCCTCCGCCTCTACCAAGGGACCCTCTGTGTTTCCTCTGGCTCCCTCCAGC
AAGTCCACCTCTGGTGGAACAGCTGCTCTGGGCTGCCTGGTCAAGGACTACTTTCCT
GAGCCTGTGACCGTGTCCTGGGCTTCTGGTGCTCTGACATCTGGCGTGCACACCTTT
CCAGCTGTGCTGCAGTCCTCCGGCCTGTACTCTCTGTCCTCTGTCGTGACCGTGCCT
TCCAGCTCTCTGGGAACCCAGACCTACATCTGCAATGTGAACCACAAGCCTTCCAAC
ACCAAGGTCGACAAGAAGGTGGAACCCAAGTCCTGCGATAAGACCCACACCTGTCC
TCCATGTCCTGCTCCAGAAGCTGCTGGCGGCCCATCCGTGTTTCTGTTCCCTCCAAA
GCCTAAGGACACCCTGATGATCTCTCGGACCCCTGAAGTGACCTGCGTGGTGGTGG
```

```
                              -continued
ATGTGTCTCACGAGGACCCAGAAGTGAAGTTCAATTGGTACGTGGACGGCGTGGAA
GTGCACAACGCCAAGACCAAGCCTAGAGAGGAACAGTACAACTCCACCTACAGAGT
GGTGTCCGTGCTGACCGTGCTGCACCAGGATTGGCTGAACGGCAAAGAGTACAAGT
GCAAGGTGTCCAACAAGGCCCTGCCTGCTCCTATCGAAAAGACCATCTCCAAGGCC
AAGGGCCAGCCTAGGGAACCCCAGGTTTACACCTTGCCTCCAAGCCGGGAAGAGAT
GACCAAGAACCAGGTGTCCCTGACCTGCCTCGTGAAGGGCTTCTACCCTTCCGATAT
CGCCGTGGAATGGGAGAGCAATGGCCAGCCTGAGAACAACTACAAGACCACTCCTC
CTGTGCTGGACTCCGACGGCTCATTCTTCCTGTACTCCAAGCTGACAGTGGACAAGT
CCAGATGGCAGCAGGGCAACGTGTTCTCCTGCTCCGTGATGCACGAGGCCCTGCAC
AATCACTACACACAGAAGTCCCTGTCTCTGTCCCCTGGCAAGTAA SEQ ID NO: 45 7120_L10_1xGS_Protein sequence
MEFGLSWLFLVAILKGALAAQQKFQPLDELEQTLYEQFMLQQALEGGGGSEVQLVESGGGL
VQPGGSLRLSCAASGYDFTHYGMNWVRQAPGKGLEWVGWINTYTGEPTYAADFKRRF
TFSLDTSKSTAYLQMNSLRAEDTAVYYCAKYPYYYGTSHWYFDVWGQGTLVTVSSAST
KGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGP
SVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSR
WQQGNVFSCSVMHEALHNHYTQKSLSLSPGK SEQ ID NO: 46 7120_C terminal L7_1xGS_DNA sequence
ATGGAATTCGGCCTGTCTTGGCTGTTCCTGGTGGCCATTCTGAAGGGCGCTCTGGCCG
AAGTGCAGTTGGTTGAATCTGGTGGCGGATTGGTGCAGCCTGGCGGATCTCTGAGA
CTGTCTTGTGCCGCCTCTGGCTACGATTTCACCCACTACGGCATGAATTGGGTCCGA
CAGGCTCCTGGCAAAGGCCTGGAATGGGTCGGATGGATCAATACCTATACCGGCGA
GCCTACCTACGCCGCCGACTTCAAGAGAAGATTCACCTTCTCCCTGGACACCTCCAA
GTCTACCGCCTACCTGCAGATGAACTCCCTGAGAGCTGAGGACACCGCCGTGTACT
ACTGCGCTAAGTACCCCTACTACTACGGCACCAGCCACTGGTACTTTGATGTGTGGG
GACAGGGCACCCTGGTCACCGTTTCTTCCGCTTCTACAAAGGGACCCAGCGTGTTC
CCTCTGGCTCCAGCTCTAAGTCTACCTCTGGCGGAACCGCTGCTCTGGGCTGTCTG
GTCAAGGATTACTTCCCTGAGCCTGTGACCGTGTCCTGGAATAGTGGTGCTCTGACA
TCCGGCGTGCACACCTTTCCAGCTGTGCTGCAGTCCTCTGGCCTGTACTCTCTGTCC
TCTGTCGTGACCGTCCCTTCTAGCTCTCTGGGCACCCAGACCTACATCTGCAACGTG
AACCACAAGCCTTCCAACACTAAGGTGGACAAGAAGGTGGAACCCAAGTCCTGCGAT
AAGACCCACACCTGTCCTCCATGTCCTGCACCTGAAGCTGCTGGCGGACCCTCTGT
GTTCCTGTTTCCTCCAAAGCCTAAGGACACCCTGATGATCTCTCGGACCCCTGAAGT
GACCTGCGTGGTGGTGGATGTGTCTCACGAGGACCCAGAAGTGAAGTTCAATTGGT
ACGTGGACGGCGTGGAAGTGCACAACGCCAAGACCAAGCCTAGAGAGGAACAGTAC
AACTCCACCTACAGAGTGGTGTCCGTGCTGACCGTGCTGCACCAGGATTGGCTGAA
CGGCAAAGAGTACAAGTGCAAGGTGTCCAACAAGGCCCTGCCTGCTCCTATCGAAA
AGACCATCTCTAAGGCTAAGGGCCAGCCTCGGGAACCTCAGGTTTACACACTGCCTC
CAAGCCGGGAAGAGATGACCAAGAATCAGGTGTCCCTGACCTGCCTCGTGAAGGGC
TTCTACCCTTCCGATATCGCCGTGAATGGGAGTCCAATGGCCAGCCTGAGAACAAC
TACAAGACAACCCCTCCTGTGCTGGACTCCGACGGCTCATTCTTCCTGTACTCCAAG
CTGACAGTGGACAAGTCTCGGTGGCAGCAGGGCAACGTGTTCTCCTGTTCTGTGAT
GCACGAGGCCCTGCACAACCACTACACACAGAAGTCACTCTCCCTTTCCCCGGGCgc
tGGCGGCGGAGGATCTGCTCAGACCAACTTCATGCCTATGGACGACCTGGAACAGC
GGCTGTACGAGCAGTTCATCCTGCAGCAAGGACTGGAAtga SEQ ID NO: 47 7120_C terminal L7_1xGS_Protein sequence
MEFGLSWLFLVAILKGALAEVQLVESGGGLVQPGGSLRLSCAASGYDFTHYGMNWVRQAP
GKGLEWVGWINTYTGEPTYAADFKRRFTFSLDTSKSTAYLQMNSLRAEDTAVYYCAKYP
YYYGTSHWYFDVWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKV
DKKVEPKSCDKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPG
AGGGGSAQTNFMPMDDLEQRLYEQFILQQGLE*

SEQ ID NO: 48 7120_L7_C_2xGS_DNA sequence
ATGGAATTCGGCCTGTCTTGGCTGTTCCTGGTGGCCATTCTGAAGGGCGCTCTGGCCG
AAGTGCAGTTGGTTGAATCTGGTGGCGGATTGGTGCAGCCTGGCGGATCTCTGAGA
CTGTCTTGTGCCGCCTCTGGCTACGATTTCACCCACTACGGCATGAATTGGGTCCGA
CAGGCTCCTGGCAAAGGCCTGGAATGGGTCGGATGGATCAATACCTATACCGGCGA
GCCTACCTACGCCGCCGACTTCAAGAGAAGATTCACCTTCTCCCTGGACACCTCCAA
GTCTACCGCCTACCTGCAGATGAACTCCCTGAGAGCTGAGGACACCGCCGTGTACT
ACTGCGCTAAGTACCCCTACTACTACGGCACCAGCCACTGGTACTTTGATGTGTGGG
GACAGGGCACCCTGGTCACCGTTTCTTCCGCTTCTACAAAGGGACCCAGCGTGTTC
CCTCTGGCTCCAGCTCTAAGTCTACCTCTGGCGGAACCGCTGCTCTGGGCTGTCTG
GTCAAGGATTACTTCCCTGAGCCTGTGACCGTGTCCTGGAATAGTGGTGCTCTGACA
TCCGGCGTGCACACCTTTCCAGCTGTGCTGCAGTCCTCTGGCCTGTACTCTCTGTCC
TCTGTCGTGACCGTCCCTTCTAGCTCTCTGGGCACCCAGACCTACATCTGCAACGTG
AACCACAAGCCTTCCAACACTAAGGTGGACAAGAAGGTGGAACCCAAGTCCTGCGAT
AAGACCCACACCTGTCCTCCATGTCCTGCACCTGAAGCTGCTGGCGGACCCTCTGT
GTTCCTGTTTCCTCCAAAGCCTAAGGACACCCTGATGATCTCTCGGACCCCTGAAGT
GACCTGCGTGGTGGTGGATGTGTCTCACGAGGACCCAGAAGTGAAGTTCAATTGGT
ACGTGGACGGCGTGGAAGTGCACAACGCCAAGACCAAGCCTAGAGAGGAACAGTAC
AACTCCACCTACAGAGTGGTGTCCGTGCTGACCGTGCTGCACCAGGATTGGCTGAA
```

-continued

CGGCAAAGAGTACAAGTGCAAGGTGTCCAACAAGGCCCTGCCTGCTCCTATCGAAA
AGACCATCTCTAAGGCTAAGGGCCAGCCTCGGGAACCTCAGGTTTACACACTGCCTC
CAAGCCGGGAAGAGATGACCAAGAATCAGGTGTCCCTGACCTGCCTCGTGAAGGGC
TTCTACCCTTCCGATATCGCCGTCGAATGGGAGTCCAATGGCCAGCCTGAGAACAAC
TACAAGACAACCCCTCCTGTGCTGGACTCCGACGGCTCATTCTTCCTGTACTCCAAG
CTGACAGTGGACAAGTCTCGGTGGCAGCAGGGCAACGTGTTCTCCTGTTCTGTGAT
GCACGAGGCCCTGCACAACCACTACACACAGAAGTCACTCTCCCTTTCCCCGGGCgc
tGGCGGCGGAGGATCTGGCGGAGGCGGTAGCGCTCAGACCAACTTCATGCCTATGG
ACGACCTGGAACAGCGGCTGTACGAGCAGTTCATCCTGCAGCAAGGACTGGAAtga SEQ ID NO: 49 7120_L7_C_2xGS_protein sequence
MEFGLSWLFLVAILKGALAEVQLVESGGGLVQPGGSLRLSCAASGYDFTHYGMNWVRQAP
GKGLEWVGWINTYTGEPTYAADFKRRFTFSLDTSKSTAYLQMNSLRAEDTAVYYCAKYP
YYYGTSHWYFDVWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKV
DKKVEPKSCDKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPG
AGGGGSGGGGSAQTNFMPMDDLEQRLYEQFILQQGLE SEQ ID NO: 50 7120_L7_C_3xGS_DNA sequence
ATGGAATTCGGCCTGTCTTGGCTGTTCCTGGTGGCCATTCTGAAGGGCGCTCTGGCCG
AAGTGCAGTTGGTTGAATCTGGTGGCGGATTGGTGCAGCCTGGCGGATCTCTGAGA
CTGTCTTGTGCCGCCTCTGGCTACGATTTCACCCACTACGGCATGAATTGGGTCCGA
CAGGCTCCTGGCAAAGGCCTGGAATGGGTCGGATGGATCAATACCTATACCGGCGA
GCCTACCTACGCCGCCGACTTCAAGAGAAGATTCACCTTCTCCCTGGACACCTCCAA
GTCTACCGCCTACCTGCAGATGAACTCCCTGAGAGCTGAGGACACCGCCGTGTACT
ACTGCGCTAAGTACCCCTACTACTACGGCACCAGCCACTGGTACTTTGATGTGTGGG
GACAGGGCACCCTGGTCACCGTTTCTTCCGCTTCTACAAAGGGACCCAGCGTGTTC
CCTCTGGCTCCTAGCTCTAAGTCTACCTCTGGCGGAACCGCTGCTCTGGGCTGTCTG
GTCAAGGATTACTTCCCTGAGCCTGTGACCGTGTCCTGGAATAGTGGTGCTCTGACA
TCCGGCGTGCACACCTTTCCAGCTGTGCTGCAGTCCTCTGGCCTGTACTCTCTGTCC
TCTGTCGTGACCGTCCCTTCTAGCTCTCTGGGCACCCAGACCTACATCTGCAACGTG
AACCACAAGCCTTCCAACACTAAGGTGGACAAGAAGGTGGAACCCAAGTCCTGCGAT
AAGACCCACACCTGTCCTCCATGTCCTGCACCTGAAGCTGCTGGCGGACCCTCTGT
GTTCCTGTTTCCTCCAAAGCCTAAGGACACCCTGATGATCTCTCGGACCCCTGAAGT
GACCTGCGTGGTGGTGGATGTGTCTCACGAGGACCCAGAAGTGAAGTTCAATTGGT
ACGTGGACGGCGTGGAAGTGCACAACGCCAAGACCAAGCCTAGAGAGGAACAGTAC
AACTCCACCTACAGAGTGGTGTCCGTGCTGACCGTGCTGCACCAGGATTGGCTGAA
CGGCAAAGAGTACAAGTGCAAGGTGTCCAACAAGGCCCTGCCTGCTCCTATCGAAA
AGACCATCTCTAAGGCTAAGGGCCAGCCTCGGGAACCTCAGGTTTACACACTGCCTC
CAAGCCGGGAAGAGATGACCAAGAATCAGGTGTCCCTGACCTGCCTCGTGAAGGGC
TTCTACCCTTCCGATATCGCCGTCGAATGGGAGTCCAATGGCCAGCCTGAGAACAAC
TACAAGACAACCCCTCCTGTGCTGGACTCCGACGGCTCATTCTTCCTGTACTCCAAG
CTGACAGTGGACAAGTCTCGGTGGCAGCAGGGCAACGTGTTCTCCTGTTCTGTGAT
GCACGAGGCCCTGCACAACCACTACACACAGAAGTCACTCTCCCTTTCCCCGGGCgc
tGGCGGCGGAGGATCTGGCGGAGGCGGTAGCGGTGGTGGTGGATCTGCTCAGACC
AACTTCATGCCTATGGACGACCTGGAACAGCGGCTGTACGAGCAGTTCATCCTGCAG
CAAGGACTGGAAtga >SEQ ID NO: 51 7120_L7_C_3xGS_Protein sequence
MEFGLSWLFLVAILKGALAEVQLVESGGGLVQPGGSLRLSCAASGYDFTHYGMNWVRQAP
GKGLEWVGWINTYTGEPTYAADFKRRFTFSLDTSKSTAYLQMNSLRAEDTAVYYCAKYP
YYYGTSHWYFDVWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKV
DKKVEPKSCDKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPG
AGGGGSGGGGSGGGGSAQTNFMPMDDLEQRLYEQFILQQGLE SEQ ID NO: 52 7120_L15_C_1xGS_DNA sequence
ATGGAATTCGGCCTGTCTTGGCTGTTCCTGGTGGCCATTCTGAAGGGCGCTCTGGC
CGAAGTGCAGTTGGTTGAATCTGGTGGCGGATTGGTGCAGCCTGGCGGATCTCTGA
GACTGTCTTGTGCCGCCTCTGGCTACGATTTCACCCACTACGGCATGAATTGGGTCC
GACAGGCTCCTGGCAAAGGCCTGGAATGGGTCGGATGGATCAATACCTATACCGGC
GAGCCTACCTACGCCGCCGACTTCAAGAGAAGATTCACCTTCTCCCTGGACACCTCC
AAGTCTACCGCCTACCTGCAGATGAACTCCCTGAGAGCTGAGGACACCGCCGTGTA
CTACTGCGCTAAGTACCCCTACTACTACGGCACCAGCCACTGGTACTTTGATGTGTG
GGGACAGGGCACCCTGGTCACCGTTTCTTCCGCTTCTACAAAGGGACCCAGCGTGT
TCCCTCTGGCTCCTAGCTCTAAGTCTACCTCTGGCGGAACCGCTGCTCTGGGCTGTC
TGGTCAAGGATTACTTCCCTGAGCCTGTGACCGTGTCCTGGAATAGTGGTGCTCTGA
CATCCGGCGTGCACACCTTTCCAGCTGTGCTGCAGTCCTCTGGCCTGTACTCTCTGT
CCTCTGTCGTGACCGTCCCTTCTAGCTCTCTGGGCACCCAGACCTACATCTGCAACG
TGAACCACAAGCCTTCCAACACTAAGGTGGACAAGAAGGTGGAACCCAAGTCCTGC
GATAAGACCCACACCTGTCCTCCATGTCCTGCACCTGAAGCTGCTGGCGGACCCTCT
GTGTTCCTGTTTCCTCCAAAGCCTAAGGACACCCTGATGATCTCTCGGACCCCTGAA
GTGACCTGCGTGGTGGTGGATGTGTCTCACGAGGACCCAGAAGTGAAGTTCAATTG
GTACGTGGACGGCGTGGAAGTGCACAACGCCAAGACCAAGCCTAGAGAGGAACAGT
ACAACTCCACCTACAGAGTGGTGTCCGTGCTGACCGTGCTGCACCAGGATTGGCTG

```
-continued
AACGGCAAAGAGTACAAGTGCAAGGTGTCCAACAAGGCCCTGCCTGCTCCTATCGA
AAAGACCATCTCTAAGGCTAAGGGCCAGCCTCGGGAACCTCAGGTTTACACACTGCC
TCCAAGCCGGGAAGAGATGACCAAGAATCAGGTGTCCCTGACCTGCCTCGTGAAGG
GCTTCTACCCTTCCGATATCGCCGTCGAATGGGAGTCCAATGGCCAGCCTGAGAACA
ACTACAAGACAACCCCTCCTGTGCTGGACTCCGACGGCTCATTCTTCCTGTACTCCA
AGCTGACAGTGGACAAGTCTCGGTGGCAGCAGGGCAACGTGTTCTCCTGTTCTGTG
ATGCACGAGGCCCTGCACAACCACTACACACAGAAGTCACTCTCCCTTTCCCCGGG
CgctGGCGGCGGAGGATCTGCCCAGCAGAAGTATCAGCCTCTGGACGAGCTGGACAA
GACCCTGTACGACCAGTTCATGCTCCAGCAGGGACTGGAAtga
```

SEQ ID NO: 53 7120_L15_C_1xGS_Protein sequence
MEFGLSWLFLVAILKGALAEVQLVESGGGLVQPGGSLRLSCAASGYDFTHYGMNWVRQAP
GKGLEWVGWINTYTGEPTYAADFKRRFTFSLDTSKSTAYLQMNSLRAEDTAVYYCAKYP
YYYGTSHWYFDVWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKV
DKKVEPKSCDKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPG
AGGGGSAQQKYQPLDELDKTLYDQFMLQQGLE SEQ ID NO: 54 7120_L15_C_2xGS_DNA sequence
```
TGGAATTCGGCCTGTCTTGGCTGTTCCTGGTGGCCATTCTGAAGGGCGCTCTGGCC
GAAGTGCAGTTGGTTGAATCTGGTGGCGGATTGGTGCAGCCTGGCGGATCTCTGAG
ACTGTCTTGTGCCGCCTCTGGCTACGATTTCACCCACTACGGCATGAATTGGGTCCG
ACAGGCTCCTGGCAAAGGCCTGGAATGGGTCGGATGGATCAATACCTATACCGGCG
AGCCTACCTACGCCGCCGACTTCAAGAGAAGATTCACCTTCTCCCTGGACACCTCCA
AGTCTACCGCCTACCTGCAGATGAACTCCCTGAGAGCTGAGGACACCGCCGTGTAC
TACTGCGCTAAGTACCCCTACTACTACGGCACCAGCCACTGGTACTTTGATGTGTGG
GGACAGGGCACCCTGGTCACCGTTTCTTCCGCTTCTACAAAGGGACCCAGCGTGTT
CCCTCTGGCTCCTAGCTCTAAGTCTACCTCTGGCGGAACCGCTGCTCTGGGCTGTCT
GGTCAAGGATTACTTCCCTGAGCCTGTGACCGTGTCCTGGAATAGTGGTGCTCTGAC
ATCCGGCGTGCACACCTTTCCAGCTGTGCTGCAGTCCTCTGGCCTGTACTCTCTGTC
CTCTGTCGTGACCGTCCCTTCTAGCTCTCTGGGCACCCAGACCTACATCTGCAACGT
GAACCACAAGCCTTCCAACACTAAGGTGGACAAGAAGGTGGAACCCAAGTCCTGCG
ATAAGACCCACACCTGTCCTCCATGTCCTGCACCTGAAGCTGCTGGCGGACCCTCTG
TGTTCCTGTTTCCTCCAAAGCCTAAGGACACCCTGATGATCTCTCGGACCCCTGAAG
TGACCTGCGTGGTGGTGGATGTGTCTCACGAGGACCCAGAAGTGAAGTTCAATTGG
TACGTGGACGGCGTGGAAGTGCACAACGCCAAGACCAAGCCTAGAGAGGAACAGTA
CAACTCCACCTACAGAGTGGTGTCCGTGCTGACCGTGCTGCACCAGGATTGGCTGA
ACGGCAAAGAGTACAAGTGCAAGGTGTCCAACAAGGCCCTGCCTGCTCCTATCGAA
AAGACCATCTCTAAGGCTAAGGGCCAGCCTCGGGAACCTCAGGTTTACACACTGCCT
CCAAGCCGGGAAGAGATGACCAAGAATCAGGTGTCCCTGACCTGCCTCGTGAAGGG
CTTCTACCCTTCCGATATCGCCGTCGAATGGGAGTCCAATGGCCAGCCTGAGAACAA
CTACAAGACAACCCCTCCTGTGCTGGACTCCGACGGCTCATTCTTCCTGTACTCCAA
GCTGACAGTGGACAAGTCTCGGTGGCAGCAGGGCAACGTGTTCTCCTGTTCTGTGA
TGCACGAGGCCCTGCACAACCACTACACACAGAAGTCACTCTCCCTTTCCCCGGGCg
ctGGCGGCGGAGGATCTGGCGGAGGCGGTAGCGCCCAGCAGAAGTATCAGCCTCTG
GACGAGCTGGACAAGACCCTGTACGACCAGTTCATGCTCCAGCAGGGACTGGAAtga
```

SEQ ID NO: 55 7120_L15_C_2xGS_Protein sequence
MEFGLSWLFLVAILKGALAEVQLVESGGGLVQPGGSLRLSCAASGYDFTHYGMNWVRQ
APGKGLEWVGWINTYTGEPTYAADFKRRFTFSLDTSKSTAYLQMNSLRAEDTAVYYCAK
YPYYYGTSHWYFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNT
KVDKKVEPKSCDKTHTCPPCPAPEAAGGPSVFLFPPKPKDTLMISRTPEVTCVVVDVSH
EDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSLS
PGAGGGGSGGGGSAQQKYQPLDELDKTLYDQFMLQQGLE SEQ ID NO: 56 7120_L15_C_3xGS_DNA sequence
```
ATGGAATTCGGCCTGTCTTGGCTGTTCCTGGTGGCCATTCTGAAGGGCGCTCTGGC
CGAAGTGCAGTTGGTTGAATCTGGTGGCGGATTGGTGCAGCCTGGCGGATCTCTGA
GACTGTCTTGTGCCGCCTCTGGCTACGATTTCACCCACTACGGCATGAATTGGGTCC
GACAGGCTCCTGGCAAAGGCCTGGAATGGGTCGGATGGATCAATACCTATACCGGC
GAGCCTACCTACGCCGCCGACTTCAAGAGAAGATTCACCTTCTCCCTGGACACCTCC
AAGTCTACCGCCTACCTGCAGATGAACTCCCTGAGAGCTGAGGACACCGCCGTGTA
CTACTGCGCTAAGTACCCCTACTACTACGGCACCAGCCACTGGTACTTTGATGTGTG
GGGACAGGGCACCCTGGTCACCGTTTCTTCCGCTTCTACAAAGGGACCCAGCGTGT
TCCCTCTGGCTCCTAGCTCTAAGTCTACCTCTGGCGGAACCGCTGCTCTGGGCTGTC
TGGTCAAGGATTACTTCCCTGAGCCTGTGACCGTGTCCTGGAATAGTGGTGCTCTGA
CATCCGGCGTGCACACCTTTCCAGCTGTGCTGCAGTCCTCTGGCCTGTACTCTCTGT
CCTCTGTCGTGACCGTCCCTTCTAGCTCTCTGGGCACCCAGACCTACATCTGCAACG
TGAACCACAAGCCTTCCAACACTAAGGTGGACAAGAAGGTGGAACCCAAGTCCTGC
GATAAGACCCACACCTGTCCTCCATGTCCTGCACCTGAAGCTGCTGGCGGACCCTCT
GTGTTCCTGTTTCCTCCAAAGCCTAAGGACACCCTGATGATCTCTCGGACCCCTGAA
GTGACCTGCGTGGTGGTGGATGTGTCTCACGAGGACCCAGAAGTGAAGTTCAATTG
GTACGTGGACGGCGTGGAAGTGCACAACGCCAAGACCAAGCCTAGAGAGGAACAGT
ACAACTCCACCTACAGAGTGGTGTCCGTGCTGACCGTGCTGCACCAGGATTGGCTG
AACGGCAAAGAGTACAAGTGCAAGGTGTCCAACAAGGCCCTGCCTGCTCCTATCGA
```

-continued

AAAGACCATCTCTAAGGCTAAGGGCCAGCCTCGGGAACCTCAGGTTTACACACTGCC
TCCAAGCCGGGAAGAGATGACCAAGAATCAGGTGTCCCTGACCTGCCTCGTGAAGG
GCTTCTACCCTTCCGATATCGCCGTCGAATGGGAGTCCAATGGCCAGCCTGAGAACA
ACTACAAGACAACCCCTCCTGTGCTGGACTCCGACGGCTCATTCTTCCTGTACTCCA
AGCTGACAGTGGACAAGTCTCGGTGGCAGCAGGGCAACGTGTTCTCCTGTTCTGTG
ATGCACGAGGCCCTGCACAACCACTACACACAGAAGTCACTCTCCCTTTCCCCGGG
CgctGGCGGCGGAGGATCTGGCGGAGGCGGTAGCGGTGGTGGTGGATCTGCCCAGC
AGAAGTATCAGCCTCTGGACGAGCTGGACAAGACCCTGTACGACCAGTTCATGCTCC
AGCAGGGACTGGAAtga SEQ ID NO 57, DNA sequence (DHAMDH02083016) for 2xCon4(C) fused to the
C-terminus of the Heavy Chain of Bevacizumab, with linker peptide
GGGGSGGGGSGGGGS
ATGGGTTGGTCCTGTATCATTCTTTTCCTCGTCGCCACTGCCACCGGAGTCCACTCAGA
AGTCCAGTTGGTGGAGTCGGGAGGAGGACTGGTGCAGCCAGGCGGCTCCCTGCGC
CTGTCCTGCGCGGCCGTCCGGGTACACCTTCACCAACTACGGCATGAACTGGGTCCG
CCAGGCCCCCGGAAAGGGGCTGGAATGGGTCGGCTGGATCAACACTTACACCGGA
GAACCTACCTACGCTGCCGATTTCAAGCGGCGCTTTACTTTCTCGCTGGACACCTCC
AAGAGCACCGCCTATCTCCAAATGAACTCCCTGCGGGCCGAGGATACCGCCGTGTA
CTATTGCGCGAAGTACCCCCACTATTACGGTTCGTCCCATTGGTACTTCGACGTCTG
GGGCCAGGGAACTCTTGTCACTGTGTCCTCCGCATCCACCAAGGGACCGTCAGTGT
TCCCCCTGGCCCCGTCCTCCAAAAGCACTAGCGGAGGAACCGCAGCCTTGGGATGC
CTCGTCAAGGACTACTTTCCCGAGCCTGTCACCGTGTCGTGGAACTCCGGTGCCCT
CACTTCGGGCGTGCACACGTTCCCAGCGGTGCTGCAGTCCAGCGGACTGTACTCGC
TGTCCTCCGTCGTGACCGTGCCTTCATCGAGCCTGGGGACCCAGACCTACATTTGCA
ACGTGAACCACAAGCCCTCCAACACCAAAGTGGACAAGAAGGTCGAACCAAAGAGC
TGCGACAAGACCCACACTTGCCCGCCGTGCCCGGCCCCTGAGTTGCTGGGTGGTCC
ATCGGTGTTCCTGTTCCCGCCTAAGCCGAAGGACACACTCATGATCAGCAGGACCC
CCGAAGTGACCTGTGTGGTGGTCGACGTGTCACATGAAGATCCCGAGGTCAAGTTC
AATTGGTACGTGGACGGAGTGGAAGTGCATAATGCCAAGACTAAGCCGAGAGAGGA
ACAGTACAACTCCACCTACCGGGTGGTGTCAGTGCTGACCGTGCTCCATCAGGACT
GGCTCAACGGGAAGGAGTACAAGTGCAAAGTGTCGAACAAGGCTCTCCCCGCCCCT
ATCGAGAAACCATTAGCAAGGCTAAGGGACAGCCGCGGGAGCCGCAAGTGTACAC
CCTGCCCCCGAGCCGCGAAGAAATGACTAAGAACCAAGTGTCCCTGACCTGTCTCG
TGAAAGGGTTCTACCCGTCGGACATCGCTGTGGAGTGGGAGTCTAATGGTCAACCT
GAGAACAACTACAAGACTACTCCCCCTGTGCTGGACTCCGATGGTTCCTTTTTCCTG
TACTCAAAGCTGACCGTGGACAAGTCCAGATGGCAGCAGGGCAACGTGTTCAGCTG
CTCCGTGATGCATGAAGCACTTCACAACCACTACACCCAGAAGTCCCTCAGCCTGTC
TCCGGGGAAGGGCGGCGGAGGAGGGGCCCAGCAGGAAGAGTGTGAATGGGACCC
CTGGACTTGTGAACACATGGGCGGCGGCGGCTCCGGTGGAGGAGGATCCGGCGGA
GGGGGCAGCGCGACGCACCAGGAGGAGTGCGAATGGGATCCATGGACTTGCGAAC
ACATGCTGGAGTGA SEQ ID NO 58, DNA sequence (DHAMDL083016), for the light chain of
Bevacizumab
ATGGGTTGGTCCTGTATTATCCTCTTTCTCGTCGCCACTGCCACCGGAGTGCACTCAGA
TATTCAGATGACCCAGAGCCCCTCCTCACTGTCCGCTTCCGTGGGGGACCGCGTGA
CTATCACTTGCTCGGCTTCCCAAGATATCTCCAACTACCTGAACTGGTACCAGCAGA
AGCCCGGAAAGGCCCCGAAAGTGCTCATCTACTTCACCTCATCGCTGCACTCGGGA
GTGCCCTCAAGATTTTCCGGCTCCGGAAGCGGGACCGACTTCACTCTTACCATCTCA
TCGTTGCAACCAGAGGATTTCGCGACCTACTACTGTCAGCAGTACTCCACGGTGCCG
TGGACCTTCGGACAAGGCACCAAAGTGGAGATCAAGAGGACTGTGGCGGCCCCGA
GCGTGTTCATTTTCCCTCCTTCCGACGAGCAGCTGAAAGCGGCACCGCCTCGGTC
GTGTGCCTCCTGAACAACTTCTACCCGCGGGAAGCCAAGGTCCAGTGGAAGGTCGA
CAACGCGCTGCAGAGCGGAAATTCCCAGGAGAGCGTGACCGAACAGGACTCCAAG
GACAGCACCTATTCCCTGTCGTCTACACTGACCCTGAGCAAGGCCGACTACGAGAA
GCATAAGGTCTACGCATGCGAAGTGACCCACCAAGGTCTTTCCTCCCCTGTGACCAA
GTCCTTCAACCGGGGCGAATGCTGA SEQ ID NO 59, DNA sequence (LY2.55.1), for peptide L1-15 (no LE) fused to
the N-terminus of the light chain of Bevacizumab
ATGGCCTGGATGATGTTGCTTCTCGGACTTCTCGCGTATGGATCAGGGGTGGATAGCG
CGCAACAGAAGTACCAGCCTTTGGACGAACTGGACAAGACCCTGTACGACCAGTTCA
TGCTGCAACAGGGAGGGGCCGGTGGATCCGGGGCGGCGGCTCCGGCGGTGGCG
GATCCGACATTCAAATGACTCAGTCGCCATCGTCCCTCTCGGCATCCGTGGGAGACA
GAGTGACCATCACTTGTTCCGCCTCGCAAGACATCTCCAACTACCTGAACTGGTACC
AGCAGAAGCCCGGGAAGGCCCCCAAAGTGCTCATCTACTTTACTTCCTCACTGCACT
CCGGGGGTGCCAAGCCGCTTTAGCGGCTCCGGTTCTGGAACCGATTTCACCCTGACC
ATTAGCTCACTCCAGCCGGAAGATTTCGCTACGTACTACTGCCAGCAGTATTCGACC
GTGCCGTGGACTTTCGGACAGGGTACCAAAGTCGAGATCAAGCGGACCGTGGCCGC
CCCGAGCGTGTTCATTTTCCCGCCTTCCGACGAGCAACTCAAGTCCGGCACTGCCTC
CGTGGTCTGCCTGCTGAACAATTTCTACCCCCGCGAGGCTAAGGTCCAGTGGAAGG
TCGATAACGCACTGCAGTCCGGAAACAGCCAAGAGAGCGTGACCGAACAGGACTCC
AAGGACTCAACTTACTCGCTGAGCTCCACCCTGACCCTGTCGAAGGCCGACTACGAA
AAGCACAAAGTGTACGCCTGCGAAGTGACACATCAGGGCCTGTCATCCCCTGTCAC
CAAGTCCTTCAACCGGGGAGAGTGCTGATAA SEQ ID NO 60, DNA sequence (LY2.55.2), for peptide L1-15 (with LE) fused to
the N-terminus of the light chain of Bevacizumab
ATGGCCTGGATGATGTTGCTTCTCGGACTTCTCGCGTATGGATCAGGGGTGGATAGCG
CGCAACAGAAGTACCAGCCTTTGGACGAACTGGACAAGACCCTGTACGACCAGTTCA -continued
TGCTGCAACAGGGACTGGAAGGGGCGGTGGATCCGGGGCGGCGGCTCCGGCG
GTGGCGGATCCGACATTCAAATGACTCAGTCGCCATCGTCCCTCTCGGCATCCGTG
GGAGACAGAGTGACCATCACTTGTTCCGCCTCGCAAGACATCTCCAACTACCTGAAC
TGGTACCAGCAGAAGCCCGGGAAGGCCCCCAAAGTGCTCATCTACTTTACTTCCTCA
CTGCACTCCGGGGTGCCAAGCCGCTTTAGCGGCTCCGGTTCTGGAACCGATTTCAC
CCTGACCATTAGCTCACTCCAGCCGGAAGATTTCGCTACGTACTACTGCCAGCAGTA
TTCGACCGTGCCGTGGACTTTCGGACAGGGTACCAAAGTCGAGATCAAGCGGACCG
TGGCCGCCCCGAGCGTGTTCATTTTCCCGCCTTCCGACGAGCAACTCAAGTCCGGC
ACTGCCTCCGTGGTCTGCCTGCTGAACAATTTCTACCCCCGCGAGGCTAAGGTCCA
GTGGAAGGTCGATAACGCACTGCAGTCCGGAAACAGCCAAGAGAGCGTGACCGAAC
AGGACTCCAAGGACTCAACTTACTCGCTGAGCTCCACCCTGACCCTGTCGAAGGCC
GACTACGAAAAGCACAAAGTGTACGCCTGCGAAGTGACACATCAGGGCCTGTCATC
CCCTGTCACCAAGTCCTTCAACCGGGGAGAGTGCTGATAA SEQ ID NO 61, DNA sequence (LY2.55.3), for peptide L1-15 (no LE) fused to
the N-terminus of the heavy chain of Bevacizumab
ATGGCTTGGATGATGCTGCTGCTTGGCCTTCTCGCATACGGTTCCGGAGTCGATAGCG
CCCAACAGAAGTACCAGCCTCTGGACGAACTGGATAAGACCCTGTACGATCAGTTCA
TGCTGCAACAGGGGGGCGGCGAGGATCGGCGGTGGTGGATCCGGCGGCGGCG
GATCCGAAGTGCAGCTCGTGGAGAGCGGGGGCGGACTCGTGCAGCCGGGAGGTTC
GCTGAGATTGTCCTGTGCCGCCTCCGGTTACACCTTTACCAATTACGGGATGAACTG
GGTCCGCCAGGCCCCCGGAAAGGGACTGGAATGGGTCGGCTGGATCAACACATATA
CCGGAGAGCCCACCTACGCCGCGGACTTCAAGCGGAGATTCACCTTTTCACTGGAT
ACGTCAAAGTCAACTGCATACCTCCAGATGAACTCCCTTAGGGCGGAAGATACCGCC
GTGTACTACTGCGCCAAGTACCCGCACTATTACGGGTCCAGCCATTGGTACTTCGAC
GTCTGGGGACAGGGGACCCTCGTGACCGTCAGCAGCGCCTCCACCAAGGGCCCGT
CCGTGTTCCCTCTTGCGCCGTCGTCCAAAAGCACTTCCGGCGGCACTGCCGCCCTG
GGCTGCCTCGTGAAGGATTACTTCCCGGAACCGGTCACCGTGTCGTGGAACTCCGG
AGCCCTGACTTCGGGTGTCCACACCTTCCCTGCGGTGCTGCAGAGCTCCGGTCTGT
ACTCCCTCTCTTCCGTGGTCACGGTGCCCTCCTCATCACTGGGAACCCAGACCTACA
TCTGCAACGTGAACCACAAGCCCTCAAACACTAAGGTCGACAAGAAAGTCGAACCGA
AGTCGTGCGACAAGACCCACACTTGCCCTCCGTGCCCGGCTCCCGAGCTGCTGGG
GGGCCCTTCCGTGTTTTTGTTCCCGCCGAAACCAAAGGACACTCTGATGATCAGCCG
CACTCCGGAAGTGACCTGTGTGGTGGTGGACGTGTCCCACGAGGACCCAGAAGTGA
AATTCAATTGGTACGTGGATGGCGTGGAAGTGCACAACGCTAAGACTAAGCCCCGC
GAGGAACAGTACAACAGCACTTACCGGGTGGTGTCGGTGCTCACCGTGCTGCACCA
AGATTGGCTCAACGGGAAGGAGTACAAGTGCAAAGTCTCCAACAAGGCCCTGCCCG
CACCTATTGAAAAGACCATCAGCAAGGCCAAGGGACAGCCCCGGGAGCCCCAGGTC
TACACCCTGCCTCCCTCGCGCGAAGAGATGACTAAGAACCAAGTGTCCCTGACCTGT
CTGGTCAAGGGATTCTATCCTTCCGACATTGCCGTGGAATGGGAGTCCAACGGGCA
GCCAGAGAACAACTACAAGACCACTCCACCTGTGCTGGACTCCGACGGGTCCTTCTT
CTTGTACTCGAAGCTGACCGTGGACAAGTCCCGGTGGCAGCAGGGAAACGTGTTCA
GCTGCTCCGTGATGCACGAGGCCTTGCATAATCATTACACCCAAAAGTCGCTGAGCT
TGAGCCCGGGAAAGTGATAA SEQ ID NO 62, DNA sequence (LY2.55.4), for peptide L1-15 (with LE) fused to
the N-terminus of the heavy chain of Bevacizumab
ATGGCTTGGATGATGCTGCTGCTTGGCCTTCTCGCATACGGTTCCGGAGTCGATAGCG
CCCAACAGAAGTACCAGCCTCTGGACGAACTGGATAAGACCCTGTACGATCAGTTCA
TGCTGCAACAGGGGCTTGAGGGCGGCGGAGGATCGGCGGTGGTGGATCCGGCG
GCGGCGGATCCGAAGTGCAGCTCGTGGAGAGCGGGGGCGGACTCGTGCAGCCGG
GAGGTTCGCTGAGATTGTCCTGTGCCGCCTCCGGTTACACCTTTACCAATTACGGGA
TGAACTGGGTCCGCCAGGCCCCCGGAAAGGGACTGGAATGGGTCGGCTGGATCAA
CACATATACCGGAGAGCCCACCTACGCCGCGGACTTCAAGCGGAGATTCACCTTTTC
ACTGGATACGTCAAAGTCAACTGCATACCTCCAGATGAACTCCCTTAGGGCGGAAGA
TACCGCCGTGTACTACTGCGCCAAGTACCCGCACTATTACGGGTCCAGCCATTGGTA
CTTCGACGTCTGGGGACAGGGGACCCTCGTGACCGTCAGCAGCGCCTCCACCAAG
GGCCCGTCCGTGTTCCCTCTTGCGCCGTCGTCCAAAAGCACTTCCGGCGGCACTGC
CGCCCTGGGCTGCCTCGTGAAGGATTACTTCCCGGAACCGGTCACCGTGTCGTGGA
ACTCCGGAGCCCTGACTTCGGGTGTCCACACCTTCCCTGCGGTGCTGCAGAGCTCC
GGTCTGTACTCCCTCTCTTCCGTGGTCACGGTGCCCTCCTCATCACTGGGAACCCAG
ACCTACATCTGCAACGTGAACCACAAGCCCTCAAACACTAAGGTCGACAAGAAAGTC
GAACCGAAGTCGTGCGACAAGACCCACACTTGCCCTCCGTGCCCGGCTCCCGAGCT
GCTGGGGGGCCCTTCCGTGTTTTTGTTCCCGCCGAAACCAAAGGACACTCTGATGAT
CAGCCGCACTCCGGAAGTGACCTGTGTGGTGGTGGACGTGTCCCACGAGGACCCA
GAAGTGAAATTCAATTGGTACGTGGATGGCGTGGAAGTGCACAACGCTAAGACTAAG
CCCCGCGAGGAACAGTACAACAGCACTTACCGGGTGGTGTCGGTGCTCACCGTGCT
GCACCAAGATTGGCTCAACGGGAAGGAGTACAAGTGCAAAGTCTCCAACAAGGCCC
TGCCCGCACCTATTGAAAAGACCATCAGCAAGGCCAAGGGACAGCCCCGGGAGCCC
CAGGTCTACACCCTGCCTCCCTCGCGCGAAGAGATGACTAAGAACCAAGTGTCCCT
GACCTGTCTGGTCAAGGGATTCTATCCTTCCGACATTGCCGTGGAATGGGAGTCCAA
CGGGCAGCCAGAGAACAACTACAAGACCACTCCACCTGTGCTGGACTCCGACGGGT
CCTTCTTCTTGTACTCGAAGCTGACCGTGGACAAGTCCCGGTGGCAGCAGGGAAAC
GTGTTCAGCTGCTCCGTGATGCACGAGGCCTTGCATAATCATTACACCCAAAAGTCG
CTGAGCTTGAGCCCGGGAAAGTGATAA SEQ ID NO 63, DNA sequence (LY2.55.5), for the light chain of Bevacizumab
ATGGCCTGGATGATGTTGCTTCTCGGACTTCTCGCGTATGGATCAGGGGTGGACTCCG
ACATTCAAATGACTCAGTCGCCATCGTCCCTCTCGGCATCCGTGGGAGACAGAGTGA
CCATCACTTGTTCCGCCTCGCAAGACATCTCCAACTACCTGAACTGGTACCAGCAGA
AGCCCGGGAAGGCCCCCAAAGTGCTCATCTACTTTACTTCCTCACTGCACTCCGGG

```
GTGCCAAGCCGCTTTAGCGGCTCCGGTTCTGGAACCGATTTCACCCTGACCATTAGC
TCACTCCAGCCGGAAGATTTCGCTACGTACTACTGCCAGCAGTATTCGACCGTGCCG
TGGACTTTCGGACAGGGTACCAAAGTCGAGATCAAGCGGACCGTGGCCGCCCCCGAG
CGTGTTCATTTTCCCGCCTTCCGACGAGCAACTCAAGTCCGGCACTGCCTCCGTGGT
CTGCCTGCTGAACAATTTCTACCCCCGCGAGGCTAAGGTCCAGTGGAAGGTCGATAA
CGCACTGCAGTCCGGAAACAGCCAAGAGAGCGTGACCGAACAGGACTCCAAGGACT
CAACTTACTCGCTGAGCTCCACCCTGACCCTGTCGAAGGCCGACTACGAAAAGCACA
AAGTGTACGCCTGCGAAGTGACACATCAGGGCCTGTCATCCCCTGTCACCAAGTCCT
TCAACCGGGGAGAGTGCTGATAA
```

SEQ ID NO 64, 2xCon4(C) fused to the C-terminus of the VEGF Trap

```
           10         20         30         40         50         60
  SDTGRPFVEM YSEIPEIIHM TEGRELVIPC RVTSPNITVT LKKFPLDTLI PDGKRIIWDS 70         80         90        100        110        120
  RKGFIISNAT YKEIGLLTCE ATVNGHLYKT NYLTHRQTNT IIDVVLSPSH GIELSVGEKL 130        140        150        160        170        180
  VLNCTARTEL NVGIDFNWEY PSSKHQHKKL VNRDLKTQSG SEMKKFLSTL TIDGVTRSDQ 190        200        210        220        230        240
  GLYTCAASSG LMTKKNSTFV RVHEDKDTHT CPPCPAPELL GGPSVFLFPP KPKDTLMISR 250        260        270        280        290        300
  TPEVTCVVVD VSHEDPEVKF NWYVDGVEVH NAKTKPREEQ YNSTYRVVSV LTVLHQDWLN 310        320        330        340        350        360
  GKEYKCKVSN KALPAPIEKT ISKAKGQPRE PQVYTLPPSR DELTKNQVSL TCLVKGFYPS 370        380        390        400        410        420
  DIAVESESNG QPENNYKTTP PVLDSDGSFF LYSKLTVDKS RWQQGNVFSC SVMHEALHNH 430        440        450        460        470        480
  YTQKSLSLSP GKGGGGGAQQ EECEWDPWTC EHMGSGSATG GSGSTASSGS GSATHQEECE

490
  WDPWTCEHML E
```

---

SEQUENCE LISTING

<160> NUMBER OF SEQ ID NOS: 64

<210> SEQ ID NO 1
<211> LENGTH: 453
<212> TYPE: PRT
<213> ORGANISM: artificial
<220> FEATURE:
<223> OTHER INFORMATION: Bevacizumab Heavy Chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

-continued

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 2
<211> LENGTH: 214
<212> TYPE: PRT
<213> ORGANISM: artificial
<220> FEATURE:
<223> OTHER INFORMATION: Bevacizumab Light Chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45
```

Tyr Phe Thr Ser Ser Leu His Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 432
<212> TYPE: PRT
<213> ORGANISM: artificial
<220> FEATURE:
<223> OTHER INFORMATION: VEGF Trap Aflibercept

<400> SEQUENCE: 3

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
             35                  40                  45

Leu Ile Pro Asp Gly Lys Arg Ile Ile Trp Asp Ser Arg Lys Gly Phe
         50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

```
Thr Lys Lys Asn Ser Thr Phe Val Arg Val His Glu Lys Asp Lys Thr
            195                 200                 205
His Thr Cys Pro Pro Cys Pro Ala Pro Glu Leu Leu Gly Gly Pro Ser
        210                 215                 220
Val Phe Leu Phe Pro Pro Lys Pro Lys Asp Thr Leu Met Ile Ser Arg
225                 230                 235                 240
Thr Pro Glu Val Thr Cys Val Val Val Asp Val Ser His Glu Asp Pro
                245                 250                 255
Glu Val Lys Phe Asn Trp Tyr Val Asp Gly Val Glu Val His Asn Ala
            260                 265                 270
Lys Thr Lys Pro Arg Glu Glu Gln Tyr Asn Ser Thr Tyr Arg Val Val
        275                 280                 285
Ser Val Leu Thr Val Leu His Gln Asp Trp Leu Asn Gly Lys Glu Tyr
290                 295                 300
Lys Cys Lys Val Ser Asn Lys Ala Leu Pro Ala Pro Ile Glu Lys Thr
305                 310                 315                 320
Ile Ser Lys Ala Lys Gly Gln Pro Arg Glu Pro Gln Val Tyr Thr Leu
                325                 330                 335
Pro Pro Ser Arg Asp Glu Leu Thr Lys Asn Gln Val Ser Leu Thr Cys
            340                 345                 350
Leu Val Lys Gly Phe Tyr Pro Ser Asp Ile Ala Val Glu Trp Glu Ser
        355                 360                 365
Asn Gly Gln Pro Glu Asn Asn Tyr Lys Thr Thr Pro Pro Val Leu Asp
370                 375                 380
Ser Asp Gly Ser Phe Phe Leu Tyr Ser Lys Leu Thr Val Asp Lys Ser
385                 390                 395                 400
Arg Trp Gln Gln Gly Asn Val Phe Ser Cys Ser Val Met His Glu Ala
                405                 410                 415
Leu His Asn His Tyr Thr Gln Lys Ser Leu Ser Leu Ser Pro Gly Lys
            420                 425                 430

<210> SEQ ID NO 4
<211> LENGTH: 214
<212> TYPE: PRT
<213> ORGANISM: artificial
<220> FEATURE:
<223> OTHER INFORMATION: Protein Sequence for Light Chain, Ranibizumab
      (VEGF Fab)

<400> SEQUENCE: 4

Asp Ile Gln Leu Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 5
<211> LENGTH: 231
<212> TYPE: PRT
<213> ORGANISM: artificial
<220> FEATURE:
<223> OTHER INFORMATION: Heavy Chain Ranibizumab (VEGF Fab)

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 6
<211> LENGTH: 251
<212> TYPE: PRT
```

```
<213> ORGANISM: artificial
<220> FEATURE:
<223> OTHER INFORMATION: VEGF ScFv

<400> SEQUENCE: 6

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Ser Gly Gly Gly Ser Gly Gly
        115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250

<210> SEQ ID NO 7
<211> LENGTH: 453
<212> TYPE: PRT
<213> ORGANISM: artificial
<220> FEATURE:
<223> OTHER INFORMATION: heavy chain of a VEGF antibody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
             85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 8
<211> LENGTH: 25
<212> TYPE: PRT
<213> ORGANISM: artificial
<220> FEATURE:
<223> OTHER INFORMATION: L1-7
```

<400> SEQUENCE: 8

Ala Gln Gln Thr Asn Phe Met Pro Met Asp Asp Leu Glu Gln Arg Leu
1               5                   10                  15

Tyr Glu Gln Phe Ile Leu Gln Gln Gly
            20                  25

<210> SEQ ID NO 9
<211> LENGTH: 24
<212> TYPE: PRT
<213> ORGANISM: artificial
<220> FEATURE:
<223> OTHER INFORMATION: L1-10

<400> SEQUENCE: 9

Ala Gln Gln Lys Phe Gln Pro Leu Asp Glu Leu Glu Gln Thr Leu Tyr
1               5                   10                  15

Glu Gln Phe Met Leu Gln Gln Ala
            20

<210> SEQ ID NO 10
<211> LENGTH: 24
<212> TYPE: PRT
<213> ORGANISM: artificial
<220> FEATURE:
<223> OTHER INFORMATION: L1-15

<400> SEQUENCE: 10

Ala Gln Gln Lys Tyr Gln Pro Leu Asp Glu Leu Asp Lys Thr Leu Tyr
1               5                   10                  15

Asp Gln Phe Met Leu Gln Gln Gly
            20

<210> SEQ ID NO 11
<211> LENGTH: 23
<212> TYPE: PRT
<213> ORGANISM: artificial
<220> FEATURE:
<223> OTHER INFORMATION: L1-7B

<400> SEQUENCE: 11

Gln Thr Asn Phe Met Pro Met Asp Asp Leu Glu Gln Arg Leu Tyr Glu
1               5                   10                  15

Gln Phe Ile Leu Gln Gln Gly
            20

<210> SEQ ID NO 12
<211> LENGTH: 22
<212> TYPE: PRT
<213> ORGANISM: artificial
<220> FEATURE:
<223> OTHER INFORMATION: L1-10B

<400> SEQUENCE: 12

Gln Lys Phe Gln Pro Leu Asp Glu Leu Glu Gln Thr Leu Tyr Glu Gln
1               5                   10                  15

Phe Met Leu Gln Gln Ala
            20

<210> SEQ ID NO 13
<211> LENGTH: 22
<212> TYPE: PRT
<213> ORGANISM: artificial
<220> FEATURE:

```
<223> OTHER INFORMATION: L1-15B

<400> SEQUENCE: 13

Gln Lys Tyr Gln Pro Leu Asp Glu Leu Asp Lys Thr Leu Tyr Asp Gln
1               5                   10                  15

Phe Met Leu Gln Gln Gly
            20

<210> SEQ ID NO 14
<211> LENGTH: 22
<212> TYPE: PRT
<213> ORGANISM: artificial
<220> FEATURE:
<223> OTHER INFORMATION: CVX-060

<400> SEQUENCE: 14

Gln Lys Tyr Gln Pro Leu Asp Glu Lys Asp Lys Thr Leu Tyr Asp Gln
1               5                   10                  15

Phe Met Leu Gln Gln Gly
            20

<210> SEQ ID NO 15
<211> LENGTH: 471
<212> TYPE: PRT
<213> ORGANISM: artificial
<220> FEATURE:
<223> OTHER INFORMATION: L1-15 fused to the N-terminus of the VEGF Trap,
      with linker peptide GGGGSGGGGSGGGGS

<400> SEQUENCE: 15

Ala Gln Gln Lys Tyr Gln Pro Leu Asp Glu Leu Asp Lys Thr Leu Tyr
1               5                   10                  15

Asp Gln Phe Met Leu Gln Gln Gly Gly Gly Gly Gly Ser Gly Gly Gly
            20                  25                  30

Gly Ser Gly Gly Gly Gly Ser Ser Asp Thr Gly Arg Pro Phe Val Glu
        35                  40                  45

Met Tyr Ser Glu Ile Pro Glu Ile Ile His Met Thr Glu Gly Arg Glu
    50                  55                  60

Leu Val Ile Pro Cys Arg Val Thr Ser Pro Asn Ile Thr Val Thr Leu
65                  70                  75                  80

Lys Lys Phe Pro Leu Asp Thr Leu Ile Pro Asp Gly Lys Arg Ile Ile
                85                  90                  95

Trp Asp Ser Arg Lys Gly Phe Ile Ile Ser Asn Ala Thr Tyr Lys Glu
            100                 105                 110

Ile Gly Leu Leu Thr Cys Glu Ala Thr Val Asn Gly His Leu Tyr Lys
        115                 120                 125

Thr Asn Tyr Leu Thr His Arg Gln Thr Asn Thr Ile Ile Asp Val Val
    130                 135                 140

Leu Ser Pro Ser His Gly Ile Glu Leu Ser Val Gly Glu Lys Leu Val
145                 150                 155                 160

Leu Asn Cys Thr Ala Arg Thr Glu Leu Asn Val Gly Ile Asp Phe Asn
                165                 170                 175

Trp Glu Tyr Pro Ser Ser Lys His Gln His Lys Lys Leu Val Asn Arg
            180                 185                 190

Asp Leu Lys Thr Gln Ser Gly Ser Glu Met Lys Lys Phe Leu Ser Thr
        195                 200                 205

Leu Thr Ile Asp Gly Val Thr Arg Ser Asp Gln Gly Leu Tyr Thr Cys
    210                 215                 220
```

-continued

```
Ala Ala Ser Ser Gly Leu Met Thr Lys Lys Asn Ser Thr Phe Val Arg
225                 230                 235                 240

Val His Glu Lys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 16
<211> LENGTH: 464
<212> TYPE: PRT
<213> ORGANISM: artificial
<220> FEATURE:
<223> OTHER INFORMATION: AMD-I (L1-15 fused to VEGF Trap)
<220> FEATURE:
<221> NAME/KEY: VARIANT
<222> LOCATION: (1)..(1)
<223> OTHER INFORMATION: X is A, G, or deleted
<220> FEATURE:
<221> NAME/KEY: VARIANT
<222> LOCATION: (2)..(2)
<223> OTHER INFORMATION: X is Q or A or deleted
<220> FEATURE:
<221> NAME/KEY: VARIANT
<222> LOCATION: (5)..(5)
<223> OTHER INFORMATION: X is Y or F
<220> FEATURE:
<221> NAME/KEY: VARIANT
<222> LOCATION: (12)..(12)
<223> OTHER INFORMATION: X is D or E
<220> FEATURE:
<221> NAME/KEY: VARIANT
<222> LOCATION: (13)..(13)
<223> OTHER INFORMATION: X is Q or K
<220> FEATURE:
<221> NAME/KEY: VARIANT
<222> LOCATION: (17)..(17)
<223> OTHER INFORMATION: X is D or E
```

```
<220> FEATURE:
<221> NAME/KEY: VARIANT
<222> LOCATION: (25)..(25)
<223> OTHER INFORMATION: X is L or deleted
<220> FEATURE:
<221> NAME/KEY: VARIANT
<222> LOCATION: (26)..(26)
<223> OTHER INFORMATION: X is E is deleted
<220> FEATURE:
<221> NAME/KEY: VARIANT
<222> LOCATION: (27)..(31)
<223> OTHER INFORMATION: Sequence can be deleted or repeated such that
      (GGGGS)n wherein n = 0, 1, 2, 3, 4, or 5
<220> FEATURE:
<221> NAME/KEY: VARIANT
<222> LOCATION: (464)..(464)
<223> OTHER INFORMATION: C-terminal amino acid K may be deleted

<400> SEQUENCE: 16

Xaa Xaa Gln Lys Xaa Gln Pro Leu Asp Glu Leu Xaa Xaa Thr Leu Tyr
1               5                   10                  15

Xaa Gln Phe Met Leu Gln Gln Gly Xaa Xaa Gly Gly Gly Gly Ser Asn
            20                  25                  30

Ser Asp Thr Gly Arg Pro Phe Val Glu Met Tyr Ser Glu Ile Pro Glu
        35                  40                  45

Ile Ile His Met Thr Glu Gly Arg Glu Leu Val Ile Pro Cys Arg Val
    50                  55                  60

Thr Ser Pro Asn Ile Thr Val Thr Leu Lys Lys Phe Pro Leu Asp Thr
65                  70                  75                  80

Leu Ile Pro Asp Gly Lys Arg Ile Ile Trp Asp Ser Arg Lys Gly Phe
                85                  90                  95

Ile Ile Ser Asn Ala Thr Tyr Lys Glu Ile Gly Leu Leu Thr Cys Glu
            100                 105                 110

Ala Thr Val Asn Gly His Leu Tyr Lys Thr Asn Tyr Leu Thr His Arg
        115                 120                 125

Gln Thr Asn Thr Ile Ile Asp Val Val Leu Ser Pro Ser His Gly Ile
    130                 135                 140

Glu Leu Ser Val Gly Glu Lys Leu Val Leu Asn Cys Thr Ala Arg Thr
145                 150                 155                 160

Glu Leu Asn Val Gly Ile Asp Phe Asn Trp Glu Tyr Pro Ser Ser Lys
                165                 170                 175

His Gln His Lys Lys Leu Val Asn Arg Asp Leu Lys Thr Gln Ser Gly
            180                 185                 190

Ser Glu Met Lys Lys Phe Leu Ser Thr Leu Thr Ile Asp Gly Val Thr
        195                 200                 205

Arg Ser Asp Gln Gly Leu Tyr Thr Cys Ala Ala Ser Ser Gly Leu Met
    210                 215                 220

Thr Lys Lys Asn Ser Thr Phe Val Arg Val His Glu Lys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320
```

-continued

```
Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
        340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460
```

```
<210> SEQ ID NO 17
<211> LENGTH: 464
<212> TYPE: PRT
<213> ORGANISM: artificial
<220> FEATURE:
<223> OTHER INFORMATION: AMD-J (L1-7 fused to VEGF Trap)
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
<220> FEATURE:
<221> NAME/KEY: variant
<222> LOCATION: (26)..(26)
<223> OTHER INFORMATION: X is L or deleted
<220> FEATURE:
<221> NAME/KEY: variant
<222> LOCATION: (27)..(27)
<223> OTHER INFORMATION: X is E is deleted
<220> FEATURE:
<221> NAME/KEY: variant
<222> LOCATION: (28)..(32)
<223> OTHER INFORMATION: (GGGGS)n can be repeated such that n = 0, 1, 2,
    3, 4, or 5
<220> FEATURE:
<221> NAME/KEY: variant
<222> LOCATION: (464)..(464)
<223> OTHER INFORMATION: C-terminal amino acid K may be deleted

<400> SEQUENCE: 17

Xaa Xaa Gln Thr Asn Phe Met Pro Met Asp Asp Leu Glu Gln Arg Leu
1               5                   10                  15

Tyr Glu Gln Phe Ile Leu Gln Gln Gly Xaa Xaa Gly Gly Gly Gly Ser
            20                  25                  30

Ser Asp Thr Gly Arg Pro Phe Val Glu Met Tyr Ser Glu Ile Pro Glu
        35                  40                  45

Ile Ile His Met Thr Glu Gly Arg Glu Leu Val Ile Pro Cys Arg Val
    50                  55                  60

Thr Ser Pro Asn Ile Thr Val Thr Leu Lys Lys Phe Pro Leu Asp Thr
65                  70                  75                  80

Leu Ile Pro Asp Gly Lys Arg Ile Ile Trp Asp Ser Arg Lys Gly Phe
```

```
                85                  90                  95
Ile Ile Ser Asn Ala Thr Tyr Lys Glu Ile Gly Leu Leu Thr Cys Glu
            100                 105                 110

Ala Thr Val Asn Gly His Leu Tyr Lys Thr Asn Tyr Leu Thr His Arg
            115                 120             125

Gln Thr Asn Thr Ile Ile Asp Val Val Leu Ser Pro Ser His Gly Ile
            130             135                 140

Glu Leu Ser Val Gly Glu Lys Leu Val Leu Asn Cys Thr Ala Arg Thr
145             150                 155                 160

Glu Leu Asn Val Gly Ile Asp Phe Asn Trp Glu Tyr Pro Ser Ser Lys
                165                 170                 175

His Gln His Lys Lys Leu Val Asn Arg Asp Leu Lys Thr Gln Ser Gly
            180                 185                 190

Ser Glu Met Lys Lys Phe Leu Ser Thr Leu Thr Ile Asp Gly Val Thr
            195                 200                 205

Arg Ser Asp Gln Gly Leu Tyr Thr Cys Ala Ala Ser Ser Gly Leu Met
            210                 215                 220

Thr Lys Lys Asn Ser Thr Phe Val Arg Val His Glu Lys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
            370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
            450                 455                 460

<210> SEQ ID NO 18

<400> SEQUENCE: 18

000
```

-continued

```
<210> SEQ ID NO 19
<211> LENGTH: 262
<212> TYPE: PRT
<213> ORGANISM: artificial
<220> FEATURE:
<223> OTHER INFORMATION: AMD-K Heavy Chain (L1-15 fused to VEGF Fab)
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
<220> FEATURE:
<221> NAME/KEY: variant
<222> LOCATION: (5)..(5)
<223> OTHER INFORMATION: X is Y or F
<220> FEATURE:
<221> NAME/KEY: variant
<222> LOCATION: (12)..(12)
<223> OTHER INFORMATION: X is D or E
<220> FEATURE:
<221> NAME/KEY: variant
<222> LOCATION: (13)..(13)
<223> OTHER INFORMATION: X is Q or K
<220> FEATURE:
<221> NAME/KEY: variant
<222> LOCATION: (17)..(17)
<223> OTHER INFORMATION: X is D or E
<220> FEATURE:
<221> NAME/KEY: variant
<222> LOCATION: (25)..(25)
<223> OTHER INFORMATION: X is L or deleted
<220> FEATURE:
<221> NAME/KEY: variant
<222> LOCATION: (26)..(26)
<223> OTHER INFORMATION: X is E is deleted
<220> FEATURE:
<221> NAME/KEY: variant
<222> LOCATION: (27)..(31)
<223> OTHER INFORMATION: Sequence can be deleted or repeated such that
      (GGGGS)n wherein n = 0, 1, 2, 3, 4, or 5

<400> SEQUENCE: 19

Xaa Xaa Gln Lys Xaa Gln Pro Leu Asp Glu Leu Xaa Xaa Thr Leu Tyr
1               5                   10                  15

Xaa Gln Phe Met Leu Gln Gln Gly Xaa Xaa Gly Gly Gly Gly Ser Glu
                20                  25                  30

Val Gln Leu Val Glu Ser Gly Gly Gly Leu Val Gln Pro Gly Gly Ser
            35                  40                  45

Leu Arg Leu Ser Cys Ala Ala Ser Gly Tyr Asp Phe Thr His Tyr Gly
        50                  55                  60

Met Asn Trp Val Arg Gln Ala Pro Gly Lys Gly Leu Glu Trp Val Gly
65                  70                  75                  80

Trp Ile Asn Thr Tyr Thr Gly Glu Pro Thr Tyr Ala Ala Asp Phe Lys
                85                  90                  95

Arg Arg Phe Thr Phe Ser Leu Asp Thr Ser Lys Ser Thr Ala Tyr Leu
            100                 105                 110

Gln Met Asn Ser Leu Arg Ala Glu Asp Thr Ala Val Tyr Tyr Cys Ala
        115                 120                 125

Lys Tyr Pro Tyr Tyr Gly Thr Ser His Trp Tyr Phe Asp Val Trp
    130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175
```

```
Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Leu
            260

<210> SEQ ID NO 20
<211> LENGTH: 263
<212> TYPE: PRT
<213> ORGANISM: artificial
<220> FEATURE:
<223> OTHER INFORMATION: L1-7 fused to VEGF Fab
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
<220> FEATURE:
<221> NAME/KEY: variant
<222> LOCATION: (26)..(26)
<223> OTHER INFORMATION: X is L or deleted
<220> FEATURE:
<221> NAME/KEY: variant
<222> LOCATION: (27)..(27)
<223> OTHER INFORMATION: X is E or deleted
<220> FEATURE:
<221> NAME/KEY: variant
<222> LOCATION: (28)..(32)
<223> OTHER INFORMATION: Sequence can be deleted or repeated such that
      (GGGGS)n wherein n = 0, 1, 2, 3, 4, or 5

<400> SEQUENCE: 20

Xaa Xaa Gln Thr Asn Phe Met Pro Met Asp Asp Leu Glu Gln Arg Leu
1               5                   10                  15

Tyr Glu Gln Phe Ile Leu Gln Gln Gly Xaa Xaa Gly Gly Gly Gly Ser
            20                  25                  30

Glu Val Gln Leu Val Glu Ser Gly Gly Gly Leu Val Gln Pro Gly Gly
        35                  40                  45

Ser Leu Arg Leu Ser Cys Ala Ala Ser Gly Tyr Asp Phe Thr His Tyr
    50                  55                  60

Gly Met Asn Trp Val Arg Gln Ala Pro Gly Lys Gly Leu Glu Trp Val
65                  70                  75                  80

Gly Trp Ile Asn Thr Tyr Thr Gly Glu Pro Thr Tyr Ala Ala Asp Phe
                85                  90                  95

Lys Arg Arg Phe Thr Phe Ser Leu Asp Thr Ser Lys Ser Thr Ala Tyr
            100                 105                 110

Leu Gln Met Asn Ser Leu Arg Ala Glu Asp Thr Ala Val Tyr Tyr Cys
        115                 120                 125

Ala Lys Tyr Pro Tyr Tyr Tyr Gly Thr Ser His Trp Tyr Phe Asp Val
    130                 135                 140

Trp Gly Gln Gly Thr Leu Val Thr Val Ser Ser Ala Ser Thr Lys Gly
145                 150                 155                 160
```

```
Pro Ser Val Phe Pro Leu Ala Pro Ser Ser Lys Ser Thr Ser Gly Gly
            165                 170                 175

Thr Ala Ala Leu Gly Cys Leu Val Lys Asp Tyr Phe Pro Glu Pro Val
        180                 185                 190

Thr Val Ser Trp Asn Ser Gly Ala Leu Thr Ser Gly Val His Thr Phe
    195                 200                 205

Pro Ala Val Leu Gln Ser Ser Gly Leu Tyr Ser Leu Ser Ser Val Val
210                 215                 220

Thr Val Pro Ser Ser Ser Leu Gly Thr Gln Thr Tyr Ile Cys Asn Val
225                 230                 235                 240

Asn His Lys Pro Ser Asn Thr Lys Val Asp Lys Lys Val Glu Pro Lys
                245                 250                 255

Ser Cys Asp Lys Thr His Leu
            260

<210> SEQ ID NO 21
<211> LENGTH: 282
<212> TYPE: PRT
<213> ORGANISM: artificial
<220> FEATURE:
<223> OTHER INFORMATION: L1-15 fused to VEGF ScFv
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
<220> FEATURE:
<221> NAME/KEY: variant
<222> LOCATION: (5)..(5)
<223> OTHER INFORMATION: X is Y or F
<220> FEATURE:
<221> NAME/KEY: variant
<222> LOCATION: (12)..(12)
<223> OTHER INFORMATION: X is D or E
<220> FEATURE:
<221> NAME/KEY: variant
<222> LOCATION: (13)..(13)
<223> OTHER INFORMATION: X is Q or K
<220> FEATURE:
<221> NAME/KEY: variant
<222> LOCATION: (17)..(17)
<223> OTHER INFORMATION: X is D or E
<220> FEATURE:
<221> NAME/KEY: variant
<222> LOCATION: (25)..(25)
<223> OTHER INFORMATION: X is L or deleted
<220> FEATURE:
<221> NAME/KEY: variant
<222> LOCATION: (26)..(26)
<223> OTHER INFORMATION: X is E is deleted
<220> FEATURE:
<221> NAME/KEY: variant
<222> LOCATION: (27)..(31)
<223> OTHER INFORMATION: Sequence can be deleted or repeated such that
      (GGGGS)n wherein n = 0, 1, 2, 3, 4, or 5

<400> SEQUENCE: 21

Xaa Xaa Gln Lys Xaa Gln Pro Leu Asp Glu Leu Xaa Xaa Thr Leu Tyr
1               5                   10                  15

Xaa Gln Phe Met Leu Gln Gln Gly Xaa Xaa Gly Gly Gly Gly Ser Glu
            20                  25                  30

Ile Val Met Thr Gln Ser Pro Ser Thr Leu Ser Ala Ser Val Gly Asp
        35                  40                  45

Arg Val Ile Ile Thr Cys Gln Ala Ser Glu Ile Ile His Ser Trp Leu
    50                  55                  60
```

```
Ala Trp Tyr Gln Gln Lys Pro Gly Lys Ala Pro Lys Leu Leu Ile Tyr
 65                  70                  75                  80

Leu Ala Ser Thr Leu Ala Ser Gly Val Pro Ser Arg Phe Ser Gly Ser
                 85                  90                  95

Gly Ser Gly Ala Glu Phe Thr Leu Thr Ile Ser Ser Leu Gln Pro Asp
            100                 105                 110

Asp Phe Ala Thr Tyr Tyr Cys Gln Asn Val Tyr Leu Ala Ser Thr Asn
            115                 120                 125

Gly Ala Asn Phe Gly Gln Gly Thr Lys Leu Thr Val Leu Gly Gly Gly
        130                 135                 140

Gly Gly Ser Gly Gly Gly Gly Ser Gly Gly Gly Ser Gly Gly Gly Gly
145                 150                 155                 160

Gly Ser Glu Val Gln Leu Val Glu Ser Gly Gly Leu Val Gln Pro Gly
            165                 170                 175

Gly Ser Leu Arg Leu Ser Cys Thr Ala Ser Gly Phe Ser Leu Thr
        180                 185                 190

Asp Tyr Tyr Met Thr Trp Val Arg Gln Ala Pro Gly Lys Gly Leu
        195                 200                 205

Glu Trp Val Gly Phe Ile Asp Pro Asp Asp Pro Tyr Tyr Ala Thr
210                 215                 220

Trp Ala Lys Gly Arg Phe Thr Ile Ser Arg Asp Asn Ser Lys Asn Thr
225                 230                 235                 240

Leu Tyr Leu Gln Met Asn Ser Leu Arg Ala Glu Asp Thr Ala Val Tyr
                245                 250                 255

Tyr Cys Ala Gly Gly Asp His Asn Ser Gly Trp Gly Leu Asp Ile Trp
            260                 265                 270

Gly Gln Gly Thr Leu Val Thr Val Ser Ser
        275                 280

<210> SEQ ID NO 22
<211> LENGTH: 283
<212> TYPE: PRT
<213> ORGANISM: artificial
<220> FEATURE:
<223> OTHER INFORMATION: L1-7 fused to VEGF ScFv
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
<220> FEATURE:
<221> NAME/KEY: variant
<222> LOCATION: (26)..(26)
<223> OTHER INFORMATION: X is L or deleted
<220> FEATURE:
<221> NAME/KEY: variant
<222> LOCATION: (27)..(27)
<223> OTHER INFORMATION: X is E is deleted
<220> FEATURE:
<221> NAME/KEY: variant
<222> LOCATION: (28)..(32)
<223> OTHER INFORMATION: Sequence can be deleted or repeated such that
      (GGGGS)n wherein n = 0, 1, 2, 3, 4, or 5

<400> SEQUENCE: 22

Xaa Xaa Gln Thr Asn Phe Met Pro Met Asp Asp Leu Glu Gln Arg Leu
1                5                  10                  15

Tyr Glu Gln Phe Ile Leu Gln Gln Gly Xaa Xaa Gly Gly Gly Gly Ser
                 20                  25                  30
```

```
Glu Ile Val Met Thr Gln Ser Pro Ser Thr Leu Ser Ala Ser Val Gly
         35                  40                  45

Asp Arg Val Ile Ile Thr Cys Gln Ala Ser Glu Ile Ile His Ser Trp
 50                  55                  60

Leu Ala Trp Tyr Gln Gln Lys Pro Gly Lys Ala Pro Lys Leu Leu Ile
 65                  70                  75                  80

Tyr Leu Ala Ser Thr Leu Ala Ser Gly Val Pro Ser Arg Phe Ser Gly
                 85                  90                  95

Ser Gly Ser Gly Ala Glu Phe Thr Leu Thr Ile Ser Ser Leu Gln Pro
            100                 105                 110

Asp Asp Phe Ala Thr Tyr Tyr Cys Gln Asn Val Tyr Leu Ala Ser Thr
            115                 120                 125

Asn Gly Ala Asn Phe Gly Gln Gly Thr Lys Leu Thr Val Leu Gly Gly
        130                 135                 140

Gly Gly Gly Ser Gly Gly Gly Gly Ser Gly Gly Gly Ser Gly Gly
145                 150                 155                 160

Gly Gly Ser Glu Val Gln Leu Val Glu Ser Gly Gly Gly Leu Val Gln
            165                 170                 175

Pro Gly Gly Ser Leu Arg Leu Ser Cys Thr Ala Ser Gly Phe Ser Leu
        180                 185                 190

Thr Asp Tyr Tyr Met Thr Trp Val Arg Gln Ala Pro Gly Lys Gly
            195                 200                 205

Leu Glu Trp Val Gly Phe Ile Asp Pro Asp Asp Pro Tyr Tyr Ala
210                 215                 220

Thr Trp Ala Lys Gly Arg Phe Thr Ile Ser Arg Asp Asn Ser Lys Asn
225                 230                 235                 240

Thr Leu Tyr Leu Gln Met Asn Ser Leu Arg Ala Glu Asp Thr Ala Val
            245                 250                 255

Tyr Tyr Cys Ala Gly Gly Asp His Asn Ser Gly Trp Gly Leu Asp Ile
        260                 265                 270

Trp Gly Gln Gly Thr Leu Val Thr Val Ser Ser
        275                 280
```

```
<210> SEQ ID NO 23
<211> LENGTH: 463
<212> TYPE: PRT
<213> ORGANISM: artificial
<220> FEATURE:
<223> OTHER INFORMATION: L1-15 fused to C-terminal of VEGF Trap
<220> FEATURE:
<221> NAME/KEY: variant
<222> LOCATION: (433)..(437)
<223> OTHER INFORMATION: (GGGGS)n can be absent or repeated, wherein n =
      0, 1, 2, 3, 4, or 5
<220> FEATURE:
<221> NAME/KEY: variant
<222> LOCATION: (438)..(438)
<223> OTHER INFORMATION: X is A, G, or deleted
<220> FEATURE:
<221> NAME/KEY: variant
<222> LOCATION: (439)..(439)
<223> OTHER INFORMATION: X is Q or A or deleted
<220> FEATURE:
<221> NAME/KEY: variant
<222> LOCATION: (440)..(440)
<223> OTHER INFORMATION: X is Q or A or deleted
<220> FEATURE:
<221> NAME/KEY: variant
<222> LOCATION: (442)..(442)
<223> OTHER INFORMATION: X is Y or F
<220> FEATURE:
<221> NAME/KEY: variant
```

```
<222> LOCATION: (449)..(449)
<223> OTHER INFORMATION: X is D or E
<220> FEATURE:
<221> NAME/KEY: variant
<222> LOCATION: (450)..(450)
<223> OTHER INFORMATION: X is Q or K
<220> FEATURE:
<221> NAME/KEY: variant
<222> LOCATION: (454)..(454)
<223> OTHER INFORMATION: X is D or E
<220> FEATURE:
<221> NAME/KEY: variant
<222> LOCATION: (462)..(462)
<223> OTHER INFORMATION: X is L or deleted
<220> FEATURE:
<221> NAME/KEY: variant
<222> LOCATION: (463)..(463)
<223> OTHER INFORMATION: X is E or deleted

<400> SEQUENCE: 23
```

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
             20                  25                  30

Thr Ser Pro Asn Ile Thr Val Thr Leu Lys Lys Phe Pro Leu Asp Thr
         35                  40                  45

Leu Ile Pro Asp Gly Lys Arg Ile Ile Trp Asp Ser Arg Lys Gly Phe
     50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr

```
                305                 310                 315                 320
Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
                340                 345                 350

Leu Val Lys Gly Phe Tyr Pro Ser Asp Ile Ala Val Glu Trp Glu Ser
                355                 360                 365

Asn Gly Gln Pro Glu Asn Asn Tyr Lys Thr Thr Pro Val Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Ala
                420                 425                 430

Gly Gly Gly Gly Ser Xaa Xaa Gln Lys Xaa Gln Pro Leu Asp Glu Leu
                435                 440                 445

Xaa Xaa Thr Leu Tyr Xaa Gln Phe Met Leu Gln Gln Gly Xaa Xaa
    450                 455                 460
```

<210> SEQ ID NO 24
<211> LENGTH: 464
<212> TYPE: PRT
<213> ORGANISM: artificial
<220> FEATURE:
<223> OTHER INFORMATION: L1-7 fused to C-terminal of VEGF Trap
<220> FEATURE:
<221> NAME/KEY: variant
<222> LOCATION: (433)..(437)
<223> OTHER INFORMATION: Sequence can be deleted or repeated such that
      (GGGGS)n wherein n = 0, 1, 2, 3, 4, or 5
<220> FEATURE:
<221> NAME/KEY: variant
<222> LOCATION: (438)..(438)
<223> OTHER INFORMATION: X is A, G, or deleted
<220> FEATURE:
<221> NAME/KEY: variant
<222> LOCATION: (439)..(439)
<223> OTHER INFORMATION: X is Q, A or deleted
<220> FEATURE:
<221> NAME/KEY: variant
<222> LOCATION: (463)..(463)
<223> OTHER INFORMATION: X is L or deleted
<220> FEATURE:
<221> NAME/KEY: variant
<222> LOCATION: (464)..(464)
<223> OTHER INFORMATION: X is E or deleted

<400> SEQUENCE: 24

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
                35                  40                  45

Leu Ile Pro Asp Gly Lys Arg Ile Ile Trp Asp Ser Arg Lys Gly Phe
            50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
```

```
                100                 105                 110
Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Ala
            420                 425                 430

Gly Gly Gly Gly Ser Xaa Xaa Gln Thr Asn Phe Met Pro Met Asp Asp
        435                 440                 445

Leu Glu Gln Arg Leu Tyr Glu Gln Phe Ile Leu Gln Gln Gly Xaa Xaa
        450                 455                 460

<210> SEQ ID NO 25
<211> LENGTH: 262
<212> TYPE: PRT
<213> ORGANISM: artificial
<220> FEATURE:
<223> OTHER INFORMATION: L1-15 fused to C-terminal VEGF Fab
<220> FEATURE:
<221> NAME/KEY: variant
<222> LOCATION: (237)..(237)
<223> OTHER INFORMATION: X is A, G, or deleted
```

```
<220> FEATURE:
<221> NAME/KEY: variant
<222> LOCATION: (238)..(238)
<223> OTHER INFORMATION: X is Q or A or deleted
<220> FEATURE:
<221> NAME/KEY: variant
<222> LOCATION: (241)..(241)
<223> OTHER INFORMATION: X is Y or F
<220> FEATURE:
<221> NAME/KEY: variant
<222> LOCATION: (248)..(248)
<223> OTHER INFORMATION: X is D or E
<220> FEATURE:
<221> NAME/KEY: variant
<222> LOCATION: (249)..(249)
<223> OTHER INFORMATION: X is Q or K
<220> FEATURE:
<221> NAME/KEY: variant
<222> LOCATION: (253)..(253)
<223> OTHER INFORMATION: X is D or E
<220> FEATURE:
<221> NAME/KEY: variant
<222> LOCATION: (261)..(261)
<223> OTHER INFORMATION: X is L or deleted
<220> FEATURE:
<221> NAME/KEY: variant
<222> LOCATION: (262)..(262)
<223> OTHER INFORMATION: X is E is deleted

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu Gly Gly Gly Gly Ser Xaa Xaa Gln Lys
225                 230                 235                 240

Xaa Gln Pro Leu Asp Glu Leu Xaa Xaa Thr Leu Tyr Xaa Gln Phe Met
                245                 250                 255
```

Leu Gln Gln Gly Xaa Xaa
            260

<210> SEQ ID NO 26
<211> LENGTH: 263
<212> TYPE: PRT
<213> ORGANISM: artificial
<220> FEATURE:
<223> OTHER INFORMATION: L1-7 fused to VEGF Fab
<220> FEATURE:
<221> NAME/KEY: variant
<222> LOCATION: (232)..(236)
<223> OTHER INFORMATION: Sequence can be deleted or repeated such that
      (GGGGS)n wherein n = 0, 1, 2, 3, 4, or 5
<220> FEATURE:
<221> NAME/KEY: variant
<222> LOCATION: (237)..(237)
<223> OTHER INFORMATION: X is A, G, or deleted
<220> FEATURE:
<221> NAME/KEY: variant
<222> LOCATION: (238)..(238)
<223> OTHER INFORMATION: X is Q or A or deleted
<220> FEATURE:
<221> NAME/KEY: variant
<222> LOCATION: (262)..(262)
<223> OTHER INFORMATION: X is L or deleted
<220> FEATURE:
<221> NAME/KEY: variant
<222> LOCATION: (263)..(263)
<223> OTHER INFORMATION: X is E is deleted

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu Gly Gly Gly Gly Ser Xaa Xaa Gln Thr
225                 230                 235                 240

```
Asn Phe Met Pro Met Asp Asp Leu Glu Gln Arg Leu Tyr Glu Gln Phe
                245                 250                 255

Ile Leu Gln Gln Gly Xaa Xaa
            260
```

<210> SEQ ID NO 27
<211> LENGTH: 282
<212> TYPE: PRT
<213> ORGANISM: artificial
<220> FEATURE:
<223> OTHER INFORMATION: L1-15 fused to C-terminal VEGF ScFv
<220> FEATURE:
<221> NAME/KEY: variant
<222> LOCATION: (252)..(256)
<223> OTHER INFORMATION: Sequence can be deleted or repeated such that
      (GGGGS)n wherein n = 0, 1, 2, 3, 4, or 5
<220> FEATURE:
<221> NAME/KEY: variant
<222> LOCATION: (257)..(257)
<223> OTHER INFORMATION: X is A, G, or deleted
<220> FEATURE:
<221> NAME/KEY: variant
<222> LOCATION: (258)..(258)
<223> OTHER INFORMATION: X is Q or A or deleted
<220> FEATURE:
<221> NAME/KEY: variant
<222> LOCATION: (261)..(261)
<223> OTHER INFORMATION: X is Y or F
<220> FEATURE:
<221> NAME/KEY: variant
<222> LOCATION: (268)..(268)
<223> OTHER INFORMATION: X is D or E
<220> FEATURE:
<221> NAME/KEY: variant
<222> LOCATION: (269)..(269)
<223> OTHER INFORMATION: X is Q or K
<220> FEATURE:
<221> NAME/KEY: variant
<222> LOCATION: (273)..(273)
<223> OTHER INFORMATION: X is D or E
<220> FEATURE:
<221> NAME/KEY: variant
<222> LOCATION: (281)..(281)
<223> OTHER INFORMATION: X is L or deleted
<220> FEATURE:
<221> NAME/KEY: variant
<222> LOCATION: (282)..(282)
<223> OTHER INFORMATION: X is E is deleted

<400> SEQUENCE: 27

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140
```

```
Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
            165                 170                 175

Leu Glu Trp Val Gly Phe Ile Asp Pro Asp Asp Pro Tyr Tyr Ala
        180                 185                 190

Thr Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
        210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser Gly Gly Gly Gly Ser
                245                 250                 255

Xaa Xaa Gln Lys Xaa Gln Pro Leu Asp Glu Leu Xaa Xaa Thr Leu Tyr
            260                 265                 270

Xaa Gln Phe Met Leu Gln Gln Gly Xaa Xaa
            275                 280

<210> SEQ ID NO 28
<211> LENGTH: 283
<212> TYPE: PRT
<213> ORGANISM: artificial
<220> FEATURE:
<223> OTHER INFORMATION: AMD-Q-C terminal (L1-7 fused to VEGF ScFv)
<220> FEATURE:
<221> NAME/KEY: variant
<222> LOCATION: (252)..(256)
<223> OTHER INFORMATION: Sequence can be deleted or repeated such that
      (GGGGS)n wherein n = 0, 1, 2, 3, 4, or 5
<220> FEATURE:
<221> NAME/KEY: misc_feature
<222> LOCATION: (257)..(258)
<223> OTHER INFORMATION: X can be any naturally occurring amino acid
<220> FEATURE:
<221> NAME/KEY: variant
<222> LOCATION: (266)..(266)
<223> OTHER INFORMATION: X is A, G, or deleted
<220> FEATURE:
<221> NAME/KEY: variant
<222> LOCATION: (267)..(267)
<223> OTHER INFORMATION: X is Q or A or deleted
<220> FEATURE:
<221> NAME/KEY: variant
<222> LOCATION: (282)..(282)
<223> OTHER INFORMATION: X is L or deleted
<220> FEATURE:
<221> NAME/KEY: variant
<222> LOCATION: (283)..(283)
<223> OTHER INFORMATION: X is E is deleted

<400> SEQUENCE: 28

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65              70                  75                  80

Asp Asp Phe Ala Thr Tyr Tyr Cys Gln Asn Val Tyr Leu Ala Ser Thr
```

```
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Asp Pro Tyr Tyr Ala
            180                 185                 190

Thr Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser Gly Gly Gly Gly Ser
                245                 250                 255

Xaa Xaa Gln Thr Asn Phe Met Pro Met Asp Asp Leu Glu Gln Arg Leu
            260                 265                 270

Tyr Glu Gln Phe Ile Leu Gln Gln Gly Xaa Xaa
        275                 280

<210> SEQ ID NO 29
<211> LENGTH: 494
<212> TYPE: PRT
<213> ORGANISM: artificial
<220> FEATURE:
<223> OTHER INFORMATION: ASKB712-O (L1-15 fused to the N-terminal of an
      VEGF-binding antibody)

<400> SEQUENCE: 29

Ala Gln Gln Lys Tyr Gln Pro Leu Asp Glu Leu Asp Lys Thr Leu Tyr
1               5                   10                  15

Asp Gln Phe Met Leu Gln Gln Gly Leu Glu Gly Gly Gly Gly Ser Gly
            20                  25                  30

Gly Gly Gly Ser Gly Gly Gly Gly Ser Glu Val Gln Leu Val Glu Ser
        35                  40                  45

Gly Gly Gly Leu Val Gln Pro Gly Gly Ser Leu Arg Leu Ser Cys Ala
    50                  55                  60

Ala Ser Gly Tyr Asp Phe Thr His Tyr Gly Met Asn Trp Val Arg Gln
65                  70                  75                  80

Ala Pro Gly Lys Gly Leu Glu Trp Val Gly Trp Ile Asn Thr Tyr Thr
                85                  90                  95

Gly Glu Pro Thr Tyr Ala Ala Asp Phe Lys Arg Arg Phe Thr Phe Ser
            100                 105                 110

Leu Asp Thr Ser Lys Ser Thr Ala Tyr Leu Gln Met Asn Ser Leu Arg
        115                 120                 125

Ala Glu Asp Thr Ala Val Tyr Tyr Cys Ala Lys Tyr Pro Tyr Tyr Tyr
    130                 135                 140

Gly Thr Ser His Trp Tyr Phe Asp Val Trp Gly Gln Gly Thr Leu Val
145                 150                 155                 160
```

```
Thr Val Ser Ser Ala Ser Thr Lys Gly Pro Ser Val Phe Pro Leu Ala
            165                 170                 175
Pro Ser Ser Lys Ser Thr Ser Gly Gly Thr Ala Ala Leu Gly Cys Leu
        180                 185                 190
Val Lys Asp Tyr Phe Pro Glu Pro Val Thr Val Ser Trp Asn Ser Gly
    195                 200                 205
Ala Leu Thr Ser Gly Val His Thr Phe Pro Ala Val Leu Gln Ser Ser
210                 215                 220
Gly Leu Tyr Ser Leu Ser Ser Val Val Thr Val Pro Ser Ser Ser Leu
225                 230                 235                 240
Gly Thr Gln Thr Tyr Ile Cys Asn Val Asn His Lys Pro Ser Asn Thr
                245                 250                 255
Lys Val Asp Lys Lys Val Glu Pro Lys Ser Cys Asp Lys Thr His Thr
            260                 265                 270
Cys Pro Pro Cys Pro Ala Pro Glu Ala Ala Gly Gly Pro Ser Val Phe
        275                 280                 285
Leu Phe Pro Pro Lys Pro Lys Asp Thr Leu Met Ile Ser Arg Thr Pro
    290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
        355                 360                 365
Lys Val Ser Asn Lys Ala Leu Pro Ala Pro Ile Glu Lys Thr Ile Ser
    370                 375                 380
Lys Ala Lys Gly Gln Pro Arg Glu Pro Gln Val Tyr Thr Leu Pro Pro
385                 390                 395                 400
Ser Arg Glu Glu Met Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
            420                 425                 430
Gln Pro Glu Asn Asn Tyr Lys Thr Thr Pro Pro Val Leu Asp Ser Asp
        435                 440                 445
Gly Ser Phe Phe Leu Tyr Ser Lys Leu Thr Val Asp Lys Ser Arg Trp
    450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys
                485                 490

<210> SEQ ID NO 30
<211> LENGTH: 484
<212> TYPE: PRT
<213> ORGANISM: artificial
<220> FEATURE:
<223> OTHER INFORMATION: ASKB712-O3 (L1-15 fused to the N-terminal of an
      VEGF-binding antibody)
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
```

-continued

```
<220> FEATURE:
<221> NAME/KEY: variant
<222> LOCATION: (5)..(5)
<223> OTHER INFORMATION: X is Y or F
<220> FEATURE:
<221> NAME/KEY: variant
<222> LOCATION: (12)..(12)
<223> OTHER INFORMATION: X is D or E
<220> FEATURE:
<221> NAME/KEY: variant
<222> LOCATION: (13)..(13)
<223> OTHER INFORMATION: X is Q or K
<220> FEATURE:
<221> NAME/KEY: variant
<222> LOCATION: (17)..(17)
<223> OTHER INFORMATION: X is D or E
<220> FEATURE:
<221> NAME/KEY: variant
<222> LOCATION: (25)..(25)
<223> OTHER INFORMATION: X is L or deleted
<220> FEATURE:
<221> NAME/KEY: variant
<222> LOCATION: (26)..(26)
<223> OTHER INFORMATION: X is E is deleted
<220> FEATURE:
<221> NAME/KEY: variant
<222> LOCATION: (27)..(31)
<223> OTHER INFORMATION: Sequence can be deleted or repeated such that
      (GGGGS)n wherein n = 0, 1, 2, 3, 4, or 5

<400> SEQUENCE: 30

Xaa Xaa Gln Lys Xaa Gln Pro Leu Asp Glu Leu Xaa Xaa Thr Leu Tyr
1               5                   10                  15

Xaa Gln Phe Met Leu Gln Gln Gly Xaa Xaa Gly Gly Gly Gly Ser Glu
            20                  25                  30

Val Gln Leu Val Glu Ser Gly Gly Gly Leu Val Gln Pro Gly Gly Ser
        35                  40                  45

Leu Arg Leu Ser Cys Ala Ala Ser Gly Tyr Asp Phe Thr His Tyr Gly
    50                  55                  60

Met Asn Trp Val Arg Gln Ala Pro Gly Lys Gly Leu Glu Trp Val Gly
65              70                  75                  80

Trp Ile Asn Thr Tyr Thr Gly Glu Pro Thr Tyr Ala Ala Asp Phe Lys
                85                  90                  95

Arg Arg Phe Thr Phe Ser Leu Asp Thr Ser Lys Ser Thr Ala Tyr Leu
            100                 105                 110

Gln Met Asn Ser Leu Arg Ala Glu Asp Thr Ala Val Tyr Tyr Cys Ala
        115                 120                 125

Lys Tyr Pro Tyr Tyr Gly Thr Ser His Trp Tyr Phe Asp Val Trp
    130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255
```

```
Cys Asp Lys Thr His Thr Cys Pro Pro Cys Pro Ala Pro Glu Ala Ala
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
450                 455                 460

Met His Glu Ala Leu His Asn His Tyr Thr Gln Lys Ser Leu Ser Leu
465                 470                 475                 480

Ser Pro Gly Lys

<210> SEQ ID NO 31
<211> LENGTH: 494
<212> TYPE: PRT
<213> ORGANISM: artificial
<220> FEATURE:
<223> OTHER INFORMATION: ASKB712-O2 (L1-15 fused to the C-terminal of an
      VEGF-binding antibody)

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125
```

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Ala Gly Gly Gly Ser Gly Gly Gly Ser Gly
450                 455                 460

Gly Gly Ser Ala Gln Gln Lys Tyr Gln Pro Leu Asp Glu Leu Asp
465                 470                 475                 480

Lys Thr Leu Tyr Asp Gln Phe Met Leu Gln Gln Gly Leu Glu
                485                 490

<210> SEQ ID NO 32
<211> LENGTH: 484
<212> TYPE: PRT
<213> ORGANISM: artificial
<220> FEATURE:
<223> OTHER INFORMATION: ASKB712-O4 (L1-15 fused to the C-terminal of an
      VEGF-binding antibody)
<220> FEATURE:

```
<221> NAME/KEY: variant
<222> LOCATION: (454)..(458)
<223> OTHER INFORMATION: Sequence can be deleted or repeated such that
      (GGGGS)n wherein n = 0, 1, 2, 3, 4, or 5
<220> FEATURE:
<221> NAME/KEY: variant
<222> LOCATION: (459)..(459)
<223> OTHER INFORMATION: X is A, G, or deleted
<220> FEATURE:
<221> NAME/KEY: variant
<222> LOCATION: (460)..(460)
<223> OTHER INFORMATION: X is Q or A or deleted
<220> FEATURE:
<221> NAME/KEY: variant
<222> LOCATION: (463)..(463)
<223> OTHER INFORMATION: X is Y or F
<220> FEATURE:
<221> NAME/KEY: variant
<222> LOCATION: (470)..(470)
<223> OTHER INFORMATION: X is D or E
<220> FEATURE:
<221> NAME/KEY: variant
<222> LOCATION: (471)..(471)
<223> OTHER INFORMATION: X is Q or K
<220> FEATURE:
<221> NAME/KEY: variant
<222> LOCATION: (475)..(475)
<223> OTHER INFORMATION: X is D or E
<220> FEATURE:
<221> NAME/KEY: variant
<222> LOCATION: (483)..(483)
<223> OTHER INFORMATION: X is L or deleted
<220> FEATURE:
<221> NAME/KEY: variant
<222> LOCATION: (484)..(484)
<223> OTHER INFORMATION: X is E is deleted

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
```

```
                210                 215                 220
Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Ala Gly Gly Gly Ser Xaa Xaa Gln Lys Xaa Gln
    450                 455                 460

Pro Leu Asp Glu Leu Xaa Xaa Thr Leu Tyr Xaa Gln Phe Met Leu Gln
465                 470                 475                 480

Gln Gly Xaa Xaa

<210> SEQ ID NO 33
<211> LENGTH: 485
<212> TYPE: PRT
<213> ORGANISM: artificial
<220> FEATURE:
<223> OTHER INFORMATION: ASKB712-P (L1-7 fused to the N-terminal of an
      VEGF-binding antibody)
<220> FEATURE:
<221> NAME/KEY: variant
<222> LOCATION: (1)..(1)
<223> OTHER INFORMATION: X is A, G, or deleted
<220> FEATURE:
<221> NAME/KEY: variant
<222> LOCATION: (2)..(2)
<223> OTHER INFORMATION: X is Q or A or deleted
<220> FEATURE:
<221> NAME/KEY: variant
<222> LOCATION: (26)..(26)
<223> OTHER INFORMATION: X is L or deleted
<220> FEATURE:
<221> NAME/KEY: variant
<222> LOCATION: (27)..(27)
<223> OTHER INFORMATION: X is E is deleted
<220> FEATURE:
<221> NAME/KEY: variant
<222> LOCATION: (28)..(32)
```

<223> OTHER INFORMATION: Sequence can be deleted or repeated such that
      (GGGGS)n wherein n = 0, 1, 2, 3, 4, or 5

<400> SEQUENCE: 33

```
Xaa Xaa Gln Thr Asn Phe Met Pro Met Asp Asp Leu Glu Gln Arg Leu
1               5                   10                  15

Tyr Glu Gln Phe Ile Leu Gln Gln Xaa Xaa Gly Gly Gly Gly Gly Ser
                20                  25                  30

Glu Val Gln Leu Val Glu Ser Gly Gly Gly Leu Val Gln Pro Gly Gly
            35                  40                  45

Ser Leu Arg Leu Ser Cys Ala Ala Ser Gly Tyr Asp Phe Thr His Tyr
    50                  55                  60

Gly Met Asn Trp Val Arg Gln Ala Pro Gly Lys Gly Leu Glu Trp Val
65                  70                  75                  80

Gly Trp Ile Asn Thr Tyr Thr Gly Glu Pro Thr Tyr Ala Ala Asp Phe
                85                  90                  95

Lys Arg Arg Phe Thr Phe Ser Leu Asp Thr Ser Lys Ser Thr Ala Tyr
                100                 105                 110

Leu Gln Met Asn Ser Leu Arg Ala Glu Asp Thr Ala Val Tyr Tyr Cys
            115                 120                 125

Ala Lys Tyr Pro Tyr Tyr Tyr Gly Thr Ser His Trp Tyr Phe Asp Val
130                 135                 140

Trp Gly Gln Gly Thr Leu Val Thr Val Ser Ser Ala Ser Thr Lys Gly
145                 150                 155                 160

Pro Ser Val Phe Pro Leu Ala Pro Ser Ser Lys Ser Thr Ser Gly Gly
                165                 170                 175

Thr Ala Ala Leu Gly Cys Leu Val Lys Asp Tyr Phe Pro Glu Pro Val
            180                 185                 190

Thr Val Ser Trp Asn Ser Gly Ala Leu Thr Ser Gly Val His Thr Phe
        195                 200                 205

Pro Ala Val Leu Gln Ser Ser Gly Leu Tyr Ser Leu Ser Ser Val Val
    210                 215                 220

Thr Val Pro Ser Ser Ser Leu Gly Thr Gln Thr Tyr Ile Cys Asn Val
225                 230                 235                 240

Asn His Lys Pro Ser Asn Thr Lys Val Asp Lys Lys Val Glu Pro Lys
                245                 250                 255

Ser Cys Asp Lys Thr His Thr Cys Pro Pro Cys Pro Ala Pro Glu Ala
            260                 265                 270

Ala Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Glu Glu Met Thr Lys Asn Gln
385                 390                 395                 400
```

```
Val Ser Leu Thr Cys Leu Val Lys Gly Phe Tyr Pro Ser Asp Ile Ala
            405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
            435                 440                 445

Thr Val Asp Lys Ser Arg Trp Gln Gln Gly Asn Val Phe Ser Cys Ser
            450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 34
<211> LENGTH: 485
<212> TYPE: PRT
<213> ORGANISM: artificial
<220> FEATURE:
<223> OTHER INFORMATION: L1-7 fused to the C-terminal of an VEGF-binding
      antibody
<220> FEATURE:
<221> NAME/KEY: variant
<222> LOCATION: (454)..(458)
<223> OTHER INFORMATION: Sequence can be deleted or repeated such that
      (GGGGS)n wherein n = 0, 1, 2, 3, 4, or 5
<220> FEATURE:
<221> NAME/KEY: variant
<222> LOCATION: (459)..(459)
<223> OTHER INFORMATION: X is A, G, or deleted
<220> FEATURE:
<221> NAME/KEY: variant
<222> LOCATION: (460)..(460)
<223> OTHER INFORMATION: X is Q or A or deleted
<220> FEATURE:
<221> NAME/KEY: variant
<222> LOCATION: (484)..(484)
<223> OTHER INFORMATION: X is L or deleted
<220> FEATURE:
<221> NAME/KEY: variant
<222> LOCATION: (485)..(485)
<223> OTHER INFORMATION: X is E is deleted

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
```

```
                145                 150                 155                 160
        Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                    180                 185                 190

Thr Val Pro Ser Ser Ser Leu Gly Thr Gln Thr Tyr Ile Cys Asn Val
                    195                 200                 205

Asn His Lys Pro Ser Asn Thr Lys Val Asp Lys Val Glu Pro Lys
                    210                 215                 220

Ser Cys Asp Lys Thr His Thr Cys Pro Pro Cys Pro Ala Pro Glu Ala
        225                 230                 235                 240

Ala Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
                    260                 265                 270

Ser His Glu Asp Pro Glu Val Lys Phe Asn Trp Tyr Val Asp Gly Val
                    275                 280                 285

Glu Val His Asn Ala Lys Thr Lys Pro Arg Glu Glu Gln Tyr Asn Ser
                    290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Ala Leu Pro Ala
                    325                 330                 335

Pro Ile Glu Lys Thr Ile Ser Lys Ala Lys Gly Gln Pro Arg Glu Pro
                    340                 345                 350

Gln Val Tyr Thr Leu Pro Pro Ser Arg Glu Glu Met Thr Lys Asn Gln
                    355                 360                 365

Val Ser Leu Thr Cys Leu Val Lys Gly Phe Tyr Pro Ser Asp Ile Ala
                    370                 375                 380

Val Glu Trp Glu Ser Asn Gly Gln Pro Glu Asn Asn Tyr Lys Thr Thr
        385                 390                 395                 400

Pro Pro Val Leu Asp Ser Asp Gly Ser Phe Phe Leu Tyr Ser Lys Leu
                    405                 410                 415

Thr Val Asp Lys Ser Arg Trp Gln Gln Gly Asn Val Phe Ser Cys Ser
                    420                 425                 430

Val Met His Glu Ala Leu His Asn His Tyr Thr Gln Lys Ser Leu Ser
                    435                 440                 445

Leu Ser Pro Gly Ala Gly Gly Gly Ser Xaa Xaa Gln Thr Asn Phe
                    450                 455                 460

Met Pro Met Asp Asp Leu Glu Gln Arg Leu Tyr Glu Gln Phe Ile Leu
        465                 470                 475                 480

Gln Gln Gly Xaa Xaa
                    485

<210> SEQ ID NO 35
<211> LENGTH: 1542
<212> TYPE: DNA
<213> ORGANISM: artificial
<220> FEATURE:
<223> OTHER INFORMATION: 7120_L7_3xGS_DNA sequence

<400> SEQUENCE: 35
atggaattcg gcctgtcttg gctgttcctg gtggccattc tgaagggcgc tctggccgct      60
cagaccaact tcatgcctat ggacgacctg gaacagcggc tgtacgagca gttcatcctg     120
```

| | |
|---|---:|
| cagcaaggac tggaaggcgg cggaggatct ggcggaggcg gtagcggagg cggtggatct | 180 |
| gaagtgcagc tggttgaaag tggcggcgga ttggttcagc ctggcggatc tctgagactg | 240 |
| tcttgtgccg cctctggcta cgacttcacc cactacggca tgaattgggt ccgacaggct | 300 |
| cccggcaaag gcctggaatg ggtcggatgg atcaacacct ataccggcga gcctacctac | 360 |
| gccgccgatt tcaagcggag attcaccttc tccctggaca cctccaagtc taccgcctac | 420 |
| ctgcagatga actccctgag agccgaggac accgccgtgt actactgcgc taagtacccc | 480 |
| tactactacg gcaccagcca ctggtacttc gacgtgtggg gacagggcac actggtcaca | 540 |
| gtgtcctccg cctctaccaa gggaccctct gtgtttcctc tggctcccte cagcaagtcc | 600 |
| acctctggtg aacagctgc tctgggctgc ctggtcaagg actactttcc tgagcctgtg | 660 |
| accgtgtcct gggcttctgg tgctctgaca tctggcgtgc acacctttcc agctgtgctg | 720 |
| cagtcctccg gcctgtactc tctgtcctct gtcgtgaccg tgccttccag ctctctggga | 780 |
| acccagacct acatctgcaa tgtgaaccac aagcccttcca acaccaaggt cgacaagaag | 840 |
| gtggaaccca gtcctgcga taagacccac acctgtcctc catgtcctgc tccagaagct | 900 |
| gctggcggcc catccgtgtt tctgttccct ccaaagccta aggacaccct gatgatctct | 960 |
| cggacccctg aagtgacctg cgtggtggtg gatgtgtctc acgaggaccc agaagtgaag | 1020 |
| ttcaattggt acgtggacgg cgtggaagtg cacaacgcca agaccaagcc tagagaggaa | 1080 |
| cagtacaact ccacctacag agtggtgtcc gtgctgaccg tgctgcacca ggattggctg | 1140 |
| aacggcaaag agtacaagtg caaggtgtcc aacaaggccc tgcctgctcc tatcgaaaag | 1200 |
| accatctcca aggccaaggg ccagcctagg gaaccccagg tttacacctt gcctccaagc | 1260 |
| cgggaagaga tgaccaagaa ccaggtgtcc ctgacctgcc tcgtgaaggg cttctaccct | 1320 |
| tccgatatcg ccgtggaatg ggagagcaat ggccagcctg agaacaacta caagaccact | 1380 |
| cctcctgtgc tggactccga cggctcattc ttcctgtact ccaagctgac agtggacaag | 1440 |
| tccagatggc agcagggcaa cgtgttctcc tgctccgtga tgcacgaggc cctgcacaat | 1500 |
| cactacacac agaagtccct gtctctgtcc cctggcaagt aa | 1542 |

<210> SEQ ID NO 36
<211> LENGTH: 1527
<212> TYPE: DNA
<213> ORGANISM: artificial
<220> FEATURE:
<223> OTHER INFORMATION: 7120_L7_2xGS_DNA sequence

<400> SEQUENCE: 36

| | |
|---|---:|
| atggaattcg gcctgtcttg gctgttcctg gtggccattc tgaagggcgc tctggccgct | 60 |
| cagaccaact tcatgcctat ggacgacctg aacagcggc tgtacgagca gttcatcctg | 120 |
| cagcaaggac tggaaggcgg cggaggatct ggaggcggtg gatctgaagt gcagctggtt | 180 |
| gaaagtggcg gcggattggt tcagcctggc ggatctctga ctgtcttg tgccgcctct | 240 |
| ggctacgact tcacccacta cggcatgaat tgggtccgac aggctcccgg caaaggcctg | 300 |
| gaatgggtcg gatggatcaa cacctatacc ggcgagccta cctacgccgc cgatttcaag | 360 |
| cggagattca ccttctccct ggacacctcc aagtctaccg cctacctgca gatgaactcc | 420 |
| ctgagagccg aggacaccgc cgtgtactac tgcgctaagt accccactac tacggcacc | 480 |
| agccactggt acttcgacgt gtggggacag gcacactgg tcacagtgtc ctccgcctct | 540 |
| accaagggac cctctgtgtt tcctctggct ccctccagca gtccacctc tggtggaaca | 600 |
| gctgctctgg gctgcctggt caaggactac tttcctgagc ctgtgaccgt gtcctgggct | 660 |

-continued

```
tctggtgctc tgacatctgg cgtgcacacc tttccagctg tgctgcagtc ctccggcctg      720
tactctctgt cctctgtcgt gaccgtgcct tccagctctc tgggaaccca gacctacatc      780
tgcaatgtga accacaagcc ttccaacacc aaggtcgaca agaaggtgga acccaagtcc      840
tgcgataaga cccacacctg tcctccatgt cctgctccag aagctgctgg cggcccatcc      900
gtgtttctgt tccctccaaa gcctaaggac accctgatga tctctcggac ccctgaagtg      960
acctgcgtgg tggtggatgt gtctcacgag gacccagaag tgaagttcaa ttggtacgtg     1020
gacggcgtgg aagtgcacaa cgccaagacc aagcctagag aggaacagta caactccacc     1080
tacagagtgg tgtccgtgct gaccgtgctg caccaggatt ggctgaacgg caaagagtac     1140
aagtgcaagg tgtccaacaa ggccctgcct gctcctatcg aaaagaccat ctccaaggcc     1200
aagggccagc ctagggaacc ccaggtttac accttgcctc caagccggga agagatgacc     1260
aagaaccagg tgtccctgac ctgcctcgtg aagggcttct acccttccga tatcgccgtg     1320
gaatgggaga gcaatggcca gcctgagaac aactacaaga ccactcctcc tgtgctggac     1380
tccgacggct cattcttcct gtactccaag ctgacagtgg acaagtccag atggcagcag     1440
ggcaacgtgt tctcctgctc cgtgatgcac gaggccctgc acaatcacta cacacagaag     1500
tccctgtctc tgtcccctgg caagtaa                                         1527
```

<210> SEQ ID NO 37
<211> LENGTH: 508
<212> TYPE: PRT
<213> ORGANISM: artificial
<220> FEATURE:
<223> OTHER INFORMATION: 7120_L7_2xGS_Protein sequence

<400> SEQUENCE: 37

```
Met Glu Phe Gly Leu Ser Trp Leu Phe Leu Val Ala Ile Leu Lys Gly
1               5                   10                  15

Ala Leu Ala Ala Gln Thr Asn Phe Met Pro Met Asp Asp Leu Glu Gln
            20                  25                  30

Arg Leu Tyr Glu Gln Phe Ile Leu Gln Gln Gly Leu Glu Gly Gly Gly
        35                  40                  45

Gly Ser Gly Gly Gly Gly Ser Glu Val Gln Leu Val Glu Ser Gly Gly
    50                  55                  60

Gly Leu Val Gln Pro Gly Gly Ser Leu Arg Leu Ser Cys Ala Ala Ser
65                  70                  75                  80

Gly Tyr Asp Phe Thr His Tyr Gly Met Asn Trp Val Arg Gln Ala Pro
                85                  90                  95

Gly Lys Gly Leu Glu Trp Val Gly Trp Ile Asn Thr Tyr Thr Gly Glu
            100                 105                 110

Pro Thr Tyr Ala Ala Asp Phe Lys Arg Arg Phe Thr Phe Ser Leu Asp
        115                 120                 125

Thr Ser Lys Ser Thr Ala Tyr Leu Gln Met Asn Ser Leu Arg Ala Glu
    130                 135                 140

Asp Thr Ala Val Tyr Tyr Cys Ala Lys Tyr Pro Tyr Tyr Tyr Gly Thr
145                 150                 155                 160

Ser His Trp Tyr Phe Asp Val Trp Gly Gln Gly Thr Leu Val Thr Val
                165                 170                 175

Ser Ser Ala Ser Thr Lys Gly Pro Ser Val Phe Pro Leu Ala Pro Ser
            180                 185                 190

Ser Lys Ser Thr Ser Gly Gly Thr Ala Ala Leu Gly Cys Leu Val Lys
        195                 200                 205
```

```
Asp Tyr Phe Pro Glu Pro Val Thr Val Ser Trp Asn Ser Gly Ala Leu
    210                 215                 220
Thr Ser Gly Val His Thr Phe Pro Ala Val Leu Gln Ser Ser Gly Leu
225                 230                 235                 240
Tyr Ser Leu Ser Ser Val Val Thr Val Pro Ser Ser Ser Leu Gly Thr
                245                 250                 255
Gln Thr Tyr Ile Cys Asn Val Asn His Lys Pro Ser Asn Thr Lys Val
            260                 265                 270
Asp Lys Lys Val Glu Pro Lys Ser Cys Asp Lys Thr His Thr Cys Pro
        275                 280                 285
Pro Cys Pro Ala Pro Glu Ala Ala Gly Gly Pro Ser Val Phe Leu Phe
    290                 295                 300
Pro Pro Lys Pro Lys Asp Thr Leu Met Ile Ser Arg Thr Pro Glu Val
305                 310                 315                 320
Thr Cys Val Val Val Asp Val Ser His Glu Asp Pro Glu Val Lys Phe
                325                 330                 335
Asn Trp Tyr Val Asp Gly Val Glu Val His Asn Ala Lys Thr Lys Pro
            340                 345                 350
Arg Glu Glu Gln Tyr Asn Ser Thr Tyr Arg Val Val Ser Val Leu Thr
        355                 360                 365
Val Leu His Gln Asp Trp Leu Asn Gly Lys Glu Tyr Lys Cys Lys Val
    370                 375                 380
Ser Asn Lys Ala Leu Pro Ala Pro Ile Glu Lys Thr Ile Ser Lys Ala
385                 390                 395                 400
Lys Gly Gln Pro Arg Glu Pro Gln Val Tyr Thr Leu Pro Pro Ser Arg
                405                 410                 415
Glu Glu Met Thr Lys Asn Gln Val Ser Leu Thr Cys Leu Val Lys Gly
            420                 425                 430
Phe Tyr Pro Ser Asp Ile Ala Val Glu Trp Glu Ser Asn Gly Gln Pro
        435                 440                 445
Glu Asn Asn Tyr Lys Thr Thr Pro Pro Val Leu Asp Ser Asp Gly Ser
    450                 455                 460
Phe Phe Leu Tyr Ser Lys Leu Thr Val Asp Lys Ser Arg Trp Gln Gln
465                 470                 475                 480
Gly Asn Val Phe Ser Cys Ser Val Met His Glu Ala Leu His Asn His
                485                 490                 495
Tyr Thr Gln Lys Ser Leu Ser Leu Ser Pro Gly Lys
            500                 505

<210> SEQ ID NO 38
<211> LENGTH: 1512
<212> TYPE: DNA
<213> ORGANISM: artificial
<220> FEATURE:
<223> OTHER INFORMATION: 7120_L7_1xGS_DNA sequence

<400> SEQUENCE: 38
atggaattcg gcctgtcttg gctgttcctg gtggccattc tgaagggcgc tctggccgct        60
cagaccaact tcatgcctat ggacgacctg aacagcggc tgtacgagca gttcatcctg       120
cagcaaggac tggaaggagg cggtggatct gaagtgcagc tggttgaaag tggcggcgga       180
ttggttcagc ctggcggatc tctgagactg tcttgtgccg cctctggcta cgacttcacc       240
cactacggca tgaattgggt ccgacaggct cccggcaaag cctgaatg ggtcggatgg       300 atcaacacct ataccggcga gcctacctac gccgccgatt tcaagcggag attcaccttc       360
```

```
tccctggaca cctccaagtc taccgcctac ctgcagatga actccctgag agccgaggac    420
accgccgtgt actactgcgc taagtacccc tactactacg gcaccagcca ctggtacttc    480
gacgtgtggg gacagggcac actggtcaca gtgtcctccg cctctaccaa gggaccctct    540
gtgtttcctc tggctccctc cagcaagtcc acctctggtg aacagctgc tctgggctgc     600
ctggtcaagg actactttcc tgagcctgtg accgtgtcct gggcttctgg tgctctgaca    660
tctggcgtgc acacctttcc agctgtgctg cagtcctccg gcctgtactc tctgtcctct    720
gtcgtgaccg tgccttccag ctctctggga acccagacct acatctgcaa tgtgaaccac    780
aagccttcca caccaaggt cgacaagaag gtggaaccca gtcctgcga taagacccac      840
acctgtcctc catgtcctgc tccagaagct gctggcggcc catccgtgtt tctgttccct    900
ccaaagccta aggacaccct gatgatctct cggacccctg aagtgacctg cgtggtggtg    960
gatgtgtctc acgaggaccc agaagtgaag ttcaattggt acgtggacgg cgtggaagtg   1020
cacaacgcca agaccaagcc tagagaggaa cagtacaact ccacctacag agtggtgtcc   1080
gtgctgaccg tgctgcacca ggattggctg aacggcaaag agtacaagtg caaggtgtcc   1140
aacaaggccc tgcctgctcc tatcgaaaag accatctcca aggccaaggg ccagcctagg   1200
gaaccccagg tttacaccct tgcctccaag cgggaagaga tgaccaagaa ccaggtgtcc   1260
ctgacctgcc tcgtgaaggg cttctaccct tccgatatcg ccgtggaatg ggagagcaat   1320
ggccagcctg agaacaacta caagaccact cctcctgtgc tggactccga cggctcattc   1380
ttcctgtact ccaagctgac agtggacaag tccagatggc agcagggcaa cgtgttctcc   1440
tgctccgtga tgcacgaggc cctgcacaat cactacacac agaagtccct gtctctgtcc   1500
cctggcaagt aa                                                        1512

<210> SEQ ID NO 39
<211> LENGTH: 503
<212> TYPE: PRT
<213> ORGANISM: artificial
<220> FEATURE:
<223> OTHER INFORMATION: 7120_L7_1xGS

<400> SEQUENCE: 39

Met Glu Phe Gly Leu Ser Trp Leu Phe Leu Val Ala Ile Leu Lys Gly
1               5                   10                  15

Ala Leu Ala Ala Gln Thr Asn Phe Met Pro Met Asp Asp Leu Glu Gln
                20                  25                  30

Arg Leu Tyr Glu Gln Phe Ile Leu Gln Gln Gly Leu Glu Gly Gly Gly
            35                  40                  45

Gly Ser Glu Val Gln Leu Val Glu Ser Gly Gly Gly Leu Val Gln Pro
        50                  55                  60

Gly Gly Ser Leu Arg Leu Ser Cys Ala Ala Ser Gly Tyr Asp Phe Thr
65                  70                  75                  80

His Tyr Gly Met Asn Trp Val Arg Gln Ala Pro Gly Lys Gly Leu Glu
                85                  90                  95

Trp Val Gly Trp Ile Asn Thr Tyr Thr Gly Glu Pro Thr Tyr Ala Ala
                100                 105                 110

Asp Phe Lys Arg Arg Phe Thr Phe Ser Leu Asp Thr Ser Lys Ser Thr
            115                 120                 125

Ala Tyr Leu Gln Met Asn Ser Leu Arg Ala Glu Asp Thr Ala Val Tyr
        130                 135                 140

Tyr Cys Ala Lys Tyr Pro Tyr Tyr Tyr Gly Thr Ser His Trp Tyr Phe
```

```
        145                 150                 155                 160
Asp Val Trp Gly Gln Gly Thr Leu Val Thr Val Ser Ser Ala Ser Thr
                165                 170                 175

Lys Gly Pro Ser Val Phe Pro Leu Ala Pro Ser Ser Lys Ser Thr Ser
            180                 185                 190

Gly Gly Thr Ala Ala Leu Gly Cys Leu Val Lys Asp Tyr Phe Pro Glu
        195                 200                 205

Pro Val Thr Val Ser Trp Asn Ser Gly Ala Leu Thr Ser Gly Val His
    210                 215                 220

Thr Phe Pro Ala Val Leu Gln Ser Ser Gly Leu Tyr Ser Leu Ser Ser
225                 230                 235                 240

Val Val Thr Val Pro Ser Ser Leu Gly Thr Gln Thr Tyr Ile Cys
                245                 250                 255

Asn Val Asn His Lys Pro Ser Asn Thr Lys Val Asp Lys Lys Val Glu
            260                 265                 270

Pro Lys Ser Cys Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 40
<211> LENGTH: 1542
<212> TYPE: DNA
<213> ORGANISM: artificial
<220> FEATURE:
<223> OTHER INFORMATION: 7120_L10_3xGS_DNA sequence

<400> SEQUENCE: 40
atggaattcg gcctgtcttg gctgttcctg gtggccattc tgaagggcgc tttggccgct      60
```

```
cagcagaagt tcagcctct ggacgagctg aacagaccc tgtacgagca gttcatgctc    120
cagcaggctt tggaaggcgg cggaggatct ggcggaggcg gtagcggagg cggtggatct    180
gaagtgcagc tggttgaaag tggcggcgga ttggttcagc ctggcggatc tctgagactg    240
tcttgtgccg cctctggcta cgacttcacc cactacggca tgaattgggt ccgacaggct    300
cccggcaaag gcctggaatg ggtcggatgg atcaacacct ataccggcga gcctacctac    360
gccgccgatt tcaagcggag attcaccttc tccctggaca cctccaagtc taccgcctac    420
ctgcagatga actccctgag agccgaggac accgccgtgt actactgcgc taagtacccc    480
tactactacg gcaccagcca ctggtacttc gacgtgtggg gacagggcac actggtcaca    540
gtgtcctccg cctctaccaa ggaccctct gtgtttcctc tggctcctc cagcaagtcc    600 acctctggtg aacagctgc tctgggctgc ctggtcaagg actactttcc tgagcctgtg    660
accgtgtcct gggcttctgg tgctctgaca tctggcgtgc acacctttcc agctgtgctg    720
cagtcctccg gcctgtactc tctgtcctct gtcgtgaccg tgccttccag ctctctggga    780
acccagacct acatctgcaa tgtgaaccac aagccttcca caccaaggt cgacaagaag    840 gtggaaccca gtcctgcga taagacccac acctgtcctc catgtcctgc tccagaagct    900
gctggcggcc catccgtgtt tctgttccct ccaaagccta aggacaccct gatgatctct    960
cggacccctg aagtgacctg cgtggtggtg gatgtgtctc acgaggaccc agaagtgaag    1020
ttcaattggt acgtggacgg cgtggaagtg cacaacgcca agaccaagcc tagagaggaa    1080
cagtacaact ccacctacag agtggtgtcc gtgctgaccg tgctgcacca ggattggctg    1140
aacggcaaag agtacaagtg caaggtgtcc aacaaggccc tgcctgctcc tatcgaaaag    1200
accatctcca aggccaaggg ccagcctagg gaacccagg tttacacctt gcctccaagc    1260
cgggaagaga tgaccaagaa ccaggtgtcc ctgacctgcc tcgtgaaggg cttctaccct    1320
tccgatatcg ccgtggaatg ggagagcaat ggccagcctg agaacaacta caagaccact    1380
cctcctgtgc tggactccga cggctcattc ttcctgtact ccaagctgac agtggacaag    1440
tccagatggc agcagggcaa cgtgttctc tgctccgtga tgcacgaggc cctgcacaat    1500
cactacacac agaagtccct gtctctgtcc cctggcaagt aa    1542
```

<210> SEQ ID NO 41
<211> LENGTH: 513
<212> TYPE: PRT
<213> ORGANISM: artificial
<220> FEATURE:
<223> OTHER INFORMATION: 7120_L10_3xGS_Protein sequence

<400> SEQUENCE: 41

```
Met Glu Phe Gly Leu Ser Trp Leu Phe Leu Val Ala Ile Leu Lys Gly
1               5                   10                  15

Ala Leu Ala Ala Gln Gln Lys Phe Gln Pro Leu Asp Glu Leu Glu Gln
            20                  25                  30

Thr Leu Tyr Glu Gln Phe Met Leu Gln Gln Ala Leu Glu Gly Gly Gly
        35                  40                  45

Gly Ser Gly Gly Gly Gly Ser Gly Gly Gly Gly Ser Glu Val Gln Leu
    50                  55                  60

Val Glu Ser Gly Gly Gly Leu Val Gln Pro Gly Gly Ser Leu Arg Leu
65                  70                  75                  80

Ser Cys Ala Ala Ser Gly Tyr Asp Phe Thr His Tyr Gly Met Asn Trp
                85                  90                  95
```

```
Val Arg Gln Ala Pro Gly Lys Gly Leu Glu Trp Val Gly Trp Ile Asn
            100                 105                 110
Thr Tyr Thr Gly Glu Pro Thr Tyr Ala Ala Asp Phe Lys Arg Phe
        115                 120                 125
Thr Phe Ser Leu Asp Thr Ser Lys Ser Thr Ala Tyr Leu Gln Met Asn
    130                 135                 140
Ser Leu Arg Ala Glu Asp Thr Ala Val Tyr Tyr Cys Ala Lys Tyr Pro
145                 150                 155                 160
Tyr Tyr Tyr Gly Thr Ser His Trp Tyr Phe Asp Val Trp Gly Gln Gly
                165                 170                 175
Thr Leu Val Thr Val Ser Ser Ala Ser Thr Lys Gly Pro Ser Val Phe
            180                 185                 190
Pro Leu Ala Pro Ser Ser Lys Ser Thr Ser Gly Gly Thr Ala Ala Leu
        195                 200                 205
Gly Cys Leu Val Lys Asp Tyr Phe Pro Glu Pro Val Thr Val Ser Trp
    210                 215                 220
Asn Ser Gly Ala Leu Thr Ser Gly Val His Thr Phe Pro Ala Val Leu
225                 230                 235                 240
Gln Ser Ser Gly Leu Tyr Ser Leu Ser Ser Val Val Thr Val Pro Ser
                245                 250                 255
Ser Ser Leu Gly Thr Gln Thr Tyr Ile Cys Asn Val Asn His Lys Pro
            260                 265                 270
Ser Asn Thr Lys Val Asp Lys Lys Val Glu Pro Lys Ser Cys Asp Lys
        275                 280                 285
Thr His Thr Cys Pro Pro Cys Pro Ala Pro Glu Ala Ala Gly Gly Pro
    290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Lys Phe Asn Trp Tyr Val Asp Gly Val Glu Val His Asn
            340                 345                 350
Ala Lys Thr Lys Pro Arg Glu Glu Gln Tyr Asn Ser Thr Tyr Arg Val
        355                 360                 365
Val Ser Val Leu Thr Val Leu His Gln Asp Trp Leu Asn Gly Lys Glu
    370                 375                 380
Tyr Lys Cys Lys Val Ser Asn Lys Ala Leu Pro Ala Pro Ile Glu Lys
385                 390                 395                 400
Thr Ile Ser Lys Ala Lys Gly Gln Pro Arg Glu Pro Gln Val Tyr Thr
                405                 410                 415
Leu Pro Pro Ser Arg Glu Glu Met Thr Lys Asn Gln Val Ser Leu Thr
            420                 425                 430
Cys Leu Val Lys Gly Phe Tyr Pro Ser Asp Ile Ala Val Glu Trp Glu
        435                 440                 445
Ser Asn Gly Gln Pro Glu Asn Asn Tyr Lys Thr Thr Pro Pro Val Leu
    450                 455                 460
Asp Ser Asp Gly Ser Phe Phe Leu Tyr Ser Lys Leu Thr Val Asp Lys
465                 470                 475                 480
Ser Arg Trp Gln Gln Gly Asn Val Phe Ser Cys Ser Val Met His Glu
                485                 490                 495
Ala Leu His Asn His Tyr Thr Gln Lys Ser Leu Ser Leu Ser Pro Gly
            500                 505                 510
Lys
```

<210> SEQ ID NO 42
<211> LENGTH: 1527
<212> TYPE: DNA
<213> ORGANISM: artificial
<220> FEATURE:
<223> OTHER INFORMATION: 7120_L10_2xGS_DNA sequence

<400> SEQUENCE: 42

```
atggaattcg gcctgtcttg gctgttcctg gtggccattc tgaagggcgc tttggccgct      60
cagcagaagt ttcagcctct ggacgagctg aacagaccc tgtacgagca gttcatgctc     120
cagcaggctt tggaaggcgg cggaggatct ggaggcggtg atctgaagt gcagctggtt     180
gaaagtggcg gcggattggt tcagcctggc ggatctctga ctgtcttg tgccgcctct     240
ggctacgact caccccacta cggcatgaat tgggtccgac aggctcccgg caaaggcctg     300
gaatgggtcg gatggatcaa cacctatacc ggcgagccta cctacgccgc cgatttcaag     360
cggagattca ccttctccct ggacacctcc aagtctaccg cctacctgca gatgaactcc     420
ctgagagccg aggacaccgc cgtgtactac tgcgctaagt accctacta ctacggcacc     480
agccactggt acttcgacgt gtggggacag ggcacactgg tcacagtgtc ctccgcctct     540
accaagggac cctctgtgtt ccctctggct ccctccagca gtccacctc tggtggaaca     600
gctgctctgg gctgcctggt caaggactac tttcctgagc ctgtgaccgt gtcctgggct     660
tctggtgctc tgacatctgg cgtgcacacc tttccagctg tgctgcagtc ctccggcctg     720
tactctctgt cctctgtcgt gaccgtgcct ccagctctc tgggaaccca gacctacatc     780
tgcaatgtga accacaagcc ttccaacacc aaggtcgaca agaaggtgga acccaagtcc     840
tgcgataaga cccacacctg tcctccatgt cctgctccag aagctgctgg cggcccatcc     900
gtgtttctgt tccctccaaa gcctaaggac accctgatga tctctcggac ccctgaagtg     960
acctgcgtgg tggtggatgt gtctcacgag gacccagaag tgaagttcaa ttggtacgtg    1020
gacggcgtgg aagtgcacaa cgccaagacc aagcctagag aggaacagta caactccacc    1080
tacagagtgg tgtccgtgct gaccgtgctg caccaggatt ggctgaacgg caaagagtac    1140
aagtgcaagg tgtccaacaa ggccctgcct gctcctatcg aaaagaccat ctccaaggcc    1200
aagggccagc ctagggaacc ccaggtttac accttgcctc caagccggga agagatgacc    1260
aagaaccagg tgtccctgac ctgcctcgtg aagggcttct acccttccga tatcgccgtg    1320
gaatgggaga gcaatggcca gcctgagaac aactacaaga ccactcctcc tgtgctggac    1380
tccgacggct cattcttcct gtactccaag ctgacagtgg acaagtccag atggcagcag    1440
ggcaacgtgt tctcctgctc cgtgatgcac gaggccctgc acaatcacta cacacagaag    1500
tccctgtctc tgtccctgg caagtaa                                         1527
```

<210> SEQ ID NO 43
<211> LENGTH: 508
<212> TYPE: PRT
<213> ORGANISM: artificial
<220> FEATURE:
<223> OTHER INFORMATION: 7120_L10_2xGS_Protein sequence

<400> SEQUENCE: 43

```
Met Glu Phe Gly Leu Ser Trp Leu Phe Leu Val Ala Ile Leu Lys Gly
1               5                   10                  15

Ala Leu Ala Ala Gln Gln Lys Phe Gln Pro Leu Asp Glu Leu Glu Gln
            20                  25                  30
```

```
Thr Leu Tyr Glu Gln Phe Met Leu Gln Gln Ala Leu Glu Gly Gly
         35                  40                  45
Gly Ser Gly Gly Gly Ser Glu Val Gln Leu Val Glu Ser Gly Gly
 50                  55                  60
Gly Leu Val Gln Pro Gly Gly Ser Leu Arg Leu Ser Cys Ala Ala Ser
 65                  70                  75                  80
Gly Tyr Asp Phe Thr His Tyr Gly Met Asn Trp Val Arg Gln Ala Pro
                 85                  90                  95
Gly Lys Gly Leu Glu Trp Val Gly Trp Ile Asn Thr Tyr Thr Gly Glu
                100                 105                 110
Pro Thr Tyr Ala Ala Asp Phe Lys Arg Arg Phe Thr Phe Ser Leu Asp
        115                 120                 125
Thr Ser Lys Ser Thr Ala Tyr Leu Gln Met Asn Ser Leu Arg Ala Glu
    130                 135                 140
Asp Thr Ala Val Tyr Tyr Cys Ala Lys Tyr Pro Tyr Tyr Tyr Gly Thr
145                 150                 155                 160
Ser His Trp Tyr Phe Asp Val Trp Gly Gln Gly Thr Leu Val Thr Val
                165                 170                 175
Ser Ser Ala Ser Thr Lys Gly Pro Ser Val Phe Pro Leu Ala Pro Ser
            180                 185                 190
Ser Lys Ser Thr Ser Gly Gly Thr Ala Ala Leu Gly Cys Leu Val Lys
    195                 200                 205
Asp Tyr Phe Pro Glu Pro Val Thr Val Ser Trp Asn Ser Gly Ala Leu
        210                 215                 220
Thr Ser Gly Val His Thr Phe Pro Ala Val Leu Gln Ser Ser Gly Leu
225                 230                 235                 240
Tyr Ser Leu Ser Ser Val Val Thr Val Pro Ser Ser Ser Leu Gly Thr
                245                 250                 255
Gln Thr Tyr Ile Cys Asn Val Asn His Lys Pro Ser Asn Thr Lys Val
            260                 265                 270
Asp Lys Lys Val Glu Pro Lys Ser Cys Asp Lys Thr His Thr Cys Pro
    275                 280                 285
Pro Cys Pro Ala Pro Glu Ala Ala Gly Gly Pro Ser Val Phe Leu Phe
290                 295                 300
Pro Pro Lys Pro Lys Asp Thr Leu Met Ile Ser Arg Thr Pro Glu Val
305                 310                 315                 320
Thr Cys Val Val Val Asp Val Ser His Glu Asp Pro Glu Val Lys Phe
                325                 330                 335
Asn Trp Tyr Val Asp Gly Val Glu Val His Asn Ala Lys Thr Lys Pro
            340                 345                 350
Arg Glu Glu Gln Tyr Asn Ser Thr Tyr Arg Val Val Ser Val Leu Thr
    355                 360                 365
Val Leu His Gln Asp Trp Leu Asn Gly Lys Glu Tyr Lys Cys Lys Val
        370                 375                 380
Ser Asn Lys Ala Leu Pro Ala Pro Ile Glu Lys Thr Ile Ser Lys Ala
385                 390                 395                 400
Lys Gly Gln Pro Arg Glu Pro Gln Val Tyr Thr Leu Pro Pro Ser Arg
                405                 410                 415
Glu Glu Met Thr Lys Asn Gln Val Ser Leu Thr Cys Leu Val Lys Gly
            420                 425                 430
Phe Tyr Pro Ser Asp Ile Ala Val Glu Trp Glu Ser Asn Gly Gln Pro
    435                 440                 445
Glu Asn Asn Tyr Lys Thr Thr Pro Pro Val Leu Asp Ser Asp Gly Ser
```

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
                500                 505

<210> SEQ ID NO 44
<211> LENGTH: 1512
<212> TYPE: DNA
<213> ORGANISM: artificial
<220> FEATURE:
<223> OTHER INFORMATION: 712O_L10_3xGS_DNA sequence

<400> SEQUENCE: 44

| | |
|---|---|
| atggaattcg gcctgtcttg gctgttcctg gtggccattc tgaagggcgc tttggccgct | 60 |
| cagcagaagt tcagcctct ggacgagctg aacagaccc tgtacgagca gttcatgctc | 120 |
| cagcaggctt tggaaggagg cggtggatct gaagtgcagc tggttgaaag tggcggcgga | 180 |
| ttggttcagc ctggcggatc tctgagactg tcttgtgccg cctctggcta cgacttcacc | 240 |
| cactacggca tgaattgggt ccgacaggct cccggcaaag gcctggaatg ggtcggatgg | 300 |
| atcaacacct ataccggcga gcctacctac gccgccgatt tcaagcggag attcaccttc | 360 |
| tccctggaca cctccaagtc taccgcctac ctgcagatga actccctgag agccgaggac | 420 |
| accgccgtgt actactgcgc taagtacccc tactactacg gcaccagcca ctggtacttc | 480 |
| gacgtgtggg gacagggcac actggtcaca gtgtcctccg cctctaccaa gggaccctct | 540 |
| gtgtttcctc tggctcccct cagcaagtcc acctctggtg aacagctgc tctgggctgc | 600 |
| ctggtcaagg actactttcc tgagcctgtg accgtgtcct gggcttctgg tgctctgaca | 660 |
| tctggcgtgc acacctttcc agctgtgctg cagtcctccg gcctgtactc tctgtcctct | 720 |
| gtcgtgaccg tgccttccag ctctctggga acccagacct acatctgcaa tgtgaaccac | 780 |
| aagccttcca caccaaggt cgacaagaag gtggaaccca gtcctgcga taagacccac | 840 |
| acctgtcctc catgtcctgc tccagaagct gctggcggcc atccgtgtt tctgttccct | 900 |
| ccaaagccta aggacaccct gatgatctct cggacccctg aagtgacctg cgtggtggtg | 960 |
| gatgtgtctc acgaggaccc agaagtgaag ttcaattggt acgtggacgg cgtggaagtg | 1020 |
| cacaacgcca agaccaagcc tagagaggaa cagtacaact ccacctacag agtggtgtcc | 1080 |
| gtgctgaccg tgctgcacca ggattggctg aacggcaaag agtacaagtg caaggtgtcc | 1140 |
| aacaaggccc tgcctgctcc tatcgaaaag accatctcca aggccaaggg ccagcctagg | 1200 |
| gaacccagg tttacacctt gcctccaagc cgggaagaga tgaccaagaa ccaggtgtcc | 1260 |
| ctgacctgcc tcgtgaaggg cttctaccct tccgatatcg ccgtggaatg ggagagcaat | 1320 |
| ggccagcctg agaacaacta caagaccact cctcctgtgc tggactccga cggctcattc | 1380 |
| ttcctgtact ccaagctgac agtggacaag tccagatggc agcagggcaa cgtgttctcc | 1440 |
| tgctccgtga tgcacgaggc cctgcacaat cactacacac agaagtccct gtctctgtcc | 1500 |
| cctggcaagt aa | 1512 |

<210> SEQ ID NO 45
<211> LENGTH: 503
<212> TYPE: PRT
<213> ORGANISM: artificial
<220> FEATURE:

<223> OTHER INFORMATION: 7120_L10_1xGS_Protein sequence

<400> SEQUENCE: 45

```
Met Glu Phe Gly Leu Ser Trp Leu Phe Leu Val Ala Ile Leu Lys Gly
1               5                   10                  15

Ala Leu Ala Ala Gln Gln Lys Phe Gln Pro Leu Asp Glu Leu Glu Gln
            20                  25                  30

Thr Leu Tyr Glu Gln Phe Met Leu Gln Ala Leu Glu Gly Gly Gly
        35                  40                  45

Gly Ser Glu Val Gln Leu Val Glu Ser Gly Gly Leu Val Gln Pro
    50                  55                  60

Gly Gly Ser Leu Arg Leu Ser Cys Ala Ala Ser Gly Tyr Asp Phe Thr
65                  70                  75                  80

His Tyr Gly Met Asn Trp Val Arg Gln Ala Pro Gly Lys Gly Leu Glu
                85                  90                  95

Trp Val Gly Trp Ile Asn Thr Tyr Thr Gly Glu Pro Thr Tyr Ala Ala
            100                 105                 110

Asp Phe Lys Arg Arg Phe Thr Phe Ser Leu Asp Thr Ser Lys Ser Thr
        115                 120                 125

Ala Tyr Leu Gln Met Asn Ser Leu Arg Ala Glu Asp Thr Ala Val Tyr
    130                 135                 140

Tyr Cys Ala Lys Tyr Pro Tyr Tyr Gly Thr Ser His Trp Tyr Phe
145                 150                 155                 160

Asp Val Trp Gly Gln Gly Thr Leu Val Thr Val Ser Ala Ser Thr
            165                 170                 175

Lys Gly Pro Ser Val Phe Pro Leu Ala Pro Ser Ser Lys Ser Thr Ser
        180                 185                 190

Gly Gly Thr Ala Ala Leu Gly Cys Leu Val Lys Asp Tyr Phe Pro Glu
    195                 200                 205

Pro Val Thr Val Ser Trp Asn Ser Gly Ala Leu Thr Ser Gly Val His
    210                 215                 220

Thr Phe Pro Ala Val Leu Gln Ser Ser Gly Leu Tyr Ser Leu Ser Ser
225                 230                 235                 240

Val Val Thr Val Pro Ser Ser Ser Leu Gly Thr Gln Thr Tyr Ile Cys
            245                 250                 255

Asn Val Asn His Lys Pro Ser Asn Thr Lys Val Asp Lys Lys Val Glu
        260                 265                 270

Pro Lys Ser Cys Asp Lys Thr His Thr Cys Pro Pro Cys Pro Ala Pro
    275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
        340                 345                 350

Asn Ser Thr Tyr Arg Val Val Ser Val Leu Thr Val Leu His Gln Asp
    355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400
```

```
Glu Pro Gln Val Tyr Thr Leu Pro Pro Ser Arg Glu Glu Met Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
                500

<210> SEQ ID NO 46
<211> LENGTH: 1512
<212> TYPE: DNA
<213> ORGANISM: artificial
<220> FEATURE:
<223> OTHER INFORMATION: 7120_C terminal L7_1xGS_DNA sequence

<400> SEQUENCE: 46
atggaattcg gcctgtcttg gctgttcctg gtggccattc tgaagggcgc tctggccgaa      60
gtgcagttgg ttgaatctgg tggcggattg gtgcagcctg gcggatctct gagactgtct     120
tgtgccgcct ctggctacga tttcacccac tacggcatga attgggtccg acaggctcct     180
ggcaaaggcc tggaatgggt cggatggatc aatacctata ccggcgagcc tacctacgcc     240
gccgacttca gagaagatt caccttctcc ctggacacct ccaagtctac cgcctacctg     300
cagatgaact ccctgagagc tgaggacacc gccgtgtact actgcgctaa gtaccctac      360 tactacggca ccagccactg gtactttgat gtgtgggac agggcaccct ggtcaccgtt     420
tcttccgctt ctacaaaggg acccagcgtg ttccctctgg ctcctagctc taagtctacc     480
tctggcggaa ccgctgctct gggctgtctg gtcaaggatt acttccctga gcctgtgacc     540
gtgtcctgga atagtggtgc tctgacatcc ggcgtgcaca ccttccagc tgtgctgcag     600 tcctctggcc tgtactctct gtcctctgtc gtgaccgtcc cttctagctc tctgggcacc     660
cagacctaca tctgcaacgt gaaccacaag ccttccaaca ctaaggtgga caagaaggtg     720
gaacccaagt cctgcgataa gacccacacc tgtcctccat gtcctgcacc tgaagctgct     780 ggcggacccct ctgtgttcct gtttcctcca aagcctaagg acaccctgat gatctctcgg    840
acccctgaag tgacctgcgt ggtggtggat gtgtctcacg aggacccaga agtgaagttc     900
aattggtacg tggacggcgt ggaagtgcac aacgccaaga ccaagcctag agaggaacag     960
tacaactcca cctacagagt ggtgtccgtg ctgaccgtgc tgcaccagga ttggctgaac    1020
ggcaaagagt acaagtgcaa ggtgtccaac aaggccctgc ctgctcctat cgaaaagacc    1080
atctctaagg ctaagggcca gcctcgggaa cctcaggttt acacactgcc tccaagccgg    1140
gaagagatga ccaagaatca ggtgtccctg acctgcctcg tgaagggctt ctacccttcc    1200
gatatcgccg tcgaatggga gtccaatggc cagcctgaga caactacaa gacaacccct    1260 cctgtgctgg actccgacgg ctcattcttc ctgtactcca agctgacagt ggacaagtct    1320
cggtggcagc agggcaacgt gttctcctgt tctgtgatgc acgaggccct gcacaaccac    1380
tacacacaga agtcactctc cctttccccg ggcgctggcg gcggaggatc tgctcagacc    1440
```

```
aacttcatgc tatggacgac cctggaacag cggctgtacg agcagttcat cctgcagcaa    1500
ggactggaat ga                                                        1512
```

<210> SEQ ID NO 47
<211> LENGTH: 503
<212> TYPE: PRT
<213> ORGANISM: artificial
<220> FEATURE:
<223> OTHER INFORMATION: 712O_C terminal L7_1xGS_Protein sequence

<400> SEQUENCE: 47

| | | | | | | | | | | | | | | | |
|---|---|---|---|---|---|---|---|---|---|---|---|---|---|---|---|
| Met | Glu | Phe | Gly | Leu | Ser | Trp | Leu | Phe | Leu | Val | Ala | Ile | Leu | Lys | Gly |
| 1 | | | | 5 | | | | | 10 | | | | | 15 | |

Ala Leu Ala Glu Val Gln Leu Val Glu Ser Gly Gly Gly Leu Val Gln
           20                  25                  30

Pro Gly Gly Ser Leu Arg Leu Ser Cys Ala Ala Ser Gly Tyr Asp Phe
       35                  40                  45

Thr His Tyr Gly Met Asn Trp Val Arg Gln Ala Pro Gly Lys Gly Leu
   50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
               85                  90                  95

Thr Ala Tyr Leu Gln Met Asn Ser Leu Arg Ala Glu Asp Thr Ala Val
           100                 105                 110

Tyr Tyr Cys Ala Lys Tyr Pro Tyr Tyr Gly Thr Ser His Trp Tyr
       115                 120                 125

Phe Asp Val Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
               165                 170                 175

Glu Pro Val Thr Val Ser Trp Asn Ser Gly Ala Leu Thr Ser Gly Val
           180                 185                 190

His Thr Phe Pro Ala Val Leu Gln Ser Ser Gly Leu Tyr Ser Leu Ser
       195                 200                 205

Ser Val Val Thr Val Pro Ser Ser Ser Leu Gly Thr Gln Thr Tyr Ile
   210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
               245                 250                 255

Pro Glu Ala Ala Gly Gly Pro Ser Val Phe Leu Phe Pro Pro Lys Pro
           260                 265                 270

Lys Asp Thr Leu Met Ile Ser Arg Thr Pro Glu Val Thr Cys Val Val
       275                 280                 285

Val Asp Val Ser His Glu Asp Pro Glu Val Lys Phe Asn Trp Tyr Val
   290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
               325                 330                 335

Asp Trp Leu Asn Gly Lys Glu Tyr Lys Cys Lys Val Ser Asn Lys Ala
           340                 345                 350

```
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Glu Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Ala Gly Gly Gly Ser Ala Gln Thr
465                 470                 475                 480
Asn Phe Met Pro Met Asp Asp Leu Glu Gln Arg Leu Tyr Glu Gln Phe
                485                 490                 495
Ile Leu Gln Gln Gly Leu Glu
            500

<210> SEQ ID NO 48
<211> LENGTH: 1527
<212> TYPE: DNA
<213> ORGANISM: artificial
<220> FEATURE:
<223> OTHER INFORMATION: 7120_L7_C_2xGS_DNA sequence

<400> SEQUENCE: 48
atggaattcg gcctgtcttg gctgttcctg gtggccattc tgaagggcgc tctggccgaa      60
gtgcagttgg ttgaatctgg tgcggattg gtgcagcctg gcggatctct gagactgtct     120
tgtgccgcct ctggctacga tttcacccac tacggcatga attgggtccg acaggctcct     180
ggcaaaggcc tggaatgggt cggatggatc aatacctata ccggcgagcc tacctacgcc     240
gccgacttca gagaagatt caccttctcc ctggacacct ccagtctac cgcctacctg     300 cagatgaact ccctgagagc tgaggacacc gccgtgtact actgcgctaa gtacccctac     360
tactacggca ccagccactg gtactttgat gtgtggggac agggcaccct ggtcaccgtt     420
tcttccgctt ctacaaaggg acccagcgtg ttccctctgg ctcctagctc taagtctacc     480
tctggcggaa ccgctgctct gggctgtctg gtcaaggatt acttccctga gcctgtgacc     540
gtgtcctgga atagtggtgc tctgacatcc ggcgtgcaca cctttccagc tgtgctgcag     600
tcctctggcc tgtactctct gtcctctgtc gtgaccgtcc cttctagctc tctgggcacc     660
cagacctaca tctgcaacgt gaaccacaag ccttccaaca ctaaggtgga caagaaggtg     720
gaacccaagt cctgcgataa gacccacacc tgtcctccat gtcctgcacc tgaagctgct     780
ggcggaccct ctgtgttcct gtttcctcca agcctaagg acaccctgat gatctctcgg     840
acccctgaag tgacctgcgt ggtggtggat gtgtctcacg aggacccaga agtgaagttc     900
aattggtacg tggacggcgt ggaagtgcac aacgccaaga ccaagcctag agaggaacag     960
tacaactcca cctacagagt ggtgtccgtg ctgaccgtgc tgcaccagga ttggctgaac    1020
ggcaaagagt acaagtgcaa ggtgtccaac aaggccctgc ctgctcctat cgaaaagacc    1080
atctctaagg ctaagggcca gcctcgggaa cctcaggttt acacactgcc tccaagccgg    1140
```

-continued

```
gaagagatga ccaagaatca ggtgtccctg acctgcctcg tgaagggctt ctacccttcc    1200
gatatcgccg tcgaatggga gtccaatggc cagcctgaga caactacaa gacaaccct     1260 cctgtgctgg actccgacgg ctcattcttc ctgtactcca agctgacagt ggacaagtct    1320
cggtggcagc agggcaacgt gttctcctgt tctgtgatgc acgaggccct gcacaaccac    1380
tacacacaga agtcactctc cctttccccg ggcgctggcg gcggaggatc tggcggaggc    1440
ggtagcgctc agaccaactt catgcctatg gacgacctgg aacagcggct gtacgagcag    1500
ttcatcctgc agcaaggact ggaatga                                        1527
```

<210> SEQ ID NO 49
<211> LENGTH: 508
<212> TYPE: PRT
<213> ORGANISM: artificial
<220> FEATURE:
<223> OTHER INFORMATION: 7120_L7_C_2xGS_protein sequence

<400> SEQUENCE: 49

```
Met Glu Phe Gly Leu Ser Trp Leu Phe Leu Val Ala Ile Leu Lys Gly
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Gly Thr Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Ala Ala Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
```

```
Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
    450                 455                 460

Ser Leu Ser Leu Ser Pro Gly Ala Gly Gly Gly Ser Gly Gly Gly
465                 470                 475                 480

Gly Ser Ala Gln Thr Asn Phe Met Pro Met Asp Asp Leu Glu Gln Arg
                485                 490                 495

Leu Tyr Glu Gln Phe Ile Leu Gln Gln Gly Leu Glu
                500                 505

<210> SEQ ID NO 50
<211> LENGTH: 1542
<212> TYPE: DNA
<213> ORGANISM: artificial
<220> FEATURE:
<223> OTHER INFORMATION: 7120_L7_C_3xGS_DNA sequence

<400> SEQUENCE: 50
atggaattcg gcctgtcttg gctgttcctg gtggccattc tgaagggcgc tctggccgaa      60
gtgcagttgg ttgaatctgg tggcggattg gtgcagcctg gcggatctct gagactgtct     120
tgtgccgcct ctggctacga tttcacccac tacggcatga attgggtccg acaggctcct     180
ggcaaaggcc tggaatgggt cggatggatc aataccatat ccggcgagcc tacctacgcc     240
gccgacttca gagaagatt caccttctcc ctggacacct ccaagtctac cgcctacctg     300
cagatgaact ccctgagagc tgaggacacc gccgtgtact actgcgctaa gtaccccac     360 tactacggca ccagccactg gtactttgat gtgtgggac agggcaccct ggtcaccgtt     420
tcttccgctt ctacaaaggg acccagcgtg ttccctctgg ctcctagctc taagtctacc     480
tctggcggaa ccgctgctct gggctgtctg gtcaaggatt acttccctga gcctgtgacc     540
gtgtcctgga atagtggtgc tctgacatcc ggcgtgcaca cctttccagc tgtgctgcag     600
tcctctggcc tgtactctct gtcctctgtc gtgaccgtcc cttctagctc tctgggcacc     660
cagacctaca tctgcaacgt gaaccacaag ccttccaaca ctaaggtgga caagaaggtg     720
gaacccaagt cctgcgataa gacccacacc tgtcctccat gtcctgcacc tgaagctgct     780
ggcggaccct ctgtgttcct gtttcctcca aagcctaagg acaccctgat gatctctcgg     840
```

```
acccctgaag tgacctgcgt ggtggtggat gtgtctcacg aggacccaga agtgaagttc      900
aattggtacg tggacggcgt ggaagtgcac aacgccaaga ccaagcctag agaggaacag      960
tacaactcca cctacagagt ggtgtccgtg ctgaccgtgc tgcaccagga ttggctgaac     1020
ggcaaagagt acaagtgcaa ggtgtccaac aaggccctgc ctgctcctat cgaaaagacc     1080
atctctaagg ctaagggcca gcctcgggaa cctcaggttt acacactgcc tccaagccgg     1140
gaagagatga ccaagaatca ggtgtccctg acctgcctcg tgaagggctt ctaccttcc      1200
gatatcgccg tcgaatggga gtccaatggc cagcctgaga caactacaa gacaaccct      1260
cctgtgctgg actccgacgg ctcattcttc ctgtactcca agctgacagt ggacaagtct     1320
cggtggcagc agggcaacgt gttctcctgt tctgtgatgc acgaggccct gcacaaccac     1380
tacacacaga agtcactctc cctttccccg ggcgctggcg gcggaggatc tggcggaggc     1440
ggtagcggtg gtggtggatc tgctcagacc aacttcatgc ctatggacga cctggaacag     1500
cggctgtacg agcagttcat cctgcagcaa ggactggaat ga                       1542
```

<210> SEQ ID NO 51
<211> LENGTH: 513
<212> TYPE: PRT
<213> ORGANISM: artificial
<220> FEATURE:
<223> OTHER INFORMATION: 7120_L7_C_3xGS_Protein sequence

<400> SEQUENCE: 51

```
Met Glu Phe Gly Leu Ser Trp Leu Phe Leu Val Ala Ile Leu Lys Gly
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Tyr Gly Thr Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240
```

Glu Pro Lys Ser Cys Asp Lys Thr His Thr Cys Pro Pro Cys Pro Ala
            245                 250                 255

Pro Glu Ala Ala Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ala Gly Gly Gly Ser Gly Gly Gly
465                 470                 475                 480

Gly Ser Gly Gly Gly Ser Ala Gln Thr Asn Phe Met Pro Met Asp
                485                 490                 495

Asp Leu Glu Gln Arg Leu Tyr Glu Gln Phe Ile Leu Gln Gln Gly Leu
            500                 505                 510

Glu

<210> SEQ ID NO 52
<211> LENGTH: 1512
<212> TYPE: DNA
<213> ORGANISM: artificial
<220> FEATURE:
<223> OTHER INFORMATION: 7120_L15_C_1xGS_DNA sequence

<400> SEQUENCE: 52
atggaattcg gcctgtcttg gctgttcctg gtggccattc tgaagggcgc tctggccgaa      60
gtgcagttgg ttgaatctgg tggcggattg gtgcagcctg gcggatctct gagactgtct     120
tgtgccgcct ctggctacga tttcacccac tacggcatga attgggtccg acaggctcct     180
ggcaaaggcc tggaatgggt cggatggatc aatacctata ccggcgagcc tacctacgcc     240
gccgacttca gagaagatt caccttctcc ctggacacct ccaagtctac cgcctacctg     300
cagatgaact ccctgagagc tgaggacacc gccgtgtact actgcgctaa gtaccccctac     360 tactacggca ccagccactg gtactttgat gtgtggggac agggcacccct ggtcaccgtt     420 tcttccgctt ctacaaaggg acccagcgtg ttccctctgg ctcctagctc taagtctacc     480

-continued

```
tctggcggaa ccgctgctct gggctgtctg gtcaaggatt acttccctga gcctgtgacc    540
gtgtcctgga atagtggtgc tctgacatcc ggcgtgcaca cctttccagc tgtgctgcag    600
tcctctggcc tgtactctct gtcctctgtc gtgaccgtcc cttctagctc tctgggcacc    660
cagacctaca tctgcaacgt gaaccacaag ccttccaaca ctaaggtgga caagaaggtg    720
gaacccaagt cctgcgataa gacccacacc tgtcctccat gtcctgcacc tgaagctgct    780
ggcggaccct ctgtgttcct gtttcctcca agcctaagg acaccctgat gatctctcgg    840 accccctgaag tgacctgcgt ggtggtggat gtgtctcacg aggacccaga agtgaagttc    900
aattggtacg tggacggcgt ggaagtgcac aacgccaaga ccaagcctag agaggaacag    960
tacaactcca cctacagagt ggtgtccgtg ctgaccgtgc tgcaccagga ttggctgaac    1020
ggcaaagagt acaagtgcaa ggtgtccaac aaggccctgc ctgctcctat cgaaaagacc    1080
atctctaagg ctaagggcca gcctcgggaa cctcaggttt acacactgcc tccaagccgg    1140
gaagagatga ccaagaatca ggtgtccctg acctgcctcg tgaagggctt ctacccttcc    1200
gatatcgccg tcgaatggga gtccaatggc agcctgaga caactacaa gacaaccccct    1260 cctgtgctgg actccgacgg ctcattcttc ctgtactcca agctgacagt ggacaagtct    1320
cggtggcagc agggcaacgt gttctcctgt tctgtgatgc acgaggccct gcacaaccac    1380
tacacacaga gtcactctc ccttcccccg ggcgctggcg gcggaggatc tgcccagcag    1440
aagtatcagc tctggacga gctggacaag accctgtacg accagttcat gctccagcag    1500
ggactggaat ga                                                       1512
```

<210> SEQ ID NO 53
<211> LENGTH: 503
<212> TYPE: PRT
<213> ORGANISM: artificial
<220> FEATURE:
<223> OTHER INFORMATION: 712O_L15_C_1xGS_Protein sequence

<400> SEQUENCE: 53

```
Met Glu Phe Gly Leu Ser Trp Leu Phe Leu Val Ala Ile Leu Lys Gly
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Gly Thr Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175
```

```
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Ser Leu Gly Thr Gln Thr Tyr Ile
    210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                245                 250                 255
Pro Glu Ala Ala Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
        275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Glu Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Ala Gly Gly Gly Ser Ala Gln Gln
465                 470                 475                 480
Lys Tyr Gln Pro Leu Asp Glu Leu Asp Lys Thr Leu Tyr Asp Gln Phe
                485                 490                 495
Met Leu Gln Gln Gly Leu Glu
            500
```

<210> SEQ ID NO 54
<211> LENGTH: 1526
<212> TYPE: DNA
<213> ORGANISM: artificial
<220> FEATURE:
<223> OTHER INFORMATION: 7120_L15_C_2xGS_DNA sequence

<400> SEQUENCE: 54

```
tggaattcgg cctgtcttgg ctgttcctgg tggccattct gaagggcgct ctggccgaag    60
tgcagttggt tgaatctggt ggcggattgg tgcagcctgg cggatctctg agactgtctt   120
gtgccgcctc tggctacgat ttcacccact acggcatgaa ttgggtccga caggctcctg   180
```

```
gcaaaggcct ggaatgggtc ggatggatca ataccctatac cggcgagcct acctacgccg    240
ccgacttcaa gagaagattc accttctccc tggacacctc caagtctacc gcctacctgc    300
agatgaactc cctgagagct gaggacaccg ccgtgtacta ctgcgctaag taccccctact    360 actacggcac cagccactgg tactttgatg tgtggggaca gggcaccctg gtcaccgttt    420
cttccgcttc tacaaaggga cccagcgtgt tccctctggc tcctagctct aagtctacct    480
ctggcggaac cgctgctctg gctgtctgg tcaaggatta cttccctgag cctgtgaccg    540
tgtcctggaa tagtggtgct ctgacatccg gcgtgcacac cttccagct gtgctgcagt    600 cctctggcct gtactctctg tcctctgtcg tgaccgtccc ttctagctct ctgggcaccc    660
agacctacat ctgcaacgtg aaccacaagc cttccaacac taaggtggac aagaaggtgg    720
aacccaagtc ctgcgataag acccacacct gtcctccatg tcctgcacct gaagctgctg    780 gcggacccctc tgtgttcctg tttcctccaa agcctaagga caccctgatg atctctcgga    840
cccctgaagt gacctgcgtg gtggtggatg tgtctcacga ggacccagaa gtgaagttca    900
attggtacgt ggacggcgtg gaagtgcaca acgccaagac caagcctaga gaggaacagt    960
acaactccac ctacagagtg gtgtccgtgc tgaccgtgct gcaccaggat tggctgaacg   1020
gcaaagagta caagtgcaag gtgtccaaca aggccctgcc tgctcctatc gaaaagacca   1080
tctctaaggc taagggccag cctcgggaac ctcaggtttta cacactgcct ccaagccggg   1140
aagagatgac caagaatcag gtgtccctga cctgcctcgt gaagggcttc tacccttccg   1200
atatcgccgt cgaatgggag tccaatggcc agcctgagaa caactacaag acaacccctc   1260
ctgtgctgga ctccgacggc tcattcttcc tgtactccaa gctgacagtg gacaagtctc   1320
ggtggcagca gggcaacgtg ttctcctgtt ctgtgatgca cgaggccctg cacaaccact   1380
acacacagaa gtcactctcc ctttccccgg gcgctggcgg cggaggatct ggcggaggcg   1440
gtagcgccca gcagaagtat cagcctctgg acgagctgga caagaccctg tacgaccagt   1500
tcatgctcca gcagggactg gaatga                                          1526
```

<210> SEQ ID NO 55
<211> LENGTH: 508
<212> TYPE: PRT
<213> ORGANISM: artificial
<220> FEATURE:
<223> OTHER INFORMATION: 7120_L15_C_2xGS_Protein sequence

<400> SEQUENCE: 55

```
Met Glu Phe Gly Leu Ser Trp Leu Phe Leu Val Ala Ile Leu Lys Gly
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Gly Thr Ser His Trp Tyr
        115                 120                 125
```

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Ala Ala Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Ala Gly Gly Gly Ser Gly Gly Gly
465                 470                 475                 480

Gly Ser Ala Gln Gln Lys Tyr Gln Pro Leu Asp Glu Leu Asp Lys Thr
                485                 490                 495

Leu Tyr Asp Gln Phe Met Leu Gln Gln Gly Leu Glu
        500                 505

<210> SEQ ID NO 56
<211> LENGTH: 1542
<212> TYPE: DNA
<213> ORGANISM: artificial
<220> FEATURE:

<223> OTHER INFORMATION: 712O_L15_C_3xGS_DNA sequence

<400> SEQUENCE: 56

| | |
|---|---|
| atggaattcg gcctgtcttg gctgttcctg gtggccattc tgaagggcgc tctggccgaa | 60 |
| gtgcagttgg ttgaatctgg tggcggattg gtgcagcctg gcggatctct gagactgtct | 120 |
| tgtgccgcct ctggctacga tttcacccac tacggcatga attgggtccg acaggctcct | 180 |
| ggcaaaggcc tggaatgggt cggatggatc aatacctata ccggcgagcc tacctacgcc | 240 |
| gccgacttca agagaagatt caccttctcc ctggacacct ccaagtctac cgcctacctg | 300 |
| cagatgaact ccctgagagc tgaggacacc gccgtgtact actgcgctaa gtaccccta c | 360 |
| tactacggca ccagccactg gtactttgat gtgtggggac agggcaccct ggtcaccgtt | 420 |
| tcttccgctt ctacaaaggg acccagcgtg ttccctctgg ctcctagctc taagtctacc | 480 |
| tctggcggaa ccgctgctct gggctgtctg gtcaaggatt acttccctga gcctgtgacc | 540 |
| gtgtcctgga atagtggtgc tctgacatcc ggcgtgcaca cctttccagc tgtgctgcag | 600 |
| tcctctggcc tgtactctct gtcctctgtc gtgaccgtcc cttctagctc tctgggcacc | 660 |
| cagacctaca tctgcaacgt gaaccacaag ccttccaaca ctaaggtgga caagaaggtg | 720 |
| gaacccaagt cctgcgataa gacccacacc tgtcctccat gtcctgcacc tgaagctgct | 780 |
| ggcggaccct ctgtgttcct gtttcctcca aagcctaagg acaccctgat gatctctcgg | 840 |
| acccctgaag tgacctgcgt ggtggtggat gtgtctcacg aggacccaga agtgaagttc | 900 |
| aattggtacg tggacggcgt ggaagtgcac aacgccaaga ccaagcctag agaggaacag | 960 |
| tacaactcca cctacagagt ggtgtccgtg ctgaccgtgc tgcaccagga ttggctgaac | 1020 |
| ggcaaagagt acaagtgcaa ggtgtccaac aaggccctgc ctgctcctat cgaaaagacc | 1080 |
| atctctaagg ctaagggcca gcctcgggaa cctcaggttt acacactgcc tccaagccgg | 1140 |
| gaagagatga ccaagaatca ggtgtccctg acctgcctcg tgaagggctt ctacccttcc | 1200 |
| gatatcgccg tcgaatggga gtccaatggc cagcctgaga caactacaa gacaacccct | 1260 |
| cctgtgctgg actccgacgg ctcattcttc ctgtactcca agctgacagt ggacaagtct | 1320 |
| cggtggcagc agggcaacgt gttctcctgt tctgtgatgc acgaggccct gcacaaccac | 1380 |
| tacacacaga agtcactctc ccttttccccg ggcgctggcg gcggaggatc tggcggaggc | 1440 |
| ggtagcggtg gtggtggatc tgcccagcag aagtatcagc ctctggacga gctggacaag | 1500 |
| accctgtacg accagttcat gctccagcag ggactggaat ga | 1542 |

<210> SEQ ID NO 57
<211> LENGTH: 1584
<212> TYPE: DNA
<213> ORGANISM: artificial
<220> FEATURE:
<223> OTHER INFORMATION: DNA sequence (DHAMDH02083016) for 2xCon4(C)
fused to the C-terminus of the Heavy Chain of Bevacizumab, with
linker peptide GGGGSGGGGSGGGGS

<400> SEQUENCE: 57

| | |
|---|---|
| atgggttggt cctgtatcat tcttttcctc gtcgccactg ccaccggagt ccactcagaa | 60 |
| gtccagttgg tggagtcggg aggaggactg gtgcagccag cggctccct cgcctgtcc | 120 |
| tgcgcggcgt ccgggtacac cttcaccaac tacggcatga actgggtccg ccaggccccc | 180 |
| ggaaaggggc tggaatgggt cggctggatc aacacttaca ccggagaacc tacctacgct | 240 |
| gccgatttca gcggcgcgtt tactttctcg ctggacacct ccaagagcac cgcctatctc | 300 |
| caaatgaact ccctgcgggc cgaggatacc gccgtgtact attgcgcgaa gtaccccac | 360 |

| | |
|---|---:|
| tattacggtt cgtcccattg gtacttcgac gtctggggcc agggaactct tgtcactgtg | 420 |
| tcctccgcat ccaccaaggg accgtcagtg ttccccctgg ccccgtcctc caaaagcact | 480 |
| agcggaggaa ccgcagcctt gggatgcctc gtcaaggact actttcccga gcctgtcacc | 540 |
| gtgtcgtgga actccggtgc cctcacttcg ggcgtgcaca cgttcccagc ggtgctgcag | 600 |
| tccagcggac tgtactcgct gtcctccgtc gtgaccgtgc cttcatcgag cctggggacc | 660 |
| cagacctaca tttgcaacgt gaaccacaag ccctccaaca ccaaagtgga caagaaggtc | 720 |
| gaaccaaaga gctgcgacaa gacccacact tgcccgccgt gcccggcccc tgagttgctg | 780 |
| ggtggtccat cggtgttcct gttcccgcct aagccgaagg acacactcat gatcagcagg | 840 |
| acccccgaag tgacctgtgt ggtggtcgac gtgtcacatg aagatcccga ggtcaagttc | 900 |
| aattggtacg tggacggagt ggaagtgcat aatgccaaga ctaagccgag agaggaacag | 960 |
| tacaactcca cctaccgggt ggtgtcagtg ctgaccgtgc tccatcagga ctggctcaac | 1020 |
| ggcaaggagt acaagtgcaa agtgtcgaac aaggctctcc cgccccctat cgagaaaacc | 1080 |
| attagcaagg ctaagggaca gccgcgggag ccgcaagtgt acaccctgcc cccgagccgc | 1140 |
| gaagaaatga ctaagaacca agtgtccctg acctgtctcg tgaaagggtt ctacccgtcg | 1200 |
| gacatcgctg tggagtggga gtctaatggt caacctgaga caactacaa gactactccc | 1260 |
| cctgtgctgg actccgatgg ttcctttttc ctgtactcaa agctgaccgt ggacaagtcc | 1320 |
| agatggcagc agggcaacgt gttcagctgc tccgtgatgc atgaagcact tcacaaccac | 1380 |
| tacacccaga gtccctcag cctgtctccg gggaagggcg gcggaggagg ggcccagcag | 1440 |
| gaagagtgtg aatgggaccc ctggacttgt gaacacatgg gcggcggcgg ctccggtgga | 1500 |
| ggaggatccg gcggagggg cagcgcgacg caccaggagg agtgcgaatg ggatccatgg | 1560 |
| acttgcgaac acatgctgga gtga | 1584 |

<210> SEQ ID NO 58
<211> LENGTH: 702
<212> TYPE: DNA
<213> ORGANISM: artificial
<220> FEATURE:
<223> OTHER INFORMATION: DNA sequence (DHAMDL083016), for the light chain of Bevacizumab

<400> SEQUENCE: 58

| | |
|---|---:|
| atgggttggt cctgtattat cctctttctc gtcgccactg ccaccggagt gcactcagat | 60 |
| attcagatga cccagagccc ctcctcactg tccgcttccg tggggaccg cgtgactatc | 120 |
| acttgctcgg cttcccaaga tatctccaac tacctgaact ggtaccagca gaagcccgga | 180 |
| aaggccccga agtgctcat ctacttcacc tcatcgctgc actcgggagt gccctcaaga | 240 |
| ttttccggct ccggaagcgg gaccgacttc actcttacca tctcatcgtt gcaaccagag | 300 |
| gatttcgcga cctactactg tcagcagtac tccacggtgc cgtggacctt cggacaaggc | 360 |
| accaaagtgg agatcaagag gactgtggcg gccccgagcg tgttcatttt ccctccttcc | 420 |
| gacgagcagc tgaaaagcgg caccgcctcg gtcgtgtgcc tcctgaacaa cttctacccg | 480 |
| cgggaagcca aggtccagtg gaaggtcgac aacgcgctgc agagcggaaa ttcccaggag | 540 |
| agcgtgaccg aacaggactc caaggacagc acctattccc tgtcgtctac actgaccctg | 600 |
| agcaaggccg actacgagaa gcataaggtc tacgcatgcg aagtgaccca ccaaggtctt | 660 |
| tcctcccctg tgaccaagtc cttcaaccgg ggcgaatgct ga | 702 |

-continued

```
<210> SEQ ID NO 59
<211> LENGTH: 822
<212> TYPE: DNA
<213> ORGANISM: artificial
<220> FEATURE:
<223> OTHER INFORMATION: DNA sequence (LY2.55.1), for peptide L1-15 (no
      LE) fused to the N-terminus of the light chain of Bevacizumab

<400> SEQUENCE: 59
atggcctgga tgatgttgct tctcggactt ctcgcgtatg gatcaggggt ggatagcgcg      60
caacagaagt accagccttt ggacgaactg gacaagaccc tgtacgacca gttcatgctg     120
caacagggag ggggcggtgg atccgggggc ggcggctccg gcggtggcgg atccgacatt     180
caaatgactc agtcgccatc gtccctctcg gcatccgtgg gagacagagt gaccatcact     240
tgttccgcct cgcaagacat ctccaactac ctgaactggt accagcagaa gcccgggaag     300
gcccccaaag tgctcatcta ctttacttcc tcactgcact ccggggtgcc aagccgcttt     360
agcggctccg gttctggaac cgatttcacc ctgaccatta gctcactcca gccggaagat     420
ttcgctacgt actactgcca gcagtattcg accgtgccgt ggactttcgg acagggtacc     480
aaagtcgaga tcaagcggac cgtggccgcc ccgagcgtgt tcattttccc gccttccgac     540
gagcaactca gtccggcac tgcctccgtg gtctgcctgc tgaacaattt ctaccccgc      600 gaggctaagg tccagtggaa ggtcgataac gcactgcagt ccggaaacag ccaagagagc     660
gtgaccgaac aggactccaa ggactcaact tactcgctga gctccaccct gaccctgtcg     720
aaggccgact acgaaaagca caaagtgtac gcctgcgaag tgacacatca gggcctgtca     780
tcccctgtca ccaagtcctt caaccgggga gagtgctgat aa                        822

<210> SEQ ID NO 60
<211> LENGTH: 828
<212> TYPE: DNA
<213> ORGANISM: artificial
<220> FEATURE:
<223> OTHER INFORMATION: DNA sequence (LY2.55.2), for peptide L1-15
      (with LE) fused to the N-terminus of the light chain of
      Bevacizumab

<400> SEQUENCE: 60
atggcctgga tgatgttgct tctcggactt ctcgcgtatg gatcaggggt ggatagcgcg      60
caacagaagt accagccttt ggacgaactg gacaagaccc tgtacgacca gttcatgctg     120
caacagggac tggaaggggg cggtggatcc ggggcggcg gctccggcgg tggcggatcc     180
gacattcaaa tgactcagtc gccatcgtcc ctctcggcat ccgtgggaga cagagtgacc     240
atcacttgtt ccgcctcgca agacatctcc aactacctga actggtacca gcagaagccc     300
gggaaggccc ccaaagtgct catctacttt acttcctcac tgcactccgg ggtgccaagc     360
cgctttagcg gctccggttc tggaaccgat ttcaccctga ccattagctc actccagccg     420
gaagatttcg ctacgtacta ctgccagcag tattcgaccg tgccgtggac tttcggacag     480
ggtaccaaag tcgagatcaa gcggaccgtg gccgccccga gcgtgttcat tttcccgcct     540
tccgacgagc aactcaagtc cggcactgcc tccgtggtct gcctgctgaa caatttctac     600
ccccgcgagg ctaaggtcca gtggaaggtc gataacgcac tgcagtccgg aaacagccaa     660
gagagcgtga ccgaacagga ctccaaggac tcaacttact cgctgagctc caccctgacc     720
ctgtcgaagg ccgactacga aaagcacaaa gtgtacgcct gcgaagtgac acatcagggc     780
ctgtcatccc ctgtcaccaa gtccttcaac cggggagagt gctgataa                  828
```

<210> SEQ ID NO 61
<211> LENGTH: 1539
<212> TYPE: DNA
<213> ORGANISM: artificial
<220> FEATURE:
<223> OTHER INFORMATION: DNA sequence (LY2.55.3), for peptide L1-15 (no LE) fused to the N-terminus of the heavy chain of Bevacizumab

<400> SEQUENCE: 61

| | |
|---|---|
| atggcttgga tgatgctgct gcttggcctt ctcgcatacg gttccggagt cgatagcgcc | 60 |
| caacagaagt accagcctct ggacgaactg ataagaccc tgtacgatca gttcatgctg | 120 |
| caacaggggg gcggcggagg atcgggcggt ggtggatccg gcggcggcgg atccgaagtg | 180 |
| cagctcgtgg agagcggggg cggactcgtg cagccgggag gttcgctgag attgtcctgt | 240 |
| gccgcctccg gttacacctt taccaattac gggatgaact gggtccgcca ggcccccgga | 300 |
| aagggactgg aatgggtcgg ctggatcaac acatataccg gagagcccac ctacgccgcg | 360 |
| gacttcaagc ggagattcac cttttcactg gatacgtcaa agtcaactgc atacctccag | 420 |
| atgaactccc ttagggcgga agataccgcc gtgtactact gcgccaagta cccgcactat | 480 |
| tacgggtcca gccattggta cttcgacgtc tggggacagg gaccctcgt gaccgtcagc | 540 |
| agcgcctcca ccaagggccc gtccgtgttc cctcttgcgc cgtcgtccaa aagcacttcc | 600 |
| ggcggcactg ccgccctggg ctgcctcgta aggattact ccccggaacc ggtcaccgtg | 660 |
| tcgtggaact ccggagccct gacttcgggt gtccacacct ccctgcggt gctgcagagc | 720 |
| tccggtctgt actccctctc ttccgtggtc acggtgccct cctcatcact gggaacccag | 780 |
| acctacatct gcaacgtgaa ccacaagccc tcaaacacta aggtcgacaa gaaagtcgaa | 840 |
| ccgaagtcgt gcgacaagac ccacacttgc cctccgtgcc cggctcccga gctgctgggg | 900 |
| ggcccttccg tgttttttgtt cccgccgaaa ccaaaggaca ctctgatgat cagccgcact | 960 |
| ccggaagtga cctgtgtggt ggtggacgtg tcccacgagg acccagaagt gaaattcaat | 1020 |
| tggtacgtgg atggcgtgga agtgcacaac gctaagacta gccccgcga ggaacagtac | 1080 |
| aacagcactt accgggtggt gtcggtgctc accgtgctgc accaagattg gctcaacggg | 1140 |
| aaggagtaca agtgcaaagt ctccaacaag gccctgcccg cacctattga aaagaccatc | 1200 |
| agcaaggcca agggacagcc ccgggagccc caggtctaca ccctgcctcc ctcgcgcgaa | 1260 |
| gagatgacta gaaccaagt gtccctgacc tgtctggtca agggattcta tccttccgac | 1320 |
| attgccgtgg aatgggagtc caacgggcag ccagagaaca actacaagac cactccacct | 1380 |
| gtgctggact ccgacgggtc cttcttcttg tactcgaagc tgaccgtgga caagtcccgg | 1440 |
| tggcagcagg gaaacgtgtt cagctgctcc gtgatgcacg aggccttgca taatcattac | 1500 |
| acccaaaagt cgctgagctt gagcccggga aagtgataa | 1539 |

<210> SEQ ID NO 62
<211> LENGTH: 1545
<212> TYPE: DNA
<213> ORGANISM: artificial
<220> FEATURE:
<223> OTHER INFORMATION: DNA sequence (LY2.55.4), for peptide L1-15 (with LE) fused to the N-terminus of the heavy chain of Bevacizumab

<400> SEQUENCE: 62

| | |
|---|---|
| atggcttgga tgatgctgct gcttggcctt ctcgcatacg gttccggagt cgatagcgcc | 60 |
| caacagaagt accagcctct ggacgaactg ataagaccc tgtacgatca gttcatgctg | 120 |
| caacaggggc ttgagggcgg cggaggatcg ggcggtggtg gatccggcgg cggcggatcc | 180 |

```
gaagtgcagc tcgtggagag cgggggcgga ctcgtgcagc cgggaggttc gctgagattg      240
tcctgtgccg cctccggtta cacctttacc aattacggga tgaactgggt ccgccaggcc      300
cccggaaagg gactggaatg ggtcggctgg atcaacacat ataccggaga gcccacctac      360
gccgcggact tcaagcggag attcaccttt tcactggata cgtcaaagtc aactgcatac      420
ctccagatga actcccttag gcggaagat accgccgtgt actactgcgc caagtacccg       480
cactattacg ggtccagcca ttggtacttc gacgtctggg gacaggggac cctcgtgacc      540
gtcagcagcg cctccaccaa gggcccgtcc gtgttccctc ttgcgccgtc gtccaaaagc      600
acttccggcg gcactgccgc cctgggctgc ctcgtgaagg attacttccc ggaaccggtc      660
accgtgtcgt ggaactccgg agccctgact tcgggtgtcc acaccttccc tgcggtgctg      720
cagagctccg gtctgtactc cctctcttcc gtggtcacgg tgccctcctc atcactggga      780
acccagacct acatctgcaa cgtgaaccac aagccctcaa acactaaggt cgacaagaaa      840
gtcgaaccga gtcgtgcgaa caagacccac acttgccctc cgtgcccggc tcccgagctg      900 ctgggggcc cttccgtgtt tttgttcccg ccgaaaccaa aggacactct gatgatcagc       960
cgcactccgg aagtgacctg tgtggtggtg gacgtgtccc acgaggaccc agaagtgaaa     1020
ttcaattggt acgtggatgg cgtggaagtg cacaacgcta agactaagcc ccgcgaggaa     1080
cagtacaaca gcacttaccg ggtggtgtcg gtgctcaccg tgctgcacca agattggctc     1140
aacgggaagg agtacaagtg caaagtctcc aacaaggccc tgcccgcacc tattgaaaag     1200
accatcagca aggccaaggg acagccccgg gagcccagg tctacaccct gcctccctcg      1260
cgcgaagaga tgactaagaa ccaagtgtcc ctgacctgtc tggtcaaggg attctatcct     1320
tccgacattg ccgtggaatg ggagtccaac gggcagccag agaacaacta caagaccact     1380
ccacctgtgc tggactccga cgggtccttc ttcttgtact cgaagctgac cgtggacaag     1440
tcccggtggc agcagggaaa cgtgttcagc tgctccgtga tgcacgaggc cttgcataat     1500
cattcacccc aaaagtcgct gagcttgagc ccgggaaagt gataa                     1545
```

<210> SEQ ID NO 63
<211> LENGTH: 705
<212> TYPE: DNA
<213> ORGANISM: artificial
<220> FEATURE:
<223> OTHER INFORMATION: DNA sequence (LY2.55.5), for the light chain of Bevacizumab

<400> SEQUENCE: 63

```
atggcctgga tgatgttgct tctcggactt ctcgcgtatg atcaggggt ggactccgac        60 attcaaatga ctcagtcgcc atcgtccctc tcggcatccg tgggagacag agtgaccatc      120
acttgttccg cctcgcaaga catctccaac tacctgaact ggtaccagca gaagcccggg      180
aaggccccca agtgctcat ctactttact tcctcactgc actccggggt gccaagccgc       240
tttagcggct ccggttctgg aaccgatttc accctgacca ttagctcact ccagccggaa      300
gatttcgcta cgtactactg ccagcagtat tcgaccgtgc cgtggacttt cggacagggt      360
accaaagtcg agatcaagcg gaccgtggcc gccccgagcg tgttcatttt cccgccttcc      420
gacgagcaac tcaagtccgg cactgcctcc gtggtctgcc tgctgaacaa tttctacccc      480
cgcgaggcta aggtccagtg gaaggtcgat aacgcactgc agtccggaaa cagccaagag      540
agcgtgaccg aacaggactc caaggactca acttactcgc tgagctccac cctgaccctg      600
tcgaaggccg actacgaaaa gcacaaagtg tacgcctgcg aagtgacaca tcagggcctg      660
```

```
tcatcccctg tcaccaagtc cttcaaccgg ggagagtgct gataa           705
```

<210> SEQ ID NO 64
<211> LENGTH: 491
<212> TYPE: PRT
<213> ORGANISM: artificial
<220> FEATURE:
<223> OTHER INFORMATION: 2xCon4(C) fused to the C-terminus of the VEGF Trap

<400> SEQUENCE: 64

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350
```

-continued

```
Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

Gly Gly Gly Gly Gly Ala Gln Gln Glu Glu Cys Glu Trp Asp Pro Trp
        435                 440                 445

Thr Cys Glu His Met Gly Ser Gly Ser Ala Thr Gly Gly Ser Gly Ser
        450                 455                 460

Thr Ala Ser Ser Gly Ser Gly Ser Ala Thr His Gln Glu Glu Cys Glu
465                 470                 475                 480

Trp Asp Pro Trp Thr Cys Glu His Met Leu Glu
                485                 490
```

The invention claimed is:

1. A chimeric molecule, which comprises
an amino acid sequence at least 99% identical or 100% identical as one selected from the group consisting of SEQ ID NOS: 31, 32, and 34.

2. A chimeric molecule
which comprises an amino acid sequence at least 99% identical or 100% identical as one selected from SEQ ID NO: 37, 39, 41, 43, 45, 47, 49, 51, and 53.

3. A pharmaceutical composition comprising the chimeric molecule of claim 1 and a pharmaceutically acceptable excipient.

4. The pharmaceutical composition of claim 3, wherein the pharmaceutical composition contains one or more acceptable carriers.

5. The pharmaceutical composition of claim 3, wherein the pharmaceutical composition is in the form of a lyophilized formulation or an aqueous solution.

6. The pharmaceutical composition of claim 4, wherein the pharmaceutical composition includes one or more of carriers, an excipient, a diluent, a suitable binder, a lubricant, a suspension agent, a coating agent or a solubilizing agent.

7. A pharmaceutical composition comprising the chimeric molecule of claim 2 and a pharmaceutically acceptable excipient.

* * * * *